United States Patent
Straub et al.

(10) Patent No.: US 6,462,068 B1
(45) Date of Patent: Oct. 8, 2002

(54) HETEROCYCLYLMETHYL-SUBSTITUTED PYRAZOLE DERIVATIVES

(75) Inventors: Alexander Straub, Wuppertal; Chantal Fürstner, Mülheim/Ruhr; Ulrich Niewöhner, Wermelskirchen; Thomas Jaetsch, Köln; Achim Feurer, Odenthal; Raimund Kast, Wuppertal; Johannes-Peter Stasch, Solingen; Elisabeth Perzborn; Joachim Hütter, both of Wuppertal; Klaus Dembowsky, Schriesheim; Dieter Arlt, Lemgo, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 77 days.

(21) Appl. No.: 09/644,305

(22) Filed: Aug. 23, 2000

Related U.S. Application Data

(62) Division of application No. 09/284,172, filed as application No. PCT/EP97/05432 on Oct. 2, 1997, now Pat. No. 6,166,027.

(30) Foreign Application Priority Data

Oct. 14, 1996 (DE) .......................... 196 42 320
Oct. 14, 1996 (DE) .......................... 196 42 322
Oct. 14, 1996 (DE) .......................... 196 42 323
Oct. 14, 1996 (DE) .......................... 196 42 319

(51) Int. Cl.$^7$ ..................... A61K 31/416; C07D 405/04
(52) U.S. Cl. .................. 514/403; 344/333; 546/275.7; 548/361.1
(58) Field of Search ................... 548/361.1; 546/275.7; 514/403

(56) References Cited

FOREIGN PATENT DOCUMENTS

| DE | 25 03 815 | 8/1975 |
|---|---|---|
| EP | 135 781 | 4/1985 |
| EP | 220573 | 5/1987 |
| EP | 667 345 | 8/1995 |
| WO | 96 20192 | 7/1996 |

OTHER PUBLICATIONS

Chemical Abstracts, vol. 125, No. 3, Jul. 15, 1996, Abstract No. 33633m, S. Guo, et al., "Preparation. . . inhibitors" & CN 1 112 926 (Yongxin Pharmaceutical Industry Co., Ltd. Peop. Rep. China) Dec. 6, 1995.

S.–M. Yu et al., "Inhibition of Platelet . . . Vivo", vol. 87, No. 9, May 1, 1996, pp. 3758–3767.

C.–C. Wu, et al. "YC-1 inhibited. . . cyclase", British Journal of Pharmacology, vol. 116, No. 13, 1995, pp. 1973–1978.

C.R. Self, et al., "Romazarit: A Potential Disease . . . Drug" Journal of Medicinal Chemistry, vol. 34, No. 2, 1991, Washington, U.S. pp. 772–777.

G. Capozzi, et al., "Neighbouring Group . . . 3–benzamidopropyne", Tetrahedron Letters, vol. 22, No. 34, 1981 pp. 3325–3328.

Primary Examiner—Robert W. Ramsuer
(74) Attorney, Agent, or Firm—Norris McLaughlin & Marcus

(57) ABSTRACT

The present invention relates to new heterocyclylmethyl-substituted pyrazole derivatives, processes for their preparation and their use as medicaments, in particular as medicaments for treatment of cardiovascular diseases.

13 Claims, No Drawings

HETEROCYCLYLMETHYL-SUBSTITUTED PYRAZOLE DERIVATIVES

This application is a divisional of application Ser. No. 09/284,172, filed on Apr. 9, 1999, now U.S. Pat. No. 6,166,027, which was filed under 35 U.S.C. 371 and based on PCT/EP97/05432, filed Oct. 2, 1997.

The present invention relates to new heterocyclylmethyl-substituted pyrazole derivatives, processes for their preparation and their use as medicaments, in particular as medicaments for treatment of cardiovascular diseases.

It is already known that 1-benzyl-3-(substituted heteroaryl)-fused pyrazole derivatives inhibit stimulated platelet aggregation in vitro (cf. EP 667 345 A1). I The present invention relates to new heterocyclylmethyl-substituted pyrazole derivatives, in the embodiment designated I (roman one), of the general formula (I-I)

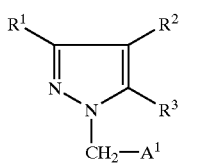

(I-I)

in which
R$^{1'}$ represents a 5-membered aromatic heterocyclic ring having one heteroatom, from the series consisting of S, N and/or O, or represents phenyl, which are optionally substituted up to 3 times in an identical or different manner by formyl, carboxyl, mercaptyl, hydroxyl, straight-chain or branched acyl, is alkylthio, alkoxy or alkoxycarbonyl having in each case up to 6 carbon atoms, nitro, cyano, halogen, phenyl or straight-chain or branched alkyl having up to 6 carbon atoms, which in its turn can be substituted by hydroxyl, amino, carboxyl, straight-chain or branched acyl, alkoxy, alkoxycarbonyl or acylamino having in each case up to 5 carbon atoms or by a radical of the formula —OR$^4$, wherein R$^4$ denotes straight-chain or branched acyl having up to 5 carbon atoms or a group of the formula —SiR$^5$R$^6$R$^7$, wherein R$^5$, R$^6$ and R$^7$ are identical or different and denote aryl having 6 to 10 carbon atoms or alkyl having up to 6 carbon atoms, and/or are substituted by a radical of the formula

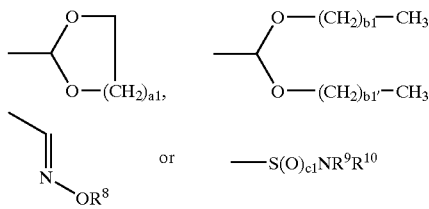

wherein
b1 and b1' are identical or different and denote the number 0, 1, 2 or 3,
a1 denotes the number 1, 2 or 3,
R$^8$ denotes hydrogen or straight-chain or branched alkyl having up to 4 carbon atoms,
c1 denotes the number 1 or 2 and
R$^9$ and R$^{10}$ are identical or different and denote hydrogen or straight-chain or branched alkyl having up to 10 carbon atoms, which is optionally substituted by cycloalkyl having 3 to 8 carbon atoms or by aryl having 6 to 10 carbon atoms, which in its turn can be substituted by halogen, or
denote aryl having 6 to 10 carbon atoms, which is optionally substituted by halogen, or
denote cycloalkyl having 3 to 7 carbon atoms, or R$^9$ and R$^{10}$, together with the nitrogen atom, form a 5- to 7-membered saturated heterocyclic ring, which can optionally contain a further oxygen atom or a radical —NR$^{11}$,
wherein
R$^{11}$ denotes hydrogen, straight-chain or branched alkyl having up to 4 carbon atoms or a radical of the formula

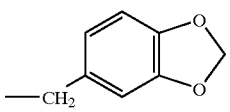

—CH$_2$ or denotes benzyl or phenyl, wherein the ring systems are optionally substituted by halogen,
R$^2$ and R$^3$, including the double bond, form a 5-membered aromatic heterocyclic ring having one heteroatom from the series consisting of S, N and/or O, or a phenyl ring, which are optionally substituted up to 3 times in an identical or different manner by formyl, carboxyl, hydroxyl, amino, straight-chain or branched acyl, alkoxy or alkoxycarbonyl having in each case up to 6 carbon atoms, nitro, cyano, azido, halogen, phenyl or straight-chain or branched alkyl having up to 6 carbon atoms, wherein the alkyl in its turn can be substituted by hydroxyl, amino, carboxyl, straight-chain or branched acyl, alkoxy or alkoxycarbonyl having in each case up to 5 carbon atoms,
and/or are optionally substituted by a radical of the formula —S(O)$_{c1'}$NR$^{9'}$R$^{10'}$, wherein c$_{1'}$, R$^{9'}$ and R$^{10'}$ have the abovementioned meaning of c$_1$, R$^9$ and R$^{10}$ and are identical to or different from these,
A$^1$ represents a 5- to 6-membered aromatic or saturated heterocyclic ring having up to 3 heteroatoms from the series consisting of S, N and/or O, which is optionally substituted up to 3 times in an identical or different manner by mercaptyl, hydroxyl, formyl, carboxyl, straight-chain or branched acyl, alkylthio, alkyloxyacyl, alkoxy or alkoxycarbonyl having in each case up to 6 carbon atoms, nitro, cyano, trifluoromethyl, azido, halogen, phenyl or straight-chain or branched alkyl having up to 6 carbon atoms, which in its turn can be substituted by hydroxyl, carboxyl, straight-chain or branched acyl, alkoxy or alkoxycarbonyl having in each case up to 5 carbon atoms,
and/or is substituted by a group of the formula —(CO)$_{d1}$—NR$^{12}$R$^{13}$, wherein
d1 denotes the number 0 or 1,
R$^{12}$ and R$^{13}$ are identical or different and denote hydrogen, phenyl, benzyl or straight-chain or branched alkyl or acyl having in each case up to 5 carbon atoms,
and their isomeric forms, salts and their N-oxides.

The compounds of the general formula (I-I) according to the invention can also be present in the form of their salts. Salts with organic or inorganic bases or acids may be mentioned in general here.

In the context of embodiment I of the present invention, physiologically acceptable salts are preferred. Physiologically acceptable salts of the heterocyclylmethyl-substituted pyrazole derivatives can be salts of the substances according to the invention with mineral acids, carboxylic acids or sulphonic acids. Particularly preferred salts are, for example, salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred salts are, for example, sodium, potassium, magnesium or calcium salts, and ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms which either behave as mirror images (enantiomers) or do not behave as mirror images (diastereomers). The invention relates both to the enantiomers or diastereomers or their particular mixtures. The racemic forms, like the diastereomers, can be separated into the stereoisomerically uniform constituents in a known manner.

Heterocyclic ring in the context of embodiment I of the invention, and depending on the abovementioned substituents, in general represents a 5- to 6-membered heterocyclic ring which can contain 1 heteroatom in the 5-membered ring in the case of $R^1$ and up to 3 heteroatoms from the series consisting of S, N and/or O in the case of A. Examples which may be mentioned are: pyridazinyl, pyridyl, pyrimidyl, thienyl, furyl, morpholinyl, pyrrolyl, thiazolyl, oxazolyl, imidazolyl, tetrahydropyranyl or tetrahydrofuranyl. Furyl, pyridyl, thienyl, pyrrolyl, pyrimidyl, pyridazinyl, morpholinyl, tetrahydropyranyl or tetrahydrofuranyl are preferred.

Preferred compounds of the general formula (I-I) according to the invention are those in which $R^1$ represents furyl, pyrrolyl, thienyl or phenyl, which are optionally substituted up to twice in an identical or different manner by formyl, carboxyl, hydroxyl, straight-chain or branched acyl, alkoxy or alkoxycarbonyl having in each case up to 5 carbon atoms, nitro, cyano, azido, fluorine, chlorine, bromine, phenyl or straight-chain or branched alkyl having up to 5 carbon atoms, which in its turn can be substituted by hydroxyl, amino, carboxyl, straight-chain or branched acyl, alkoxy, alkoxycarbonyl or acylamino having in each case up to 4 carbon atoms or by a radical of the formula —$OR^4$, wherein $R^4$ denotes straight-chain or branched acyl having up to 4 carbon atoms, and/or are substituted by a radical of the formula

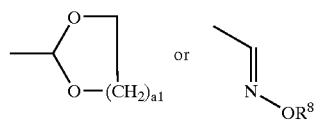

wherein a1 denotes the number 1, 2 or 3, $R^8$ denotes hydrogen or straight-chain or branched alkyl having up to 3 carbon atoms, $R^2$ and $R^3$, including the double bond, form a furyl, thienyl or phenyl ring, which are optionally substituted up to 3 times in an identical or different manner by formyl, carboxyl, hydroxyl, amino, straight-chain or branched acyl, alkoxy or alkoxycarbonyl having in each case up to 5 carbon atoms, nitro, cyano, azido, fluorine, chlorine, bromine, phenyl or straight-chain or branched alkyl having up to 5 carbon atoms, which in its turn can be substituted by hydroxyl, amino, carboxyl, straight-chain or branched acyl, alkoxy or alkoxycarbonyl having in each case up to 4 carbon atoms, $A^1$ represents tetrahydropyranyl, thienyl, furyl, tetrahydrofuranyl, pyrazinyl, morpholinyl, pyrimidyl, pyridazinyl or pyridyl, which are optionally substituted up to twice in an identical or different manner by hydroxyl, formyl, carboxyl, straight-chain or branched acyl, alkylthio, alkyloxyacyl, alkoxy or alkoxycarbonyl having in each case up to 4 carbon atoms, fluorine, chlorine, bromine, nitro, cyano, trifluoromethyl or straight-chain or branched alkyl having up to 4 carbon atoms, which in its turn can be substituted by hydroxyl, carboxyl, straight-chain or branched acyl, alkoxy or alkoxycarbonyl having in each case up to 4 carbon atoms, and/or are substituted by a group of the formula -$(CO)_{d1}$, —$NR^{12}R^{13}$, wherein d1 denotes the number 0 or 1, $R^{12}$ and $R^{13}$ are identical or different and denote hydrogen, phenyl, benzyl or straight-chain or branched alkyl or acyl having in each case up to 4 carbon atoms, and their isomeric forms and salts and their N-oxides.

Particularly preferred compounds of the general formula (I-I) according to the invention are those in which $R^1$ represents furyl, pyrryl, thienyl or phenyl, which are optionally substituted up to twice in an identical or different manner by formyl, straight-chain or branched acyl, alkoxy or alkoxycarbonyl having in each case up to 4 carbon atoms or straight-chain or branched alkyl having up to 4 carbon atoms, which in its turn can be substituted by hydroxyl, carboxyl, amino, straight-chain or branched acyl, alkoxy, alkoxycarbonyl or acylamino having in each case up to 3 carbon atoms, and/or are substituted by a radical of the formula

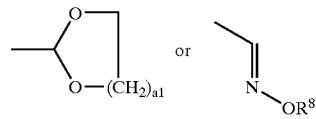

wherein a1 denotes the number 1 or 2, $R^8$ denotes hydrogen or methyl, $R^2$ and $R^3$, including the double bond, form a furyl, thienyl or phenyl ring, which are optionally substituted up to twice in an identical or different manner by formyl, carboxyl, hydroxyl, amino, straight-chain or branched acyl, alkoxy or alkoxycarbonyl having in each case up to 4 carbon atoms, nitro, cyano, fluorine, chlorine, phenyl or straight-chain or branched alkyl having up to 3 carbon atoms, which in its turn can be substituted by hydroxyl, amino, carboxyl, straight-chain or branched acyl, alkoxy or alkoxycarbonyl having in each case up to 3 carbon atoms, $A^1$ represents tetrahydropyranyl, tetrahydrofuranyl, thienyl, pyrimidyl, pyrazinyl, pyridazinyl, furyl or pyridyl, which are optionally substituted up to twice in an identical or different manner by formyl, carboxyl, straight-chain or branched acyl, alkylthio, alkyloxyacyl, alkoxy or alkoxycarbonyl having in each case up to 3 carbon atoms, fluorine, chlorine, bromine, nitro, cyano, trifluoromethyl, or straight-chain or branched alkyl having up to 3 carbon atoms, which in its turn can be substituted by hydroxyl, carboxyl, straight-chain or branched acyl, alkoxy or alkoxycarbonyl having in each case up to 3 carbon atoms, and/or are substituted by a group of the formula —(CO)$_{d1}$—NR$^{12}$R$^{13}$, wherein d1 denotes the number 0 or 1, R$^{12}$ and R$^{13}$ are identical or different and denote hydrogen or straight-chain or branched alkyl or acyl having in each case up to 3 carbon atoms, and their isomeric forms and salts and their N-oxides.

Especially preferred compounds of the general formula (I-I) according to the invention are those in which R$^1$ represents furyl, which is optionally substituted by formyl or by radical of the formula

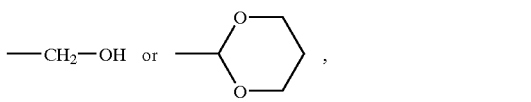

R$^2$ and R$^3$, including the double bond, form a phenyl ring which is substituted by phenyl, fluorine or nitro, A$^1$ represents furyl, pyridyl, pyrimidyl, pyridazinyl, thienyl, tetrahydrofuranyl or tetrahydropyranyl, which are optionally substituted by chlorine, bromine, methoxy, methoxycarbonyl or carboxyl, and their salts, isomeric forms and N-oxides.

The invention furthermore relates to processes for the preparation of the compounds of the general formula (I-I) according to the invention, characterized in that

[A1] compounds of the general formula (I-II)

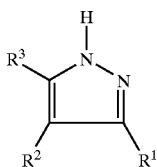

in which

R$^1$, R$^2$ and R$^3$ have the abovementioned meaning, are reacted with compounds of the general formula (I-III)

D$^1$—CH$_2$—A$^1$ (I-In)

in which

A$^1$ has the abovementioned meaning and

D$^1$ represents triflate or halogen, preferably bromine, in inert solvents, if appropriate in the presence of a base, or

[B1] compounds of the general formula (I-IV)

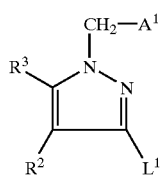

(I-IV)

in which

A$^1$, R$^2$ and R$^3$ have the abovementioned meaning and

L$^1$ represents a radical of the formula —SnR$^{14}$R$^{15}$R$^{16}$, ZnR$^{17}$, iodine or triflate, wherein R$^{14}$, R$^{15}$ and R$^{16}$ are identical or different and denote straight-chain or branched alkyl having up to 4 carbon atoms and R$^{17}$ denotes halogen, are reacted with compounds of the general formula (I-V)

R$^1$—T$^1$ (I-V)

in which

R$^1$ has the abovementioned meaning and in the case where L$^1$=SnR$^{14}$R$^{15}$R$^{16}$ or ZnR$^{17}$, T$^1$ represents triflate or represents halogen, preferably bromine, and in the case where L$^1$=iodine or triflate, T$^1$ represents a radical of the formula SnR$^{14'}$R$^{15'}$R$^{16'}$, ZnR$^{17'}$ or BR$^{18}$R$^{19}$, wherein R$^{14'}$, R$^{15'}$, R$^{16'}$ and R$^{17'}$ have the abovementioned meaning of R$^{14}$, R$^{15}$, R$^{16}$ and R$^{17}$ and are identical to or different from these, R$^{18}$ and R$^{19}$ are identical or different and denote hydroxyl, aryloxy having 6 to 10 carbon atoms or straight-chain or branched alkyl or alkoxy having in each case up to 5 carbon atoms, or together form a 5- or 6-membered carbocyclic ring, in a palladium-catalysed reaction in inert solvents, and, in the case of the radicals —S(O)$_{c1}$NR$^9$R$^{10}$ and —S(O)$_{c1'}$NR$^{9'}$R$^{10'}$, starting from the unsubstituted compounds of the general formula (I-I), these are first reacted with thionyl chloride, and finally the amine component is employed, and, if appropriate, the substituents listed under R$^1$, R$^2$, R$^3$ and/or A$^1$ are varied or introduced by customary methods, preferably by reduction, oxidation, splitting off of protective groups and/or nucleophilic substitution.

The processes according to the invention can be illustrated by way of example by the following equations.

[A1]

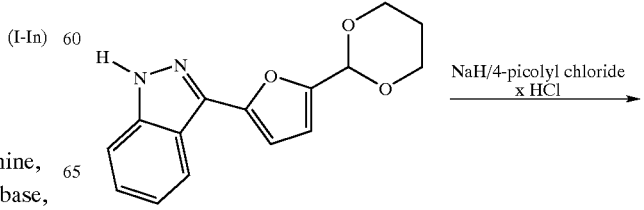

NaH/4-picolyl chloride
x HCl

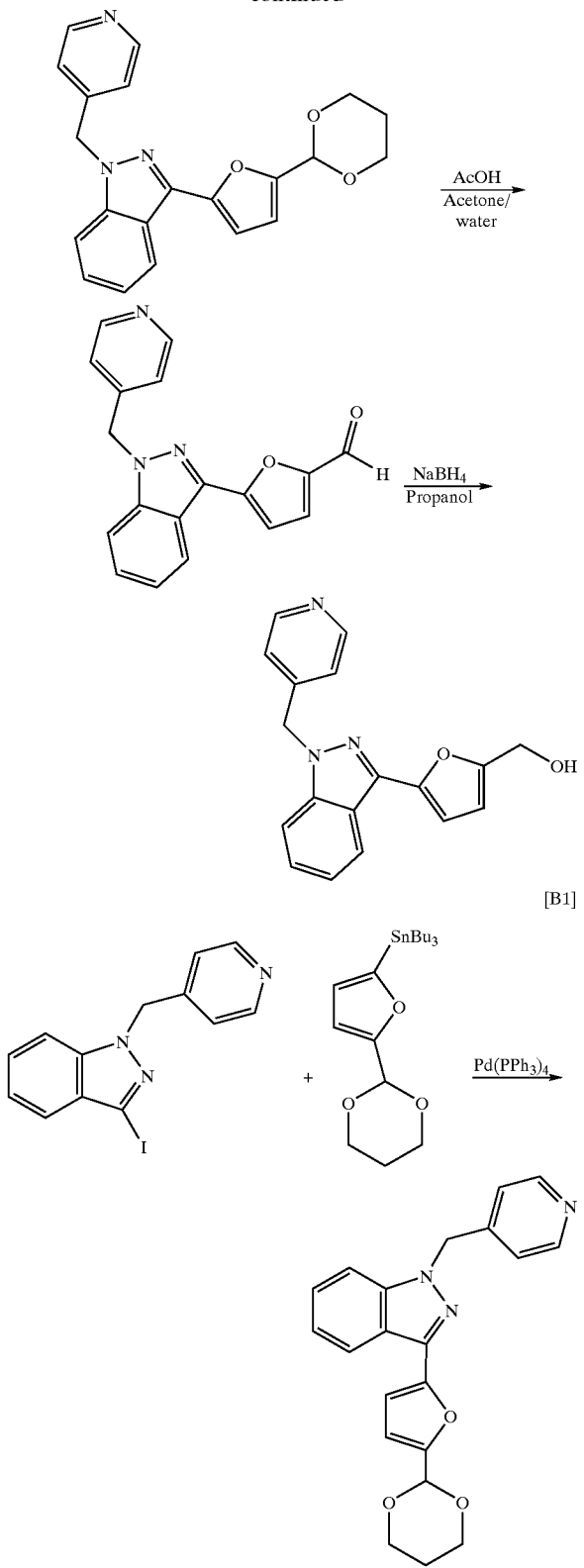

fractions, nitromethane, dimethylformamide, acetone, acetonitrile or hexamethylphosphoric acid triamide. It is also possible to employ mixtures of the solvents. Tetrahydrofuran, toluene or dimethylformamide are particularly preferred.

Bases which can be employed for the process according to the invention are in general inorganic or organic bases. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or alkali metal or alkaline earth metal alcoholates, such as sodium or potassium methanolate, sodium or potassium ethanolate or potassium tert-butylate, or organic amines (trialkyl- ($C_1$–$C_6$) amines), such as triethylamine, or heterocyclic compounds, such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ as the bases alkali metals, such as sodium, and hydrides thereof, such as sodium hydride. Sodium carbonate and potassium carbonate, triethylamine and sodium hydride are preferred.

The base is employed in an amount of 1 mol to 5 mol, preferably 1 mol to 3 mol, per mole of the compound of the general formula (I-II).

The reaction is in general carried out in a temperature range from 0° C. to 150° C., preferably from +20° C. to +110° C.

The reaction can be carried out under normal, increased or reduced pressure (for example 0.5 to 5 bar). It is in general carried out under normal pressure.

Suitable solvents here for process [B1] are inert organic solvents which do not change under the reaction conditions. These include ethers, such as diethyl ether or tetrahydrofuran, DME or dioxane, halogenohydrocarbons, such as methylene chloride, chloroform, carbon tetrachloride, trichloroethane, tetrachloroethane, 1,2-dichloroethane or trichloroethylene, hydrocarbons, such as benzene, xylene, toluene, hexane, cyclohexane or petroleum fractions, nitromethane, dimethylformamide, acetone, acetonitrile or hexamethylphosphoric acid triamide. It is also possible to employ mixtures of the solvents. Tetrahydrofuran, dimethylformamide, toluene, dioxane or dimethoxyethane are particularly preferred.

The reaction is in general carried out in a temperature range from 0° C. to 150° C., preferably from +20° C. to +110° C.

The reaction can be carried out under normal, increased or reduced pressure (for example 0.5 to 5 bar). It is in general carried out under normal pressure.

Suitable palladium compounds in the context of the present invention are in general $PdCl_2(P(C_6H_5)_3)_2$, palladium bis-dibenzylideneacetone $(Pd(dba)_2)$, [1,1'-bis-(diphenyl-phosphino)ferrocene]-palladium(II) chloride (Pd(dppf)$Cl_2$) or $Pd(P(C_6H_5)_3)_4$. $Pd(P(C_6H_5)_3)_4$ is preferred.

The compounds of the general formulae (I-III) and (I-V) are known per se or can be prepared by customary methods.

The compounds of the general formula (I-II) are known in some cases or are new, and can then be prepared by a process in which compounds of the general formula (I-VI)

Suitable solvents here for the individual steps of process [A1] are inert organic solvents which do not change under the reaction conditions. These include ethers, such as diethyl ether or tetrahydrofuran, hydrocarbons, such as benzene, xylene, toluene, hexane, cyclohexane or petroleum

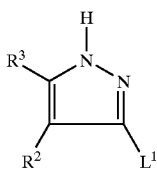

(I-VI)

in which
R² and R³ have the abovementioned meaning and
$L^{1'}$ has the abovementioned meaning of $L^1$ and is identical to or different from this,
are reacted with compounds of the general formula (I-V) analogously to the abovementioned process [B1].

The compounds of the general formula (I-IV) are known in some cases or, in the case of the stannyls, are new and can then be prepared, for example, by a process in which the compounds of the general formula (I-IVa)

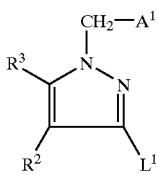

(I-IVa)

in which
R², R³ and A¹ have the abovementioned meaning, and
$L^{1'}$ represents triflate or halogen, preferably iodine,
are reacted with compounds of the general formula (I-VII)

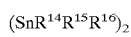

(I-VII)

in which
$R^{14}$, $R^{15}$ and $R^{16}$ have the abovementioned meaning, under palladium catalysis, as described above.

The compounds of the general formulae (I-IVa) and (I-VII) are known per se or can be prepared by customary methods.

The reductions are in general carried out with reducing agents, preferably with those which are suitable for reduction of carbonyl to hydroxy compounds. A particularly suitable reduction here is reduction with metal hydrides or complex metal hydrides in inert solvents, if appropriate in the presence of a trialkylborane. The reduction is preferably carried out with complex metal hydrides, such as, for example, lithium boranate, sodium boranate, potassium boranate, zinc boranate, lithium trialkylhydrido-boranate, diisobutylaluminium hydride or lithium aluminium hydride. The reduction is especially preferably carried out with diisobutylaluminium hydride and sodium borohydride.

The reducing agent is in general employed in an amount of 1 mol to 6 mol, preferably 1 mol to 4 mol, per mole of the compounds to be reduced.

The reduction in general proceeds in a temperature range from −78° C. to +50° C., preferably from −78° C. to 0° C., in the case of DIBAH, 0° C., room temperature in the case of $NaBH_4$, particularly preferably at −78° C., in each case depending on the choice of reducing agent and solvents.

The reduction in general proceeds under normal pressure, but it is also possible to carry it out under increased or reduced pressure.

The protective group is in general split off in one of the abovementioned alcohols and/or THF or acetone, preferably methanol/THF, in the presence of hydrochloric acid or trifluoroacetic acid or toluenesulphonic acid in a temperature range from 0° C. to 70° C., preferably at room temperature under normal pressure.

In the case where the radicals of the formulae $-S(O)_{c1}NR^9R^{10}$ and $-S(O)_{c1}NR^9R^{10'}$ are present, the corresponding unsubstituted compounds are first reacted with thionyl chloride. The reaction with the amines in one of the abovementioned ethers, preferably dioxane, is carried out in a second step. In the case where c1=2, oxidation by customary methods is subsequently carried out. The reactions are carried out in a temperature range from 0° C. to 70° C. under normal pressure. The invention moreover relates to the combination of the compounds of the general formula (I-I) according to the invention with organic nitrates and NO donors.

Organic nitrates and NO donors in the context of the invention are in general substances which display their therapeutic action via the liberation of NO or NO species. Sodium nitroprusside (SNP), nitroglycerol, isosorbide dinitrate, isosorbide mononitrate, molsidomine and SIN-I and similar substances are preferred.

The invention also relates to the combination with compounds which inhibit the breakdown of cyclic guanosine monophosphate (cGMP). These are, in particular, inhibitors of phosphodiesterases 1, 2 and 5; nomenclature according to Beavo and Reifsnyder (1990) TIPS 11 pages 150–155. The action of the compounds according to the invention is potentiated and the desired pharmacological effect increased by these inhibitors.

The compounds of the general formula (I-I) according to the invention show an unforeseeable, valuable pharmacological action spectrum.

The compounds of the general formula (I-I) according to the invention lead to a vessel relaxation, to an inhibition of platelet aggregation and to a lowering of blood pressure, as well as to an increase in coronary blood flow. These actions are mediated via direct stimulation of soluble guanylate cyclase and an intracellular increase in cGMP. Furthermore, the compounds according to the invention intensify the action of substances which increase the cGMP level, such as, for example, EDRF (endothelium derived relaxing factor), NO donors, protoporphyrin IX, arachidonic acid or phenylhydrazine derivatives. They can therefore be employed in medicaments for treatment of cardiovascular diseases, such as, for example, for treatment of high blood pressure and cardiac insufficiency, stable and unstable angina pectoris and peripheral and cardiac vascular diseases and of arrhythmias, for treatment of thromboembolic diseases and ischaemias, such as myocardial infarction, cerebral stroke, transitory and ischaemic attacks and peripheral circulatory disturbances, for preventing restenoses, such as after thrombolysis treatment, percutaneous transluminal angioplasties (PTA), percutaneous transluminal coronary angioplasties (PTCA) and bypass, and for treatment of arteriosclerosis and diseases of the urogenital system, such as, for example, prostate hypertrophy, erectile dysfunction and incontinence.

The following investigations were carried out to determine the cardiovascular actions: the influence on guanylate cyclase-dependent cGMP formation with and without an NO donor was tested in investigations in vitro on cells of vascular origin. The anti-aggregatory properties were demonstrated on human platelets stimulated with collagen. The vessel-relaxing action was determined on rabbit aortic rings precontracted with phenylephrine. The antihypertensive action was investigated on anaesthetized rats.

Stimulation of Soluble Guanylate Cyclase in Primary Endothelial Cells

Primary endothelial cells were isolated from pig aortas by treatment with collagenase solution. The cells were then cultured in a culture medium until confluence was reached. For the investigations, the cells were subjected to passaging, sown in cell culture plates and subcultured until confluence was reached. To stimulate the endothelial guanylate cyclase, the culture medium was suctioned off and the cells were washed once with Ringer's solution and incubated in stimulation buffer with or without an NO donor (sodium nitroprusside, SNP, 1 $\mu$M). Thereafter, the test substances (final concentration 1 $\mu$M) were pipetted onto the cells. At the end of the 10-minute incubation period, the buffered solution was suctioned off and the cells were lysed at $-20°$ C. for 16 hours. The intracellular cGMP was then determined radioimmunologically.

TABLE A

| Example No. | % increase in cGMP |
| --- | --- |
| I-4 | >1000 |
| I-10 | 217 |
| I-16 | >1000 |
| I-17 | 200 |
| I-18 | >1000 |
| I-22 | 146 |
| I-24 | 65 |

Vessel-relaxing Action in vitro

Rings 1.5 mm wide of an aorta isolated from a rabbit are introduced individually, under pretension, in 5 ml organ baths with Krebs-Henseleit solution warmed to 37° C. and gassed with carbogen. The contraction force is amplified and digitalized and recorded in parallel on a line recorder. To generate a contraction, phenylephrine is added cumulatively to the bath in an increasing concentration.

After several control cycles, the substance to be investigated is investigated in each further pass in each case in an increasing dosage, and a comparison is made with the level of the contraction achieved in the last preliminary pass. The concentration necessary to reduce the level of the control value by 50% ($IC_{50}$) is calculated from this. The standard application volume is 5 $\mu$l.

TABLE 2

| Example No. | Aorta $IC_{50}(\mu m)$ |
| --- | --- |
| I-4 | 8,0 |
| I-10 | 9,0 |
| I-16 | 9,1 |
| I-18 | 7,2 |
| I-19 | 15 |
| I-20 | 8,2 |
| I-21 | >27 |
| I-22 | 8,8 |
| I-23 | 2,9 |
| I-24 | 26 |

Blood Pressure Measurements on Anaesthetized Rats

Male Wistar rats with a body weight of 300–350 g are anaesthetized with thiopental (100 mg/kg i.p.). After tracheotomy, a catheter is inserted into the femoral artery for blood pressure measurement. The substances to be tested are administered orally by means of a stomach tube in various doses as a suspension in tylose solution.

Inhibition of Platelet Aggregation in vitro

To determine the platelet aggregation-inhibiting action, blood from healthy subjects of both sexes was used. One part of 3.8% strength aqueous sodium citrate solution was admixed to 9 parts of blood as an anticoagulant. Platelet-richer citrate plasma (PRP) is obtained from this blood by means of centrifugation.

For the investigations, 445 $\mu$l of PRP and 5 $\mu$l of the active compound solution were preincubated in a water-bath at 37° C. The platelet aggregation was then determined in an aggregometer at 37° C. For this, 50 $\mu$l of collagen, an aggregation-inducing agent, were added to the preincubated sample and the change in optical density was recorded. For the quantitative evaluation, the maximum aggregation response was determined and the percentage inhibition compared with the control was calculated therefrom.

The compounds described in embodiment I of the present invention are also active compounds for combating diseases in the central nervous system which are characterized by impairments of the NO/cGMP system. In particular, they are suitable for eliminating cognitive deficits, for improving learning and memory performance and for treatment of Alzheimer's disease. They are also suitable for treatment of diseases of the central nervous system such as states of anxiety, stress and depression, sexual dysfunctions of central nervous origin and sleep disturbances, and for regulating pathological disturbances in the intake of food and addictive substances.

These active compounds are furthermore also suitable for regulation of cerebral circulation and are therefore effective agents for combating migraine.

They are also suitable for prophylaxis and combating the consequences of cerebral infarction events (apoplexia cerebri), such as apoplexy, cerebral ischaemias and craniocerebral trauma. The compounds according to the invention can also be employed for combating states of pain.

The present invention includes pharmaceutical formulations which comprise, in addition to non-toxic, inert pharmaceutically suitable carriers, one or more compounds according to the invention, or which consist of one or more active compounds according to the invention, and processes for the preparation of these formulations.

If appropriate, the active compound or compounds can also be present in microencapsulated form in one or more of the abovementioned carriers.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also comprise further pharmaceutical active compounds in addition to the compounds according to the invention.

In general, it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, to achieve the desired results. An individual dose preferably comprises the active compound or compounds according to the invention in amounts of about 1 to about 80, in particular 3 to 30 mg/kg of body weight.

II

The present invention relates to new 1-heterocyclylmethyl-substituted pyrazoles, in the embodiment designated II (roman two), of the general formula (II-I),

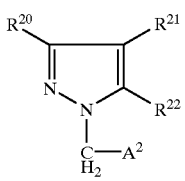
(II-I)

in which
- $R^{20}$ represents a 6-membered aromatic heterocyclic ring having up to 3 nitrogen atoms, which is optionally substituted up to 3 times in an identical or different manner by formyl, carboxyl, hydroxyl, mercaptyl, straight-chain or branched acyl, alkoxy, alkylthio or alkoxycarbonyl having in each case up to 6 carbon atoms, nitro, cyano, azido, halogen, phenyl and/or by a group of the formula

—$NR^{23}R^{24}$ wherein
  - $R^{23}$ and $R^{24}$ are identical or different and denote hydrogen or straight-chain or branched acyl having up to 6 carbon atoms or straight-chain or branched alkyl having up to 6 carbon atoms, which is optionally substituted by cycloalkyl having 3 to 6 carbon atoms, hydroxyl, amino or by straight-chain or branched alkoxy, acyl or alkoxycarbonyl having in each case up to 5 carbon atoms, or
  - $R^{23}$ and $R^{24}$, together with the nitrogen atom, form a 3- to 7-membered saturated or partly unsaturated heterocyclic ring, which can optionally additionally contain an oxygen or sulphur atom or a radical of the formula —$NR^{25}$,
    wherein
    - $R^{25}$ denotes hydrogen or straight-chain or branched alkyl having up to 4 carbon atoms,
  and/or is substituted by straight-chain or branched alkyl having up to 6 carbon atoms, which in its turn can be substituted by hydroxyl, amino, halogen, carboxyl, straight-chain branched acyl, alkoxy, alkoxycarbonyl or acylamino having in each case up to 5 carbon atoms or by a radical of the formula —$OR^{26}$,
    wherein
    - $R^{26}$ denotes straight-chain or branched acyl having up to 5 carbon atoms or a group of the formula —$SiR^{27}R^{28}R^{29}$, wherein
      - $R^{27}$, $R^{28}$ and $R^{29}$ are identical or different and denote aryl having 6 to 10 carbon atoms or alkyl having up to 6 carbon atoms,
  and/or is optionally substituted by a radical of the formula

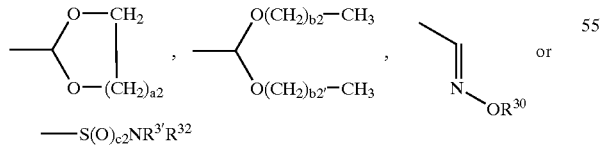

wherein
  - b2 and b2' are identical or different and denote the number 0, 1, 2 or 3,
  - a2 denotes the number 1, 2 or 3,
  - $R^{30}$ denotes hydrogen or straight-chain or branched alkyl having up to 4 carbon atoms,
  - c2 denotes the number 1 or 2 and
  - $R^{31}$ and $R^{32}$ are identical or different and denote hydrogen or straight-chain or branched alkyl having up to 10 carbon atoms, which is optionally substituted by cycloalkyl having 3 to 8 carbon atoms or by aryl having 6 to 10 carbon atoms, which in its turn can be substituted by halogen, or
    denote aryl having 6 to 10 carbon atoms, which is optionally substituted by halogen, or
    denote cycloalkyl having 3 to 7 carbon atoms, or
  - $R^{31}$ and $R^{32}$, together with the nitrogen atom, form a 5- to 7-membered saturated heterocyclic ring, which can optionally contain a further oxygen atom or a radical —$NR^{33}$, wherein
    - $R^{33}$ denotes hydrogen, straight-chain or branched alkyl having up to 4 carbon atoms or a radical of the formula

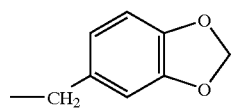

or denotes benzyl or phenyl, wherein the ring systems are optionally substituted by halogen,
- $R^{21}$ and $R^{22}$, including the double bond, form a 5-membered aromatic heterocyclic ring having a heteroatom from the series consisting of S, N and/or O, or a phenyl ring, which are optionally substituted up to 3 times in an identical or different manner by formyl, mercaptyl, carboxyl, hydroxyl, amino, straight-chain or branched acyl, alkylthio, alkoxy or alkoxycarbonyl having in each case up to 6 carbon atoms, nitro, cyano, azido, halogen, phenyl or straight-chain or branched alkyl having up to 6 carbon atoms, which in its turn can be substituted by hydroxyl, amino, carboxyl, straight-chain or branched acyl, alkoxy or alkoxycarbonyl having in each case up to 5 carbon atoms, or are optionally substituted by a group of the formula —$S(O)_{c2'}NR^{31'}R^{32'}$ wherein $c_{2'}$, $R^{31'}$ and $R^{32'}$ have the above-mentioned meaning of c2, $R^{31}$ and $R^{32}$ and are identical to or different from these,
- $A^2$ represents phenyl or a 5- to 6-membered aromatic or saturated heterocyclic ring having up to 3 heteroatoms from the series consisting of S, N and/or O, which are optionally substituted up to 3 times in an identical or different manner by mercaptyl, hydroxyl, formyl, carboxyl, straight-chain or branched acyl, alkylthio, alkyloxyacyl, alkoxy or alkoxycarbonyl having in each case up to 6 carbon atoms, nitro, cyano, trifluoromethyl, azido, halogen, phenyl or straight-chain or branched alkyl having up to 6 carbon atoms, which in its turn can be substituted by hydroxyl, carboxyl, straight-chain or branched acyl, alkoxy or alkoxycarbonyl having in each case up to 5 carbon atoms, and/or is substituted by a group of the formula —$(CO)_{d2}$—$NR^{34}R^{35}$, wherein
  - d2 denotes the number 0 or 1,
  - $R^{34}$ and $R^{35}$ are identical or different and denote hydrogen, phenyl, benzyl or straight-chain or branched alkyl or acyl having in each case up to 5 carbon atoms, their isomeric forms and salts and their N-oxides.

In the context of embodiment II of the present invention, physiologically acceptable salts with organic or inorganic bases or acids are preferred. Physiologically acceptable salts of the 1-heterocyclyl-methyl-substituted pyrazoles can be salts of the substances according to the invention with mineral acids, carboxylic acids or sulphonic acids. Particularly preferred salts are, for example, salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred salts are, for example, sodium, potassium, magnesium or calcium salts, and ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

The compounds according to the invention according to embodiment II can exist in stereoisomeric forms which either behave as mirror images (enantiomers) or do not behave as mirror images (diastereomers). The invention relates both to the enantiomers or diastereomers or their particular mixtures. The racemic forms, like the diastereomers, can be separated into the stereoisomerically uniform constituents in a known manner. Heterocyclic ring in the context of the invention according to embodiment II represents a 6-membered aromatic heterocyclic ring in the case of $R^{20}$, a 5-membered aromatic heterocyclic ring having 1 heteroatom in the case of $R^{21}/R^2$, and a 5- to 6-membered aromatic or saturated heterocyclic ring in the case of $A^2$, and a saturated or partly unsaturated 3- to 7-membered heterocyclic ring in the case of the group $NR^{23}R^{24}$. Examples which may be mentioned are: pyridazinyl, quinolyl, isoquinolyl, pyrazinyl, pyridyl, pyrimidyl, thienyl, furyl, morpholinyl, pyrrolyl, thiazolyl, oxazolyl, imidazolyl, tetrahydropyranyl or tetrahydrofuranyl.

Preferred compounds of the general formula (II-I) according to the invention are those in which $R^{20}$ represents a radical of the formula

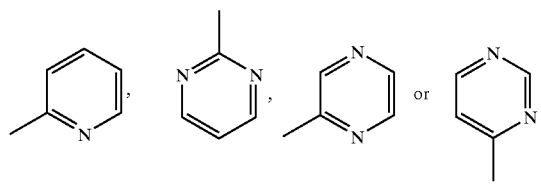

which are optionally substituted up to 3 times in an identical or different manner by formyl, carboxyl, hydroxyl, straight-chain or branched acyl, alkoxy or alkoxycarbonyl having in each case up to 5 carbon atoms, nitro, cyano, azido, fluorine, chlorine, bromine, phenyl and/or by a group of the formula

—$NR^{23}R^{24}$, wherein $R^{23}$ and $R^{24}$ are identical or different and denote hydrogen or straight-chain or branched acyl having up to 4 carbon atoms or straight-chain or branched alkyl having up to 4 carbon atoms, which is optionally substituted by hydroxyl, amino or by straight-chain or branched alkoxy having up to 3 carbon atoms, or $R^{23}$ and $R^{24}$, together with the nitrogen atom, form a morpholine ring or a radical of the formula

and/or are substituted by straight-chain or branched alkyl having up to 5 carbon atoms, which in its turn can be substituted by hydroxyl, amino,fluor, carboxyl, straight-chain or branched acyl, alkoxy, alkoxycarbonyl or acylamino having in each case up to 4 carbon atoms or by a radical of the formula —$OR^{26}$, wherein $R^{26}$ denotes straight-chain or branched acyl having up to 4 carbon atoms, and/or are optionally substituted by a radical of the formula

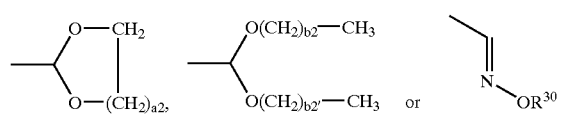

wherein
b2 and b2' are identical or different and denote the number 0, 1, 2 or 3,
a2 denotes the number 1, 2 or 3,
$R^{30}$ denotes hydrogen or straight-chain or branched alkyl having up to 4 carbon atoms, $R^{21}$ and $R^{22}$, including the double bond, form a furyl, thienyl or phenyl ring, which are optionally substituted up to 3 times in an identical or different manner by formyl, carboxyl, hydroxyl, amino, straight-chain or branched acyl, alkoxy or alkoxycarbonyl having in each case up to 5 carbon atoms, nitro, cyano, azido, fluorine, chlorine, bromine, phenyl or straight-chain or branched alkyl having up to 5 carbon atoms, which in its turn can be substituted by hydroxyl, amino, carboxyl, straight-chain or branched acyl, alkoxy or alkoxycarbonyl having in each case up to 4 carbon atoms, $A^2$ represents phenyl, or represents tetrahydropyranyl, furyl, tetrahydrofuranyl, morpholinyl, pyrimidyl, pyridazinyl or pyridyl, which are optionally substituted up to twice in an identical or different manner by hydroxyl, formyl, carboxyl, straight-chain or branched acyl, alkylthio, alkyloxyacyl, alkoxy or alkoxycarbonyl having in each case up to 4 carbon atoms, fluorine, chlorine, bromine, nitro, cyano, trifluoromethyl or straight-chain or branched alkyl having up to 4 carbon atoms, which in its turn can be substituted by hydroxyl, carboxyl, straight-chain or branched acyl, alkoxy or alkoxycarbonyl having in each case up to 4 carbon atoms, and/or are substituted by a group of the formula —(CO)$_2$—$NR^{34}R^{35}$ wherein d2 denotes the number 0 or 1, $R^{34}$ and $R^{35}$ are identical or different and denote hydrogen, phenyl, benzyl or straight-chain or branched alkyl or acyl having in each case up to 4 carbon atoms, their isomeric forms and salts and their N-oxides.

Particularly preferred compounds of the general formula (II-I) according to the invention are those in which $R^{20}$ represents a radical of the formula

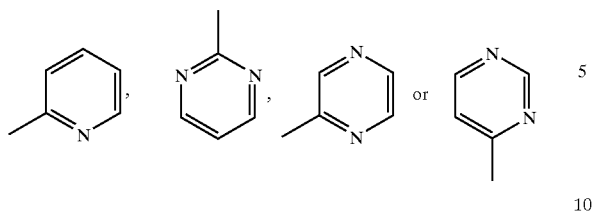

wherein the ring systems are optionally substituted up to 3 times in an identical or different manner by formyl, straight-chain or branched acyl, alkoxy or alkoxycarbonyl having in each case up to 4 carbon atoms, methylamino, amino, fluorine, chlorine, bromine, cyano, azido or straight-chain or branched alkyl having up to 4 carbon atoms, which in its turn can be substituted by hydroxyl, carboxyl, amino, straight-chain or branched acyl, alkoxy, alkoxycarbonyl or acylamino having in each case up to 3 carbon atoms, and/or are optionally substituted by a radical of the formula

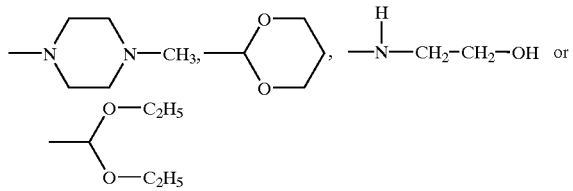

$R^{21}$ and $R^{22}$, including the double bond, form a furyl, thienyl or phenyl ring, which are optionally substituted up to twice in an identical or different manner by formyl, carboxyl, hydroxyl, amino, straight-chain or branched acyl, alkoxy or alkoxycarbonyl having in each case up to 4 carbon atoms, nitro, cyano, fluorine, chlorine, phenyl or straight-chain or branched alkyl having up to 3 carbon atoms, which in its turn can be substituted by hydroxyl, amino, carboxyl, straight-chain or branched acyl, alkoxy or alkoxycarbonyl having in each case up to 3 carbon atoms, $A^2$ represents phenyl, tetrahydropyranyl, tetrahydrofuranyl, furyl or pyridyl, which are optionally substituted up to twice in an identical or different manner by formyl, carboxyl, straight-chain or. branched acyl, alkylthio, alkyloxyacyl, alkoxy or alkoxycarbonyl having in each case up to 3 carbon atoms, fluorine, chlorine, bromine, nitro, cyano, trifluoromethyl or represents straight-chain or branched alkyl having up to 3 carbon atoms, which in its turn can be substituted by hydroxyl, carboxyl, straight-chain or branched acyl, alkoxy or alkoxycarbonyl having in each case up to 3 carbon atoms, and/or are substituted by a group of the formula —(CO)$_{d2}$—NR$^{34}$R$^{35}$, wherein d2 denotes the number 0 or 1, $R^{34}$ and $R^{35}$ are identical or different and denote hydrogen or straight-chain or branched alkyl or acyl having in each case up to 3 carbon atoms, their isomeric forms, salts and N-oxides.

Especially preferred compounds of the general formula (II-I) according to the invention are those in which $R^{20}$ represents a radical of the formula

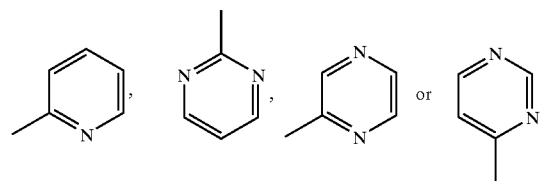

wherein the abovementioned heterocyclic ring systems are optionally substituted up to 3 times in an identical or different manner by methyl, fluorine, formyl, amino, cyano, methoxy, methoxycarbonyl, methylamino, chlorine or by a radical of the formula

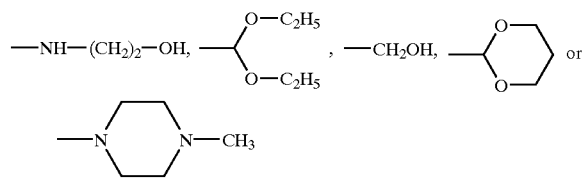

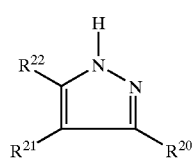

$R^{21}$ and $R^{22}$, including the double bond, together form a phenyl ring and $A^2$ represents phenyl, which is optionally substituted by fluorine or cyano, and their isomeric forms, salts and N-oxides.

The invention furthermore relates to processes for the preparation of compounds of the general formula (II-I), characterized in that

[A2] compounds of the general formula (II-II)

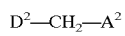

(II-II)

in which $R^{20}$, $R^{21}$ and $R^{22}$ have the abovementioned meaning, are reacted with compounds of the general formula (II-III)

$$D^2\text{—}CH_2\text{—}A^2 \quad \text{(II-III)}$$

in which $A^2$ has the abovementioned meaning, and $D^2$ represents triflate or halogen, preferably bromine, in inert solvents, if appropriate in the presence of a base, or

[B2] compounds of the general formula (II-IV)

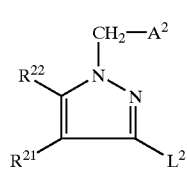

(II-IV)

in which $A^2$, $R^{21}$ and $R^{22}$ have the abovementioned meaning and $L^2$ represents a radical of the formula —SnR$^{36}$ R$^{37}$R$^3$, ZnR$^{39}$, iodine or triflate, wherein $R^{36}$, $R^{37}$ and $R^{38}$ are identical or different and denote straight-chain or branched alkyl having up to 4 carbon atoms and $R^{39}$ denotes halogen, are reacted with compounds of the general formula (II-V)

$$R^{20}—T^2 \qquad (II\text{-}V)$$

in which $R^{20}$ has the abovementioned meaning and in the case where $L^2=SnR^{36}R^{37}R^{38}$ or $ZnR^{39}$, $T^2$ represents triflate or represents halogen, preferably bromine, and in the case where $L^2$=iodine or triflate, $T^2$ represents a radical of the formula $SnR^{36'}R^{37'}R^{38'}$, $ZnR^{39'}$ or $BR^{40}R^{41}$, wherein $R^{36'}$, $R^{37'}$, $R^{38'}$ and $R^{39'}$ have the abovementioned meaning of $R^{36}$, $R^{37}$, $R^{38}$ and $R^{39}$ and are identical to or different from these and $R^{40}$ and $R^{41}$ are identical or different and denote hydroxyl, aryloxy having 6 to 10 carbon atoms or straight-chain or branched alkyl or alkoxy having in each case up to 5 carbon atoms, or together form a 5- or 6-membered carbocyclic ring, in a palladium-catalysed reaction in inert solvents, and, in the case of the radicals —S(O)$_{c2}$NR$^{31}$R$^{32}$ and —S(O)$_{c2'}$NR$^{31'}$R$^{32'}$, starting from the unsubstituted compounds of the general formula (II-I), these are first reacted with thionyl chloride and finally the amine component is employed, and, if appropriate, the substituents listed under $R^{20}$, $R^{21}$, $R^{22}$ and/or $A^2$ are varied or introduced by customary methods, preferably by reduction, oxidation, splitting off of protective groups and/or nucleophilic substitution.

The processes according to the invention for the preparation of the compounds according to embodiment II can be illustrated by way of example by the following equations:

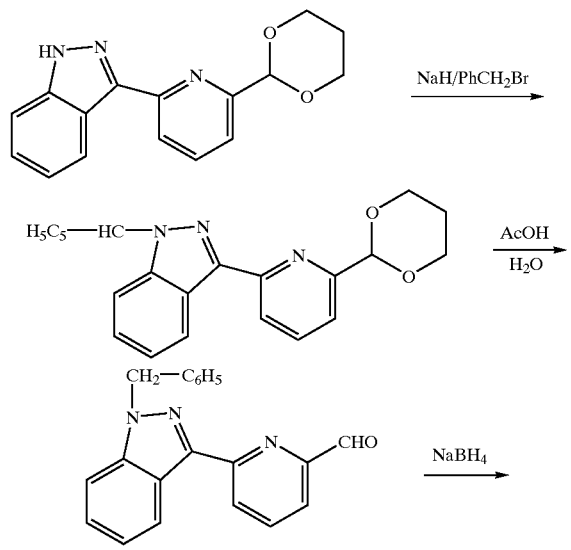

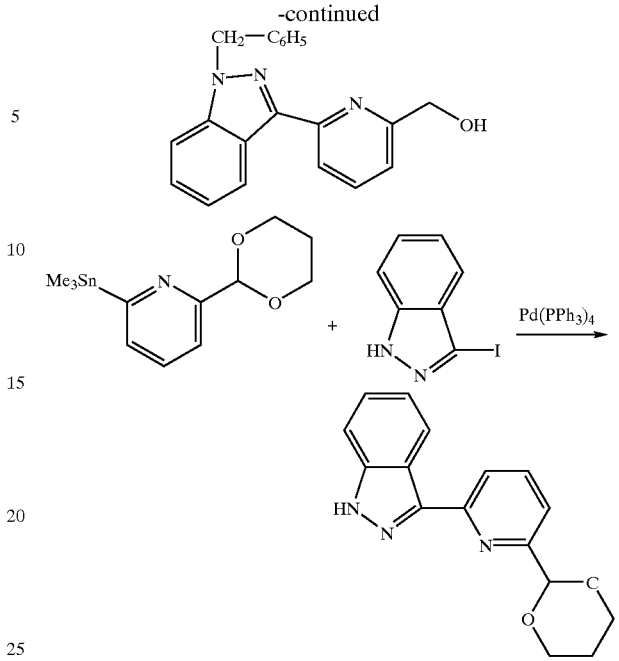

Suitable solvents here for the individual steps of process [A2] are inert organic solvents which do not change under the reaction conditions. These include ethers, such as diethyl ether or tetrahydrofuran, hydrocarbons, such as benzene, xylene, toluene, hexane, cyclohexane or petroleum fractions, nitromethane, dimethylformamide, acetone, acetonitrile or hexamethylphosphoric acid triamide. It is also possible to employ mixtures of the solvents. Tetrahydrofuran, toluene or dimethylformamide are particularly preferred.

Bases which can be employed for the process according to the invention according to embodiment II are in general inorganic or organic bases. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or alkali metal or alkaline earth metal alcoholates, such as sodium or potassium methanolate, sodium or potassium ethanolate or potassium tert-butylate, or organic amines (trialkyl-(C$_1$–C$_6$)amines), such as triethylamine, or heterocyclic compounds, such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ as the bases alkali metals, such as sodium, and hydrides thereof, such as sodium hydride. Sodium carbonate and potassium carbonate, triethylamine and sodium hydride are preferred.

The base is employed in an amount of 1 mol to 5 mol, preferably 1 mol to 3 mol, per mole of the compound of the general formula (II-II).

The reaction is in general carried out in a temperature range from 0° C. to 150° C., preferably from +20° C. to +110° C.

The reaction can be carried out under normal, increased or reduced pressure (for example 0.5 to 5 bar). It is in general carried out under normal pressure. Suitable solvents here for process [B2] are inert organic solvents which do not change under the reaction conditions. These include ethers, such as diethyl ether or tetrahydrofuran, DME or dioxane, halogenohydrocarbons, such as methylene chloride, chloroform, carbon tetrachloride, trichloroethane, tetrachloroethane, 1,2-dichloroethane or trichloroethylene, hydrocarbons, such as benzene, xylene, toluene, hexane, cyclohexane or petroleum fractions, nitromethane, dimethylformamide, acetone, acetonitrile or hexamethylphosphoric acid triamide. It is also possible to employ mixtures of the solvents. Tetrahydrofuran, dimethylformamide, toluene, dioxane or dimethoxyethane are particularly preferred.

The reaction is in general carried out in a temperature range from 0° C. to 150° C., preferably from +20° C. to +110° C.

The reaction can be carried out under normal, increased or reduced pressure (for example 0.5 to 5 bar). It is in general carried out under normal pressure.

Suitable palladium compounds in the context of the present invention are in general $PdCl_2((C_6H_5)_3)_2$, palladium bis-dibenzylideneacetone $(Pd(dba)_2)$, [1,1'-bis-(diphenylphosphino)ferrocene]-palladium(II) chloride $(Pd(dppf)Cl_2)$ or $Pd(P(C_6H_5)_3)_4$. $Pd(P(C_6H_5)_3)_4$ is preferred.

The compounds of the general formulae (II-III) and (II-V) are known or can be prepared by customary methods.

The compounds of the general formula (II-II) are known in some cases and can be prepared by a process in which compounds of the general formula (II-VI)

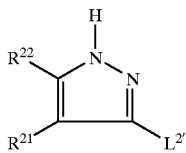

(II-VI)

in which $R^{21}$ and $R^{22}$ have the abovementioned meaning and $L^{2'}$ has the abovementioned meaning of $L^2$ and is identical to or different from this, are reacted with compounds of the general formula (II-V) analogously to the abovementioned process [B2].

The compounds of the general formula (II-IV) are known in some cases or, in the case of the stannyls, are new and can then be prepared, for example, by a process in which compounds of the general formula (II-IVa)

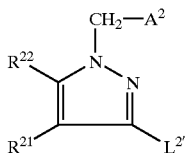

(II-IVa)

in which $R^{21}$, $R^{22}$ and $A^2$ have the abovementioned meaning, and $L^{2-}$ represents triflate or halogen, preferably iodine, are reacted with compounds of the general formula (II-VII)

$(SnR^{36}R^{37}R^{38})_2$ (II-VII)

in which $R^{36}$, $R^{37}$ and $R^{38}$ have the abovementioned meaning, under palladium catalysis, as described above.

The compounds of the general formula (II-VII) are known or can be prepared by customary methods.

The compounds of the general formula (II-IVa) are new in most cases and can be prepared by a process in which compounds of the general formula (II-VIII)

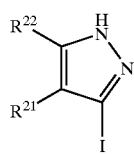

(II-VIII)

in which $R^{21}$ and $R^{22}$ have the abovementioned meaning, are reacted with the abovementioned compounds of the general formula (II-V)

 $R^{20}$—$T^2$ (II-V)

wherein $R^{20}$ and $T^2$ have the abovementioned meaning, in one of the abovementioned solvents, preferably tetrahydrofuran, and in the presence of sodium hydride in a temperature range from 0° C. to 40° C., preferably at room temperature and under an inert gas atmosphere.

The compounds of the general formula (II-VIII) are known in most cases or can be prepared by customary methods.

The reductions are in general carried out with reducing agents, preferably with those which are suitable for reduction of carbonyl to hydroxy compounds. A particularly suitable reduction here is reduction with metal hydrides or complex metal hydrides in inert solvents, if appropriate in the presence of a trialkylborane. The reduction is preferably carried out with complex metal hydrides, such as, for example, lithium boranate, sodium boranate, potassium boranate, zinc boranate, lithium trialkylhydrido-boranate, diisobutylaluminium hydride or lithium aluminium hydride. The reduction is especially preferably carried out with diisobutylaluminium hydride and sodium borohydride.

The reducing agent is in general employed in an amount of 1 mol to 6 mol, preferably 1 mol to 4 mol, per mole of the compounds to be reduced.

The reduction in general proceeds in a temperature range from −78° C. to +50° C., preferably from −78° C. to 0° C., in the case of DIBAH, 0° C., room temperature in the case of $NaBH_4$, particularly preferably at −78° C, in each case depending on the choice of reducing agent and solvents.

The reduction in general proceeds under normal pressure, but it is also possible to carry it out under increased or reduced pressure.

In the case where the radicals of the formulae —$S(O)_{c2}NR^{31'}R^{32'}$ and —$S(O)c_{2'}NR^{31'}R^{32'}$ are substituted, the corresponding unsubstituted compounds are first reacted with thionyl chloride and reacted with the amines in the presence of the abovementioned ethers, preferably dioxane, in a second step and in the case where c2=2, oxidation by customary methods is subsequently carried out. The reactions are carried out in general in a temperature range from 0° C. to 70° C. under normal pressure.

The protective group is in general split off in one of the abovementioned alcohols and/or THF or acetone, preferably methanol/THF, in the presence of hydrochloric acid or trifluoroacetic acid or toluenesulphonic acid in a temperature range from 0° C. to 70° C., preferably at room temperature under normal pressure.

The invention moreover relates to the combination of the compounds of the general formula (II-I) according to the invention with organic nitrates and NO donors.

Organic nitrates and NO donors in the context of the invention are in general substances which display their therapeutic action via the liberation of NO or NO species. Sodium nitroprusside (SNP), nitroglycerol, isosorbide dinitrate, isosorbide mononitrate, molsidomine and SIN-1 are preferred.

The invention also relates to the combination with compounds which inhibit the breakdown of cyclic guanosine monophosphate (cGMP). These are, in particular, inhibitors of phosphodiesterases 1, 2 and 5; nomenclature according to Beavo and Reifsnyder (1990) TIPS 11 pages 150–155. The action of the compounds according to the invention is potentiated and the desired pharmacological effect increased by these inhibitors.

The compounds of the general formula (II-I) according to the invention show an unforeseeable, valuable pharmacological action spectrum.

The compounds of the general formula (II-I).according to the invention lead to a vessel relaxation/inhibition of platelet aggregation and to a lowering of blood pressure, as well as to an increase in coronary blood flow. These actions are mediated via direct stimulation of soluble guanylate cyclase and an intracellular increase in cGMP. Furthermore, the compounds according to the invention intensify the action of substances which increase the cGMP level, such as, for example, EDRF (endothelium derived relaxing factor), NO donors, protoporphyrin IX, arachidonic acid or phenylhydrazine derivatives.

They can therefore be employed in medicaments for treatment of cardiovascular diseases, such as, for example, for treatment of high blood pressure and cardiac insufficiency, stable and unstable angina. pectoris and peripheral and cardiac vascular diseases and of arrhythmias, for treatment of thromboembolic diseases and ischaemias, such as myocardial infarction, cerebral stroke, transitory and ischaemic attacks and peripheral circulatory disturbances, for preventing restenoses, such as after thrombolysis treatment, percutaneous transluminal angioplasties (PTA), percutaneous transluminal coronary angioplasties (PTCA) and bypass, and for treatment of arteriosclerosis and diseases of the urogenital system, such as, for example, prostate hypertrophy, erectile dysfunction and incontinence.

The following investigations were carried out to determine the cardiovascular actions: the influence on guanylate cyclase-dependent cGMP formation with and without an NO donor was tested in investigations in vitro on cells of vascular origin. The anti-aggregatory properties were demonstrated on human platelets stimulated with collagen.

The vessel-relaxing action was determined on rabbit aortic rings precontracted with phenylephrine. The antihypertensive action was investigated on anaesthetized rats.

Stimulation of Soluble Guanylate Cyclase in Primary Endothelial Cells

Primary endothelial cells were isolated from pig aortas by treatment with collagenase solution. The cells were then cultured in a culture medium until confluence was reached. For the investigations, the cells were subjected to passaging, sown in cell culture plates and subcultured until confluence was reached. To stimulate the endothelial guanylate cyclase, the culture medium was sucked off and the cells were washed once with Ringer's solution and incubated in stimulation buffer with or without an NO donor (sodium nitroprusside, SNP, 1 $\mu$M). Thereafter, the test substances (final concentration 1 $\mu$M) were pipetted onto the cells. At the end of the 10-minute incubation period, the buffered solution was sucked off and the cells were lysed at −20° C. for 16 hours. The intracellular cGMP was then determined radioimmunologically.

TABLE A

| Example No. | % increase in cGMP |
| --- | --- |
| II-36 | 225 |
| II-38 | >1000 |
| II-39 | 909 |
| II-40 | >1000 |
| II-41 | 557 |
| II-42 | 611 |
| II-43 | >1000 |
| II-44 | >1000 |
| II-45 | 326 |
| II-46 | 390 |
| II-47 | 240 |
| II-48 | >1000 |
| II-49 | >1000 |
| II-50 | 116 |
| II-52 | 397 |
| II-53 | 428 |
| II-56 | 233 |
| II-58 | 271 |
| II-59 | 268 |

Vessel-relaxing Action in Vitro

Rings 1.5 mm wide of an aorta isolated from a rabbit are introduced individually, under pretension, in 5 ml organ baths with Krebs-Henseleit solution warmed to 37° C. and gassed with carbogen. The contraction force is amplified and digitalized and recorded in parallel on a line recorder. To generate a contraction, phenylephrine is added cumulatively to the bath in an increasing concentration.

After several control cycles, the substance to be investigated is investigated in each further pass in each case in an increasing dosage, and a comparison is made with the level of the contraction achieved in the last preliminary pass. The concentration necessary to reduce the level of the control value by 50% ($IC_{50}$) is calculated from this. The standard application volume is 5 $\mu$l.

TABLE B

| Example No. | Aorta $IC_{50}$ ($\mu$m) |
| --- | --- |
| II-36 | 13 |
| II-39 | 11 |
| II-40 | 24 |
| II-41 | 13 |
| II-42 | 10 |
| II-38 | 11 |
| II-48 | 13 |
| II-49 | 65 |
| II-50 | >>31 |
| II-51 | >>30 |
| II-52 | 14 |
| II-53 | 18 |
| II-55 | >35 |
| II-56 | >33 |
| II-59 | >33 |
| II-60 | >30 |
| II-61 | >30 |
| II-62 | 13 |

Blood Pressure Measurements on Anaesthetized Rats

Male Wistar Rats with a body weight of 300–350 g are anaesthetized with thiopental (100 mg/kg i.p.). After tracheotomy, a catheter is inserted into the femoral artery for blood pressure measurement. The substances to be tested are administered orally by means of a stomach tube in various doses as a suspension in tylose solution.

Inhibition of Platelet Aggregation in Vitro

To determine the platelet aggregation-inhibiting action, blood from healthy subjects of both sexes was used. One part of 3.8% strength aqueous sodium citrate solution was admixed to 9 parts of blood as an anticoagulant. Platelet-richer citrate plasma (PRP) is obtained from this blood by means of centrifugation.

For these investigations, 445 μl of PRP and 5 μl of the active compound solution were preincubated in a water-bath at 37° C. The platelet aggregation was then determined by the turbidometric method in an aggregometer at 37° C. For this, 50 μl of collagen, an aggregation-inducing agent, were added to the preincubated sample and the change in optical density was recorded. For the quantitative evaluation, the maximum aggregation response was determined and the percentage inhibition compared with the control was calculated therefrom.

The compounds described in the present invention in embodiment II are also active compounds for combating diseases in the central nervous system which are characterized by impairments of the NO/cGMP system. In particular, they are suitable for eliminating cognitive deficits, for improving learning and memory performance and for treatment of Alzheimer's disease. They are also suitable for treatment of diseases of the central nervous system such as states of anxiety, stress and depression, sexual dysfunctions of central nervous origin and sleep disturbances, and for regulating pathological disturbances in the intake of food and addictive substances.

These active compounds are furthermore also suitable for regulation of cerebral circulation and are therefore effective agents for combating migraine.

They are also suitable for prophylaxis and combating the consequences of cerebral infarction events (apoplexia cerebri), such as apoplexy, cerebral ischaemias and craniocerebral trauma. The compounds according to the invention can also be employed for combating states of pain.

The present invention includes pharmaceutical formulations which comprise, in addition to non-toxic, inert pharmaceutically suitable carriers, one or more compounds according to the invention, or which consist of one or more active compounds according to the invention, and processes for the preparation of these formulations.

If appropriate, the active compound or compounds can also be present in microencapsulated form in one or more of the abovementioned carriers.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also comprise further pharmaceutical active compounds in addition to the compounds according to the invention.

In general, it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, to achieve the desired results. An individual dose preferably comprises the active compound or compounds according to the invention in amounts of about 1 to about 80, in particular 3 to 30 mg/kg of body weight.

| | |
|---|---|
| Me = | methyl |
| OMe = | methoxy |
| Et = | ethyl |
| OEt = | ethoxy |
| Ph = | phenyl |

III

The present invention relates to new 3-heterocyclyl-substituted pyrazole derivatives, in the embodiment designated III (roman three) of the general formula (III-I)

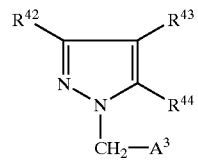

(III-I)

in which
R$^{42}$ represents a saturated 6-membered heterocyclic ring having up to 2 heteroatoms from the series consisting of S, N and/or O or represents a 5-membered aromatic or saturated heterocyclic ring having 2 to 3 heteroatoms from the series consisting of S, N and/or O, which can also be bonded via a nitrogen atom and which are optionally substituted up to 3 times in an identical or different manner by formyl, phenyl, mercaptyl, carboxyl, trifluoromethyl, hydroxyl, straight-chain or branched acyl, alkoxy, alkylthio or alkoxycarbonyl having in each case up to 6 carbon atoms, nitro, cyano, halogen, phenyl or straight-chain or branched alkyl having up to 6 carbon atoms, which in its turn can be substituted by hydroxyl, halogen, trifluoromethyl, amino, carboxyl, straight-chain or branched acyl, alkoxy, alkoxycarbonyl or acylamino having in each case up to 5 carbon atoms or by a radical of the formula —OR$^{45}$, wherein
R$^{45}$ denotes straight-chain or branched acyl having up to 5 carbon atoms or a group of the formula —SiR$^{46}$R$^{47}$R$^{48}$, wherein
R$^{46}$, R$^{47}$ and R$^{48}$ are identical or different and denote aryl having 6 to 10 carbon atoms or alkyl having up to 6 carbon atoms,
and/or can be substituted by a radical of the formula

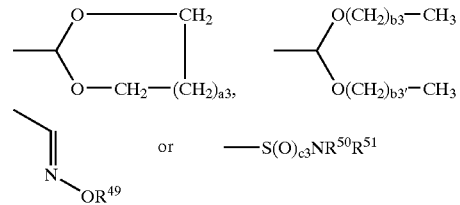

wherein
a3, b3 and b3' denote the number 0, 1, 2 or 3,
R$^{49}$ denotes hydrogen or straight-chain or branched alkyl having up to 4 carbon atoms,
c3 denotes the number 1 or 2 and
R$^{50}$ and R$^{51}$ are identical or different and denote hydrogen or straight-chain or branched alkyl having up to 10 carbon atoms, which is optionally substituted by cycloalkyl having 3 to 8 carbon atoms or by aryl having 6 to 10 carbon atoms, which in its turn can be substituted by halogen, or
denote aryl having 6 to 10 carbon atoms, which is optionally substituted by halogen, or denote cycloalkyl having 3 to 7 carbon atoms, or $R^{50}$ and $R^{51}$, together with the nitrogen atom, form a 5- to 7-membered saturated heterocyclic ring, which can optionally contain a further oxygen atom or a radical —$NR^{52}$, wherein $R^{52}$ denotes hydrogen, straight-chain or branched alkyl having up to 4 carbon atoms or a radical of the formula

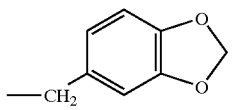

or denotes benzyl or phenyl, wherein the ring systems are optionally substituted by halogen, $R^{43}$ and $R^{44}$, including the double bond, form a 5-membered aromatic heterocyclic ring having one heteroatom from the series consisting of N, S and/or O, or a phenyl ring, which are optionally substituted up to 3 times in an identical or different manner by formyl, carboxyl, hydroxyl, amino, straight-chain or branched acyl, alkoxy or alkoxycarbonyl having in each case up to 6 carbon atoms, nitro, cyano, halogen, phenyl or straight-chain or branched alkyl having up to 6 carbon atoms, which in its turn can be substituted by hydroxyl, amino, carboxyl, straight-chain or branched acyl, alkoxy or alkoxycarbonyl having in each case up to 5 carbon atoms, and/or are optionally substituted by a group of the formula —$S(O)_{c3'}NR^{50'}R^{51'}$, wherein c3', $R^{50'}$ and $R^{51'}$ have the abovementioned meaning of c3, $R^{50}$ and $R^{51}$ and are identical to or different from these, $A^3$ represents a 5- to 6-membered aromatic or saturated heterocyclic ring having up to 3 heteroatoms from the series consisting of S, N and/or O, or phenyl, which are optionally substituted up to 3 times in an identical or different manner by amino, mercaptyl, hydroxyl, formyl, carboxyl, straight-chain or branched acyl, alkylthio, alkyloxyacyl, alkoxy or alkoxycarbonyl having in each case up to 6 carbon atoms, nitro, cyano, trifluoromethyl, azido, halogen, phenyl or straight-chain or branched alkyl having up to 6 carbon atoms, which in its turn can be substituted by hydroxyl, carboxyl, straight-chain or branched acyl, alkoxy or alkoxycarbonyl having in each case up to 5 carbon atoms, and/or is substituted by a group of the formula —(CO)$_{d3}$—$NR^{53}R^{54}$, wherein d3 denotes the number 0 or 1, $R^{53}$ and $R^{54}$ are identical or different and denote hydrogen, phenyl, benzyl or straight-chain or branched alkyl or acyl having in each case up to 5 carbon atoms, and their isomeric forms and salts.

The compounds of the general formula (III-I) according to the invention can also be present in the form of their salts with organic or inorganic bases or acids.

In the context of embodiment III of the present invention, physiologically acceptable salts are preferred. Physiologically acceptable salts of the compounds according to the invention can be salts of the substances according to the invention with mineral acids, carboxylic acids or sulphonic acids. Particularly preferred salts are, for example, salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred salts are, for example, sodium, potassium, magnesium or calcium salts, and ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms which either behave as mirror images (enantiomers) or do not behave as mirror images (diastereomers). The invention relates both to the enantiomers or diastereomers or their particular mixtures. The racemic forms, like the diastereomers, can be separated into the stereoisomerically uniform constituents in a known manner.

Heterocyclic ring in the context of embodiment III of the invention in general, depending on the abovementioned substituents, represents a saturated or aromatic 5- or 6-membered heterocyclic ring, which can contain 1, 2 or 3 heteroatoms from the series consisting of S, N and/or O and, in the case of a nitrogen atom, can also be bonded via this. Examples which may be mentioned are: oxadiazolyl, thiadiazolyl, pyrazolyl, pyrimid pyridyl, thienyl, furyl, pyrrolyl, tetrahydropyranyl, tetrahydrofuranyl, 1,2,3-triazolyl, thiazolyl, oxazolyl, imidazolyl, morpholinyl or piperidyl. Oxazolyl, thiazolyl, pyrazolyl, pyrimidyl, pyridyl or tetrahydropyranyl are preferred.

Preferred compounds of the general formula (III-I) according to the invention are those in which $R^{42}$ represents imidazolyl, oxazolyl, thiazolyl, 1,2,3-triazolyl, pyrazolyl, oxadiazolyl, thiadiazolyl, isoxazolyl, isothiazolyl, pyranyl or morpholinyl, which are optionally substituted up to twice in an identical or different manner by formyl, trifluoromethyl, phenyl, carboxyl, hydroxyl, straight-chain or branched acyl, alkoxy or alkoxycarbonyl having in each case up to 5 carbon atoms, nitro, cyano, azido, fluorine, chlorine, bromine, phenyl or straight-chain or branched alkyl having up to 5 carbon atoms, which in its turn can be substituted by hydroxyl, halogen, trifluoromethyl, amino, carboxyl, straight-chain or branched acyl, alkoxy, alkoxycarbonyl or acylamino having in each case up to 4 carbon atoms, or by a radical of the formula —$OR^{45}$, wherein $R^{45}$ denotes straight-chain or branched acyl having up to 4 carbon atoms or a group of the formula —$SiR^{46}R^{47}R^{48}$, wherein $R^{46}$, $R^{47}$ and $R^{48}$ are identical or different and denote straight-chain or branched alkyl having up to 4 carbon atoms, and/or are substituted by a radical of the formula

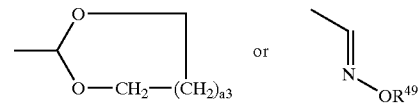

wherein a3 denotes the number 0, 1, 2 or 3, $R^{49}$ denotes hydrogen or straight-chain or branched alkyl having up to 3 carbon atoms, $R^{43}$ and $R^{44}$, including the double bond, form a furyl, thienyl or phenyl ring, which are optionally substituted up to 3 times in an identical or different manner by formyl, carboxyl, hydroxyl, amino, straight-chain or branched acyl, alkoxy or alkoxycarbonyl having in each case up to 5 carbon atoms, nitro, cyano, azido, fluorine, chlorine, bromine, phenyl or straight-chain or branched alkyl having up to 5 carbon atoms, which in its turn can be substituted by hydroxyl, amino, carboxyl, straight-chain or branched acyl, alkoxy or alkoxycarbonyl having in each case up to 4 carbon atoms, $A^3$ represents tetrahydropyranyl, tetrahydrofuranyl, thienyl, phenyl, morpholinyl, pyrimidyl, pyridazinyl or pyridyl, which are optionally substituted up to twice in an identical or different manner by. hydroxyl, formyl, carboxyl, straight-chain or branched acyl, alkylthio, alkyloxyacyl, alkoxy or alkoxycarbonyl having in each case up to 4 carbon atoms, fluorine, chlorine, bromine, nitro, cyano, trifluoromethyl or straight-chain or branched alkyl having up to 4 carbon atoms, which in its turn can be substituted by hydroxyl, carboxyl, straight-chain or branched acyl, alkoxy or alkoxycarbonyl having in each case up to 4 carbon atoms, and/or are substituted by a group of the formula —(CO)$_{d3}$—NR$^{53}$R$^{54}$, wherein d3 denotes the number 0 or 1, R$^{53}$ and R$^{54}$ are identical or different and denote hydrogen, phenyl, benzyl or straight-chain or branched alkyl or acyl having in each case up to 4 carbon atoms, and their isomeric forms and salts.

Particularly preferred compounds of the general formula (III-I) according to the invention are those in which R$^{42}$ represents imidazolyl, oxazolyl, oxadiazolyl or thiazolyl, which are optionally substituted up to twice in an identical or different manner by formyl, trifluoromethyl, phenyl, straight-chain or branched acyl, alkoxy or alkoxycarbonyl having in each case up to 4 carbon atoms or straight-chain or branched alkyl having up to 4 carbon atoms, which in its turn can be substituted by hydroxyl, fluorine, chlorine, trifluoromethyl, carboxyl, amino, straight-chain or branched acyl, alkoxy, alkoxycarbonyl or acylamino having in each case up to 3 carbon atoms or by the radical of the formula —O—CO—CH$_3$, and/or are substituted by a radical of the formula

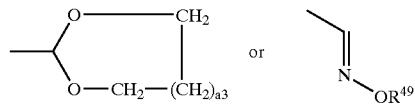 or 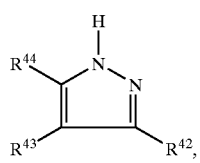

wherein a3 denotes the number 0, 1 or 2,

R$^{49}$ denotes hydrogen or methyl,

R$^{43}$ and R$^{44}$, including the double bond, form a furyl, thienyl or phenyl ring, which are optionally substituted up to twice in an identical or different manner by formyl, carboxyl, hydroxyl, amino, straight-chain or branched acyl, alkoxy or alkoxycarbonyl having in each case up to 4 carbon atoms, nitro, cyano, fluorine, chlorine, phenyl or straight-chain or branched alkyl having up to 3 carbon atoms, which in its turn can be substituted by hydroxyl, amino, carboxyl, straight-chain or branched acyl, alkoxy or alkoxycarbonyl having in each case up to 3 carbon atoms, $A^3$ represents tetrahydropyranyl, phenyl, thienyl, pyrimidyl or pyridyl, which are optior substituted up to twice in an identical or different manner by formyl, carboxyl, straight-chain or branched acyl, alkylthio, alkyloxyacyl, alkoxy or alkoxycarbonyl having in each case up to 3 carbon atoms, fluorine, chlorine, bromine, nitro, cyano, trifluoromethyl, or straight-chain or branched alkyl having up to 3 carbon atoms, which in its turn can be substituted by hydroxyl, carboxyl, straight-chain or branched acyl, alkoxy or alkoxycarbonyl having in each case up to 3 carbon atoms, and/or are substituted by a group of the formula —(CO)$_{d3}$—NR$^{53}$R$^{54}$, wherein d3 denotes the number 0 or 1, R$^{53}$ and R$^{54}$ are identical or different and denote hydrogen or straight-chain or branched alkyl or acyl having in each case up to 3 carbon atoms, and their isomeric forms and salts.

Especially preferred compounds of the general formula (III-I) according to the invention are those in which R$^{42}$ represents imidazolyl, oxazolyl, thiazolyl or oxadiazolyl, which are optionally substituted up to twice in an identical or different manner by ethoxycarbonyl, phenyl or by methyl or ethyl, wherein the alkyl radicals in their turn can be substituted by hydroxyl, chlorine, ethoxycarbonyl, oxycarbonylmethyl or methoxy, R$^{43}$ and R$^{44}$ together, in changing the double bond, represent phenyl, which is optionally substituted by nitro, $A^3$ represents phenyl or phenyl which is substituted by fluorine, or pyrimidyl and their isomers and salts.

The invention furthermore relates to processes for the preparation of the compounds of the general formula (III-I) according to the invention, characterized in that

[A3] compounds of the general formula (III-I)

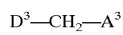

(III-II)

in which

R$^{42}$, R$^{43}$ and R$^{44}$ have the abovementioned meaning, are reacted with compounds of the general formula (III-III)

$$D^3—CH_2—A^3 \qquad (III-III)$$

in which $A^3$ has the abovementioned meaning and $D^3$ represents triflate or halogen, preferably bromine, in inert solvents, if appropriate in the presence of a base, or

[B3] compounds of the general formula (III-IV)

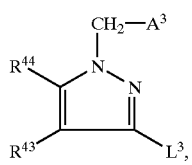
(III-IV)

in which

A$^3$, R$^{43}$ and R$^{44}$ have the abovementioned meaning and
L$^3$ represents a radical of the formula —SnR$^{55}$R$^{56}$R$^{57}$, ZnR$^{58}$, iodine, bromine or triflate, wherein
R$^{55}$, R$^{56}$ and R$^{57}$ are identical or different and denote straight-chain or branched alkyl having up to 4 carbon atoms and
R$^{58}$ denotes halogen, are reacted with compounds of the general formula (III-V)

R$^{42}$—T$^3$ (III-V), in which

R$^{42}$ has the abovementioned meaning and
in the case where L$^3$=SnR$^{55}$R$^{56}$R$^{57}$ or ZnR$^{58}$,
T$^3$ represents triflate or represents halogen, preferably bromine, and
in the case where L$^3$=iodine, bromine or triflate,
T$^3$ represents a radical of the formula SnR$^{55}$R$^{56}$R$^{57}$, ZnR$^{58}$ or BR$^{59}$R$^{60}$, wherein
R$^{55'}$, R$^{56'}$, R$^{57'}$ and R$^{58'}$ have the abovementioned meaning of R$^{55}$, R$^{56}$, R$^{57}$ and R$^{58}$ and are identical to or different from these, and
R$^{59}$ and R$^{60}$ are identical or different and denote hydroxyl, aryloxy having 6 to 10 carbon atoms or straight-chain or branched alkyl or alkoxy having in each case up to 5 carbon atoms, or together form a 5- or 6-membered carbocyclic ring,
in a palladium-catalysed reaction in inert solvents, or

[C3] in the case where

R$^{42}$ = 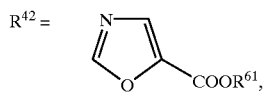

in which

R$^{61}$ represents straight-chain or branched alkyl having up to 4 carbon atoms, compounds of the general formula (III-VI)

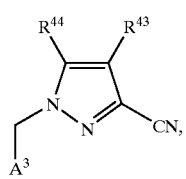
(III-VI)

in which

A$^3$, R$^{43}$ and R$^4$ have the abovementioned meaning,
are reacted with diazo compounds of the general formula (III-VII)

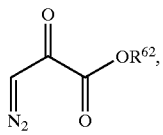
(III-VII)

in which

R$^{62}$ represents straight-chain or branched alkyl having up to 4 carbon atoms, in the presence of copper salts or rhodium salts to give compounds of the general formula (III-Ia)

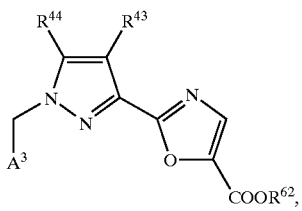
(III-Ia)

in which

A$^3$, R$^{43}$, R$^{44}$ and R$^{62}$ have the abovementioned meaning,

[D3] in the case where R$^{42}$=

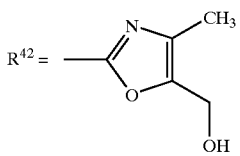

compounds of the general formula (III-VIII)

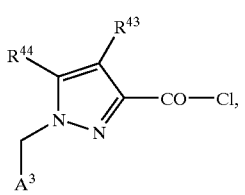
(III-VIII)

in which

A$^3$, R$^{43}$ and R$^{44}$ have the abovementioned meaning,
are either converted directly by reaction with the compound of the formula (III-IX)

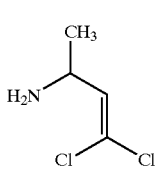
(III-IX)

in the system NaOCO—CH$_3$/N-methylpyrrolidine into the compounds of the general formula (III-Ib)

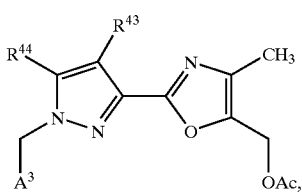
(III-Ib)

in which $R^{43}$, $R^{44}$ and $A^3$ have the abovementioned meaning, and the acetyl group is then split off by the action of potassium hydroxide in methanol, or by reaction of the compounds of the general formula (III-VIII) with the compound of the formula (III-IX), the compounds of the general formula (III-X)

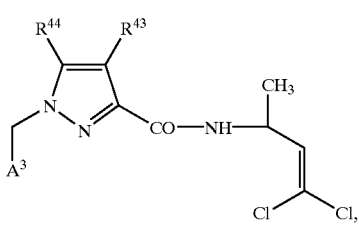
(III-X)

in which $R^{43}$, $R^{44}$ and $A^3$ have the abovementioned meaning, are first prepared, and the hydroxymethyl compounds are prepared in a further step by the action of potassium hydroxide, and, if appropriate, are converted into the corresponding alkoxy compounds by an alkylation by customary methods, or

[E3] compounds of the general formula (III-XI)

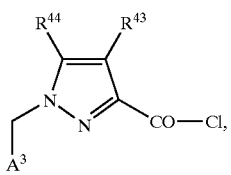
(III-XI)

in which $A^3$, $R^{43}$ and $R^{44}$ have the abovementioned meaning, by reaction with the compound of the formula (III-XII)

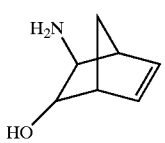
(III-XII)

the compounds of the general formula (III-XIII)

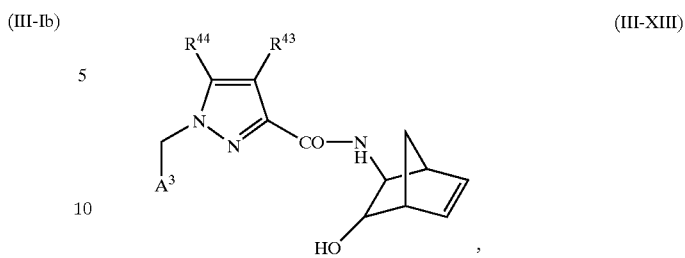
(III-XIII)

in which $A^3$, $R^{43}$ and $R^{44}$ have the abovementioned meaning, are prepared, and are then reacted in the context of a retro-Diels-Alder reaction (cf. J. Org. Chem, 988, 58, 3387–90), or

[F3] compounds of the general formula (III-XIV)

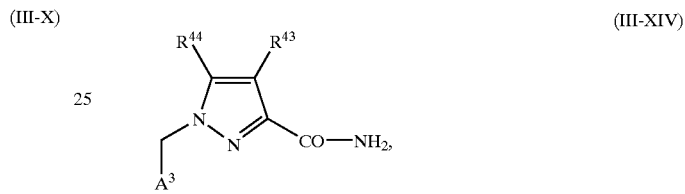
(III-XIV)

in which $A^3$, $R^{43}$ and $R^{44}$ have the abovementioned meaning, are reacted with compounds of the general formula (III-XV)

Br—$CH_2$—CO—$R^{63}$ (III-XV), in which $R^{63}$ denotes straight-chain or branched alkyl or alkoxycarbonyl having in each case up to 4 carbon atoms, in inert solvents to give the compounds of the general formula (III-Ic)

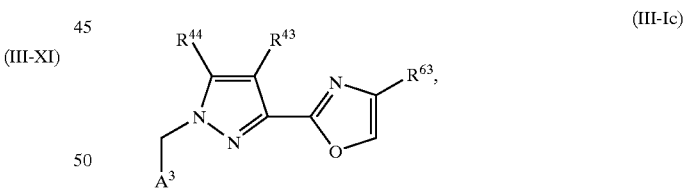
(III-Ic)

in which $A^3$, $R^{43}$, $R^{44}$ and $R^{63}$ have the abovementioned meaning (cf. Oxazoles, J. Wiley/New York, 1986, page 11/12), and, in the case of the esters ($R^{63}$=$CO_2$—($C_1$-$C_4$-alkyl), a reduction is carried out by customary methods to give the corresponding hydroxymethyl compounds, or

[G3] in the case where $R^{42}$=

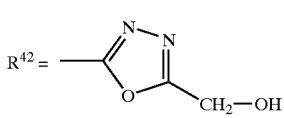

carboxylic acids of the general formula (III-XVI)

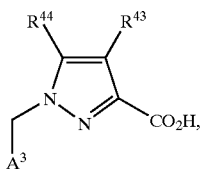
(III-XVI)

in which
A³, R⁴³ and R⁴⁴ have the abovementioned meaning,
are first converted with hydrazine hydrate into the compounds of the general formula (III-XVII)

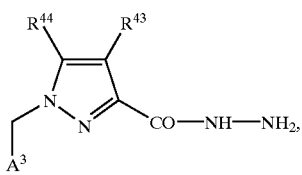
(III-XVII)

in which
A³, R⁴³ and R⁴⁴ have the abovementioned meaning,
in a further step, with the compound of the formula (III-XVIII)

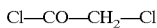 (III-XVIII)

the compounds of the general formula (III-XIX)

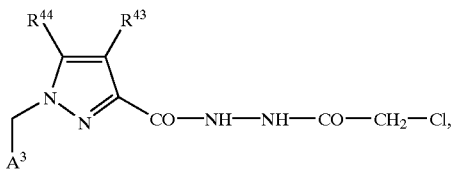
(III-XIX)

in which
A³, R⁴³ and R⁴⁴ have the abovementioned meaning,
are prepared
then under the action of phosphorus oxytrichloride, cyclization is carried out to give the compounds of the general formula (III-Id)

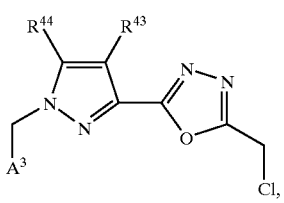
(III-Id)

in which
A³, R⁴³ and R⁴⁴ have the abovementioned meaning,
and, as already described above, the —CH₂—OH-substituted compounds are prepared via the stage of the corresponding —CH₂—O—CO—CH₃-substituted compounds (cf. Arzn. Forsch. 45 (1995) 10, 1074–1078), or
[H3] in the case where R⁴² represents a radical of the formula

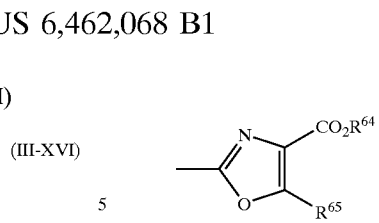

wherein
R⁶⁴ denotes hydrogen or straight-chain or branched alkyl having up to 4 carbon atoms and
R⁶⁵ has the scope of meaning of the secondary substituents listed above under the heterocyclic radical R⁴²,
compounds of the general formula (III-XX)

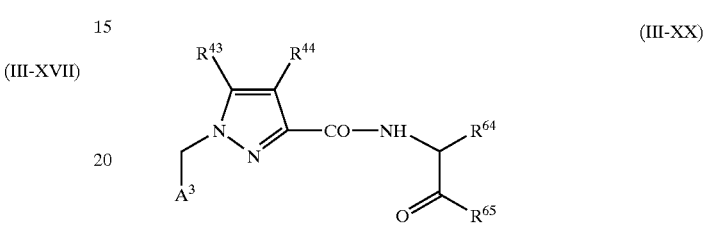
(III-XX)

in which
A³, R⁴³, R⁴⁴, R⁶⁴ and R⁶⁵ have the abovementioned meaning,
are reacted in the system PPh₃/I₂ in the presence of a base, preferably with triethylamine, or
[I3] in the case where R⁴² represents a radical of the formula

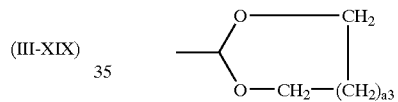

wherein a3 has the abovementioned meaning,
compounds of the general formula (III-XXI)

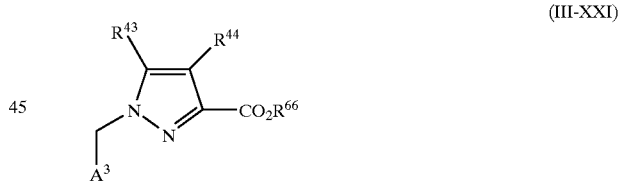
(III-XXI)

in which
A³, R⁴³ and R⁴⁴ have the abovementioned meaning and
R⁶⁶ has the abovementioned meaning of R⁶⁴ and is identical to or different from this,
either are first converted by reduction by customary methods into the compounds of the general formula (III-XXII)

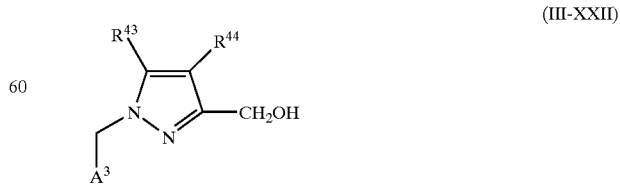
(III-XXII)

in which
A³, R⁴³ and R⁴⁴ have the abovementioned meaning, and the compounds of the general formula (III-XXIII)

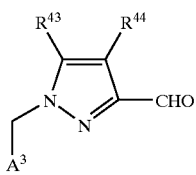

(III-XXIII)

in which
A³, R⁴³ and R⁴⁴ have the abovementioned meaning,
are then prepared by oxidation, or
the compounds of the general formula (III-XXI) are converted directly by reduction into the compounds of the general formula (III-XXIII),
and, finally, these are reacted with 1,2- or 1,3-dihydroxy compounds by conventional methods, or

[J3] in the case where $R^{42}$ represents the radical of the formula

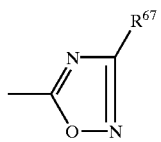

wherein
$R^{67}$ has the abovementioned meaning of $R^{65}$ and is identical to or different from this,
either compounds of the general formula (III-XXIV)

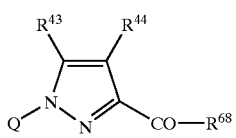

(III-XXIV)

in which
$R^{43}$ and $R^{44}$ have the abovementioned meaning and
Q represents hydrogen or represents the —CH₂—A³ radical and
$R^{68}$ represents halogen or straight-chain or branched alkoxy having up to 4 carbon atoms, preferably chlorine, methoxy or ethoxy,
are reacted with compounds of the general formula (III-XXV)

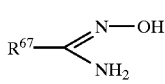

(III-XXV)

in which
$R^{67}$ has the abovementioned meaning, if appropriate in the presence of a base, and, in the case where Q=H, the products are then reacted with compounds of the general formula A³—CH₂—Br (III-XXVI), in which A has the abovementioned meaning, or compounds of the general formula (III-XXVII)

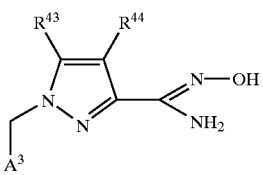

(III-XXVII)

in which

A³, R⁴³ and R⁴⁴ have the abovementioned meaning are reacted with compounds of the general formula (III-XXVIII)

R⁶⁷'—CO—R⁶⁸'       (III-XXVIII)

in which $R^{67'}$ has the abovementioned meaning of $R^{67}$ and is identical to or different from this and $R^{68'}$ has the abovementioned meaning of $R^{68}$ and is identical to or different from this, if appropriate in the presence of a base, and, in the case of the radicals —S(O)$_{c3}$NR⁵⁰R⁵¹ and —S(O)$_{c3'}$NR⁵⁰'R⁵¹' starting from the unsubstituted compounds of the general formula (III-I), a reaction first with thionyl chloride and finally with the amine component is carried out, and, if appropriate, the substituents listed under R⁴², R⁴³, R⁴⁴ and/or A³ are varied or introduced by customary methods, preferably by reduction, oxidation, splitting off of protective groups and/or nucleophilic substitution.

The processes according to the invention described above can be explained by way of example by the following equations:

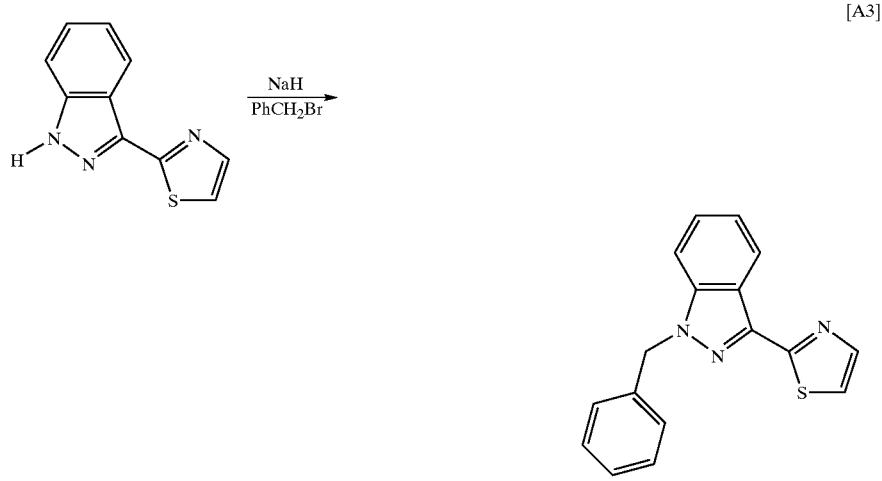
[A3]
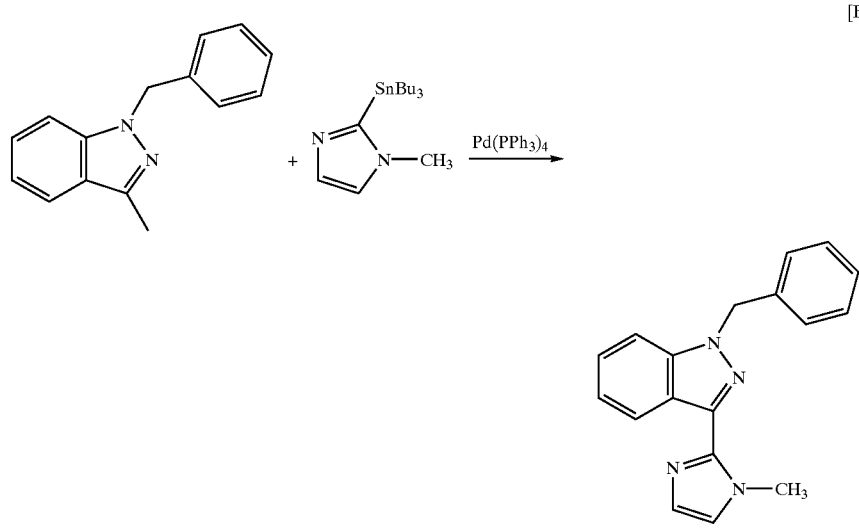
[B3]
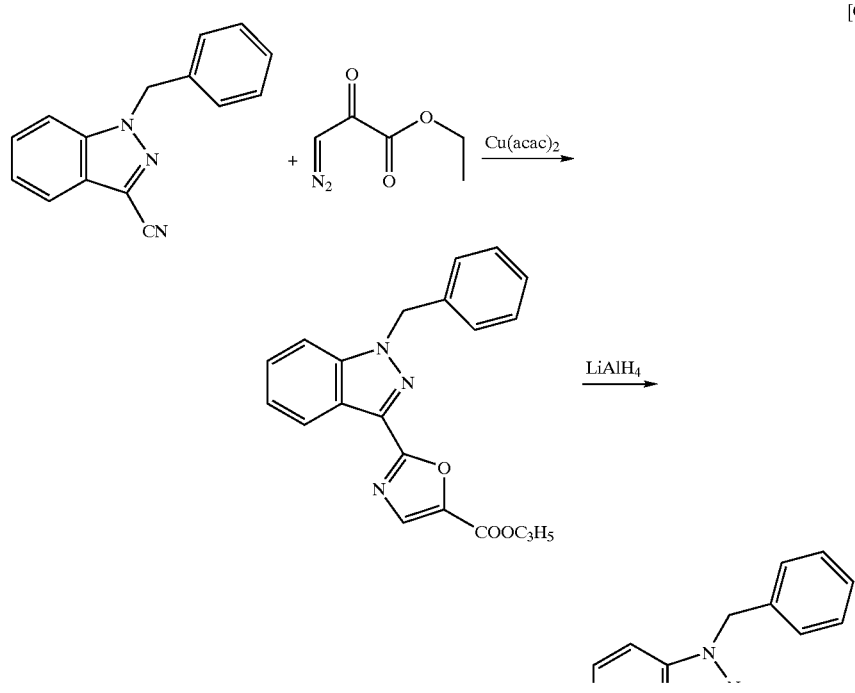
[C3]

Suitable solvents here for the individual steps of process [A3] are inert organic solvents which do not change under the reaction conditions. These include ethers, such as diethyl ether or tetrahydrofuran, hydrocarbons, such as benzene, xylene, toluene, hexane, cyclohexane or petroleum fractions, nitromethane, dimethylformamide, acetone, acetonitrile or hexamethylphosphoric acid triamide. It is also possible to employ mixtures of the solvents. Tetrahydrofuran, toluene or dimethylformamide are particularly preferred.

Bases which can be employed for the process according to the invention are in general inorganic or organic bases. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or alkali metal or alkaline earth metal alcoholates, such as sodium or potassium methanolate, sodium or potassium ethanolate or potassium tert-butylate, or organic amines (trialkyl-($C_1$–$C_6$)-amines), such as triethylamine, or heterocyclic compounds, such as 1,4-diazabicyclo[2.2.2]octane (DABCO), 1,8-diazabicyclo-[5.4.0]undec-7-ene (DBU), pyridine, diaminopyridine, N-methylpyrrolidone methylpiperidine or morpholine. It is also possible to employ as the bases alkali metals, such as sodium, and hydrides thereof, such as sodium hydride. Sodium carbonate and potassium carbonate, triethylamine, sodium hydride and N-methylpyrrolidone are preferred.

The base is employed in an amount of 1 mol to 5 mol, preferably 1 mol to 3 mol, per mole of the compound of the general formula (III-II).

The reaction is in general carried out in a temperature range from 0° C. to 150° C., preferably from +20° C. to +110° C.

The reaction can be carried out under normal, increased or reduced pressure (for example 0.5 to 5 bar). It is in general carried out under normal pressure.

Suitable solvents here for process [B3] are inert organic solvents which do not change under the reaction conditions. These include ethers, such as diethyl ether or tetrahydrofuran, DME or dioxane, halogenohydrocarbons, such as methylene chloride, chloroform, carbon tetrachloride, trichloroethane, tetrachloroethane, 1,2-dichloroethane or trichloroethylene, hydrocarbons, such as benzene, xylene, toluene, hexane, cyclohexane, or petroleum fractions, nitromethane, dimethylformamide, acetone, acetonitrile or hexamethylphosphoric acid triamide. It is also possible to employ mixtures of the solvents. Tetrahydrofuran, dimethylformamide, toluene, dioxane or dimethoxyethane are particularly preferred.

The reaction is in general carried out in a temperature range from 0° C. to 150° C., preferably from +20° C. to +110° C.

The reaction can be carried out under normal, increased or reduced pressure (for example 0.5 to 5 bar). It is in general carried out under normal pressure.

Suitable palladium compounds in the context of the present invention are in general $PdCl_2(P(C_6H_5)_3)_2$, palladium bis-dibenzylideneacetone $(Pd(dba)_2)$, [1,1'-bis(diphenyl-phosphino)ferrocene]palladium(II) chloride (Pd (dppf)$Cl_2$) or $Pd(P(C_6H_5)_3)_4$. $Pd(P(C_6H_5)_3)_4$ is preferred.

Suitable solvents for process [C3] are some of the abovementioned solvents, benzene being particularly preferred.

Suitable metal salts in the context of the invention are copper salts or rhodium(II) salts, such as, for example, CuOTf, Cu(acac)$_2$ and Rh(OAc)$_2$. Copper acetylacetonate is preferred.

The salts are employed in catalytic amounts.

The reaction is in general carried out in a temperature range from 0° C. to 150° C., preferably +20° C. to +110° C.

The reaction can be carried out under normal, increased or reduced pressure (for example 0.5 to 5 bar). It is in general carried out under normal pressure.

Process [D3] according to the invention is carried out with one of the abovementioned cyclic amine bases, preferably with N-methylpyrrolidone, in a temperature range from 100° C. to 200° C., preferably at 150° C.

Process [E3] according to the invention is carried out in a temperature range from 150° C. to 210° C., preferably at 195° C.

Process [F3] according to the invention is in general carried out in one of the abovementioned ethers, preferably in tetrahydrofuran at the reflux temperature.

The reaction of the free methylhydroxy group to give the corresponding methylalkoxy compounds is carried out by customary methods by alkylation with alkyl halides, preferably alkyl iodides, in the presence of one of the abovementioned bases, preferably sodium hydride.

The compounds of the general formulae (III-III), (III-V), (III-VI), (III-VII), (III-VIII), (III-IX), (III-XI), (III-XII), (III-XIV), (III-XVI) and (III-XVIII) are known per se or can be prepared by customary methods.

The compounds of the general formula (III-II) are known in some cases and can be prepared by a process in which compounds of the general formula (III-XXXIX)

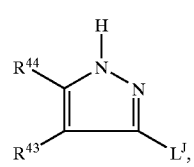

(III-XXXIX)

in which $R^{43}$ and $R^{44}$ have the abovementioned meaning and $L^{3'}$ has the abovementioned meaning of $L^3$ and is identical to or different from this, are reacted with compounds of the general formula (III-V) analogously to the abovementioned process [B3].

The compounds of the general formula (III-IV) are known in some cases or, in the case of the stannyls, are new and can be prepared, for example, by a process in which the compounds of the general formula (III-IVa)

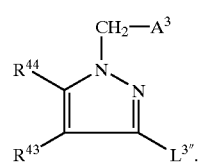

(III-IVa)

in which $R^{43}$, $R^{44}$ and $A^3$ have the abovementioned meaning, and $L^{3'}$ represents triflate or halogen, preferably iodine, are reacted with compounds of the general formula (III-XXX)

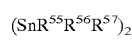

$(SnR^{55}R^{56}R^{57})_2$       (III-XXX), wherein $R^{55}$, $R^{56}$ and $R^{57}$ have the abovementioned meaning under palladium catalysis as described above.

The compounds of the general formulae (III-IVa) and (III-XXX) are known or can be prepared by customary methods.

The compounds of the general formulae (III-X), (III-XIII), (III-XVII) and (III-XIX) are new in some cases and can be prepared, for example, as described above.

Process [H3] proceeds by customary methods in the context of the invention, in particular in accordance with the descriptions from the publications P. Wipf, C P. Miller, J. Org. Chem. 1993, 58, 3604, C. S. Moody et al., Synlett 1966, page 825.

The compounds of the general formula (III-XX) are known in some cases or can be prepared from the corresponding amides by reaction with (α-diazo-β-keto esters under rhodium salt catalysis (in this context, cf. C. J. Moody et al., Synlett 1996, 825).

Process [I3] is carried out by the customary methods for the preparation of acetals. The reduction steps are described in detail below.

The compounds of the general formulae (III-XXI), (III-XXII) and (III-XXIII) are known in some cases or are new as a species, and can then be prepared as described above.

Process [I3] is carried out analogously to the publications S. Chim and H. J. Shirie, J. Heterocycl. Chem. 1989, 26, 125 and J. Med. Chem. 1990, 33, 113.

The compounds of the general formulae (II-XXIV) and (III-XXV) are known in some cases or can be prepared by customary methods.

The compounds of the general formula (III-XXVI) are known in some cases or are new, and can then be prepared from the corresponding cyano-substituted compounds and hydroxylamine hydrochloride. If appropriate, a base, preferably sodium methanolate in methanol, can be added for this reaction.

The compounds of the general formula (III-XXVII) are known per se or can be prepared by customary methods.

Processes [H3] to [J3] in general proceed in a temperature range from 0° C. up to the particular reflux temperature under normal pressure.

The reductions are in general carried out with reducing agents, preferably with those which are suitable for reduction of carbonyl to hydroxy compounds. A particularly suitable reduction here is reduction with metal hydrides or complex metal hydrides in inert solvents, if appropriate in the presence of a trialkylborane. The reduction is preferably carried out with complex metal hydrides, such as, for example, lithium boranate, sodium boranate, potassium boranate, zinc boranate, lithium trialkylhydrido-boranate, diisobutylaluminium hydride or lithium aluminium hydride. The reduction is especially preferably carried out with diisobutylaluminium hydride and sodium borohydride.

The reducing agent is in general employed in an amount of 1 mol to 6 mol, preferably 1 mol to 4 mol, per mole of the compounds to be reduced.

The reduction in general proceeds in a temperature range from −78° C. to +50° C., preferably from −78° C. to 0° C., in the case of DIBAH, 0° C., room temperature in the case of $NaBH_4$, particularly preferably at −78° C., in each case depending on the choice of reducing agent and solvents.

The reduction in general proceeds under normal pressure, but it is also possible to carry it out under increased or reduced pressure.

The protective group is in general split off in one of the abovementioned alcohols and/or tetrahydrofuran or acetone, preferably methanol/tetrahydrofuran, in the presence of hydrochloric acid or trifluoroacetic acid or toluenesulphonic acid in a temperature range from 0° C. to 70° C., preferably at room temperature under normal pressure.

In the case where the radicals of the formulae $—S(O)_{c3}NR^{50}R^{51}$ and $—S(O)_{c3}NR^{50'}R^{51'}$ are present, the corresponding unsubstituted compounds are first reacted with thionyl chloride. The reaction with the amines in one of the abovementioned ethers, preferably dioxane, is carried out in a further step. In the case where c3=2, oxidation by customary methods is subsequently carried out. The reactions are carried out in a temperature range from 0° C. to 70° C. under normal pressure.

Compounds according to the invention according to embodiment III in which $R^{42}$ represents an oxazolyl radical of the formula (III-XXVIII)

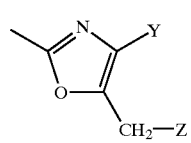

(III-XXVIII)

wherein Y and Z have the meaning given below can preferably be prepared by the new process described below, which can be used generally for the preparation of oxazolyl compounds of this type.

The invention thus furthermore relates to a process for the preparation of oxazolyl compounds of the general formula (III-XXIX)

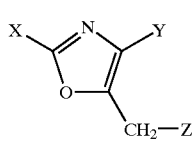

(III-XXIX)

in which

X and Y are identical or different and can represent optionally substituted aliphatic, cycloaliphatic, araliphatic, aromatic and heterocyclic radicals, including saturated, unsaturated or aromatic, heteromono- or heteropolycyclic radicals, carboxyl, acyl, alkoxy, alkoxycarbonyl or cyano or can represent hydrogen, wherein the aromatic and heterocyclic radicals can be substituted by one or more substituents which are chosen from the group which consists of:

halogen, formyl, acyl, carboxyl, hydroxyl, alkoxy, aroxy, acyloxy, optionally alkyl-substituted amino, acylamino, aminocarbonyl, alkoxycarbonyl, nitro, cyano, phenyl and alkyl, which can be substituted by one or more substituents which are chosen from the group which consists of:

halogen, hydroxyl, amino, carboxyl, acyl, alkoxy, alkoxycarbonyl and heterocyclyl and phenyl, which can be substituted by one or more substituents chosen from:

amino, mercaptyl, hydroxyl, formyl, carboxyl, acyl, alkylthio, alkyloxyacyl, alkoxy, alkoxycarbonyl, nitro, cyano, trifluoromethyl, azido, halogen, phenyl and alkyl which is optionally substituted by hydroxyl, carboxyl, acyl, alkoxy or alkoxycarbonyl, and wherein the aliphatic, cycloaliphatic and araliphatic radicals can be substituted by one or more substituents which are chosen from the group which consists of: fluorine, hydroxyl, alkoxy, aroxy, acyloxy, alkyl-substituted amino, acylamino, aminocarbonyl, alkoxycarbonyl and acyl, Z is chosen from the group which consists of:
hydroxyl, alkoxy, optionally alkyl- and/or halogen-substituted arylalkoxy, optionally alkyl- and/or halogen-substituted aroxy, aroyloxy, acyloxy, alkylthio, optionally alkyl- and/or halogen-substituted arylthio, diacylimido or a group of the formula (III-XXX)

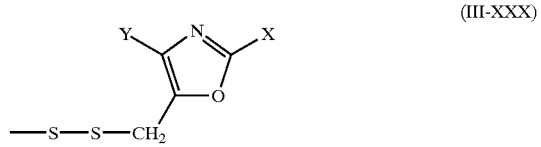

(III-XXX)

in which Y and X have the abovementioned meaning, characterized in that amides of the formula (III-XXXI)

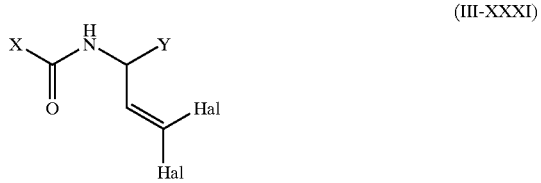

(III-XXXI)

in which Y and X have the abovementioned meaning and Hal represents chlorine or bromine, are reacted with compounds of the formula $M1^+Z^-$ or $M2^{2+}(Z^-)_2$, in which M1 is an alkali metal, M2 is an alkaline earth metal and Z is as defined above.

In respect of concrete examples which contain the above definitions of the substituents in their scope, reference is made to the corresponding meanings in the explanations given above on the compounds of embodiment III of the present invention.

In a preferred embodiment of this process, oxazolyl compounds of the present invention in which X in the above general formula (III-XXIX) is

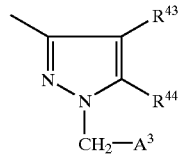

wherein $R^{43}$, $R^{44}$ and $A^3$ are as defined above and Y is alkyl or optionally alkyl- or halogen-substituted phenyl, are prepared.

Examples which may be mentioned of oxazoles which are obtained by the preparation process are: 2,4-dimethyl-5-methoxymethyl-oxazole, 2-ethyl-5-methoxymethyl-oxazole, 2-isopropyl-4-ethyl-5-ethoxymethyl-oxazole, 2-cyclopropyl-4-hexyl-5-isopropoxymethyl-oxazole, 2-phenyl-4-methyl-5-methoxymethyl-oxazole, 2-(m-trifluoromethyl-phenyl)-4-methyl4-butoxymethyl-oxazole, 4-methyl-5-methoxymethyl-2-(m-trifluorophenyl)-oxazole, 2-phenyl-4-methyl-5-phenoxymethyl-oxazole, 2-(2-chloro-6-fluorophenyl)-4-methyl-5-p-tert-butylphenoxymethyl-oxazole, 2,4-dimethyl-5-acetoxymethyl-oxazole, 2,4-dimethyl-5-(3-heptylcarbonyloxy)methyl-oxazole, 2-phenyl-4-methyl-5-acetoxymethyl-oxazole, 2-(1-benzylindazol-3-yl)-5-hydroxymethyl-4-methyl-oxazole, 5-acetoxymethyl-2-(1-benzylindazol-3-yl)-4-methyl-oxazole, 2-(1-benzylindazol-3-yl)-5-methoxymethyl-4-methyl-oxazole, 2-[1-(2-fluorobenzyl)indazol-3-yl]-5-hydroxymethyl-4-methyl-oxazole, 2-[1-(2-fluorobenzyl)-indazol-3-yl]-5-methoxymethyl-4-methyl-oxazole, 2-[1-(2-fluorobenzyl)indazol-3-yl]-4-methyl-5-(N-phthalimidomethyl)-oxazole, 4-ethyl-2-[1-(2-fluorobenzyl)-indazol-3-yl]-5-hydroxymethyl-oxazole, 2-phenyl-4-ethyl-5-benzoyloxymethyl-oxazole, 2-phenyl-4-methyl-5-methylmercaptomethyl-oxazole, bis[(2-phenyl4-methyl-oxazol-5-yl)methyl]disulphide and 2-phenyl-4-methyl-5-N-phthalimidomethyl-oxazole.

The process according to the invention for the preparation of the oxazole compounds is carried out, for example, by a process in which amides are reacted, according to equation (a), with compounds of the formula $M1^+Z^-$ or $M2^{2+}(Z^-)_2$:

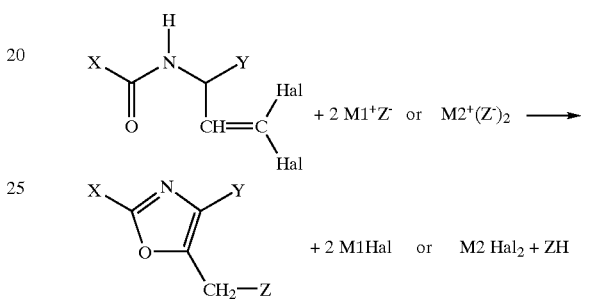

(a)

M1 in the compound $M1^+Z^-$ is an alkali metal chosen from, for example, lithium (Li), sodium (Na) or potassium (K), preferably sodium or potassium. Examples which may be mentioned of compounds of the formula $M1^{+Z-}$ are alcoholates, such as Na methylate, Na butylate or K tert-butylate, phenolates, such as Na phenolate and Na 4-tert-butyl-phenolate, carboxylic acid salts, such as Na acetate or K acetate, Li butyrate, Na benzoate and Na 2,6-difluorobenzoate, phthalimide salts, such as K phthalimides and Na phthalimides, hydroxides, such as KOH, NaOH and LiOH, mercaptides, such as the sodium salts of methylmercaptan or thiophenol, and $Na_2S_2$, which leads to the disulphide of the formula

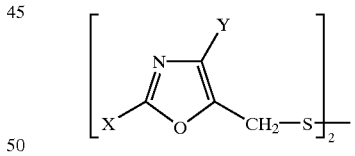

M2 in the compound $M2^{2+}(Z^-)_2$ is an alkaline earth metal chosen from, for example, magnesium or calcium.

The reaction according to the invention in accordance with equation (a) is carried out in solvents at temperatures from about 20° C. to 200° C. Suitable solvents are polar compounds, such as, for example, dimethylformamide, dimethylacetamide, N-methylpyrrolidone, N-methyl-p-caprolactam and dimethyl sulphoxide, and compounds of the formula Z—H are furthermore also possible as solvents, for example the reaction of the amides with Na methylate can be carried out successfully in methanol. Addition of basic auxiliaries, such as, for example, $K_2CO_3$ or $Cs_2CO_3$, may be advantageous. The resulting oxazoles are isolated, after removal of insoluble salts by filtration and, if appropriate, removal of solvents by distillation, by extraction of the oxazoles with suitable solvents, such as, for example, hydrocarbons, such as cyclohexane or toluene, or chlorohydrocarbons, such as, for example, methylene chloride or chlorobenzene, or esters, such as ethyl acetate or ethers, from the crude product, to which water has been added to remove water-soluble products. The crude product can be purified by customary processes, such as, for example, distillation or crystallization or by chromatography.

The amides as starting compounds are obtained by known processes, for example starting from compounds of the formula a, b or c.

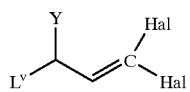

a: Hal=Cl or Br; L'=NH$_2$ b: Hal=Cl or Br; L'=OH c: Hal=Cl or Br; L'=Cl or Br

Starting from amines of the formula a, amines of the formula (III-XXXI) are obtained in a known manner by reaction with corresponding acylating agents, such as, for example, acid halides, esters or acids.

Starting from compounds of the formula b or c, amides are obtained in a known manner by reaction with nitriles in the presence of strong acids.

Amides corresponding to the formula a are accessible, for example, by hydrolysis under acid conditions from amides, which are obtained in a known manner by a Ritter reaction from alkyl halides or allyl alcohols of the formula b and c. Finally, such amines can also be obtained via allylic nucleophilic substitution with, for example, phthalimide salts from the corresponding allyl halides of the formula c via the stage of the corresponding substituted phthalimides and subsequent solvolysis.

Compounds of the formula b are readily accessible according to equation (b) and (c) in two reaction steps from simple starting materials in a known manner:

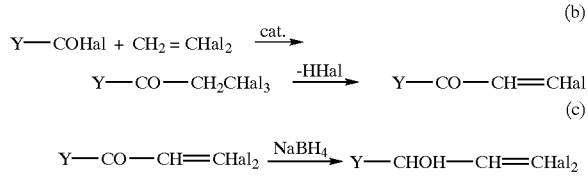

Compounds of the formula c are obtained in a known manner, for example by addition, initiated by free radicals, of carbon tetrachloride or tetrabromide onto corresponding olefinic compounds and subsequent elimination of hydrogen halide in accordance with equation (d):

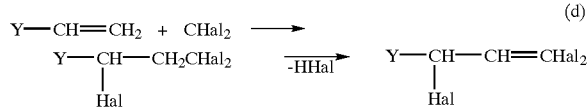

The invention moreover relates to the combination of the compounds of the general formulae (III-I)/(III-Ia) according to the invention with organic nitrates and NO donors.

Organic nitrates and NO donors in the context of the invention are in general substances which display their therapeutic action via the liberation of NO or NO species. Sodium nitroprusside (SNP), nitroglycerol, isosorbide dinitrate, isosorbide mononitrate, molsidomine and SIN-1 are preferred.

The invention also relates to the combination with compounds which inhibit the breakdown of cyclic guanosine monophosphate (cGMP). These are, in particular, inhibitors of phosphodiesterases 1, 2 and 5; nomenclature according to Beavo and Reifsnyder (1990) TIPS 11 pages 150–155. The action of the compounds according to the invention is potentiated and the desired pharmacological effect increased by these inhibitors.

The compounds of the general formulae (III-I)/(III-Id) according to the invention show an unforeseeable, valuable pharmacological action spectrum.

The compounds of the general formulae (III-I)/(III-Id) according to the invention lead to a vessel relaxation/ inhibition of platelet aggregation and to a lowering of blood pressure, as well as to an increase in coronary blood flow. These actions are mediated via direct stimulation of soluble guanylate cyclase and an intracellular increase in cGMP. Furthermore, the compounds according to the invention intensify the action of substances which increase the cGMP level, such as, for example, EDRF (endothelium derived relaxing factor), NO donors, protoporphyrin IX, arachidonic acid or phenylhydrazine derivatives.

They can therefore be employed in medicaments for treatment of cardiovascular diseases, such as, for example, for treatment of high blood pressure and cardiac insufficiency, stable and unstable angina pectoris and peripheral and cardiac vascular diseases and of arrhythmias, for treatment of thromboembolic diseases and ischaemias, such as myocardial infarction, cerebral stroke, transitory and ischaemic attacks and peripheral circulatory disturbances, for preventing restenoses, such as after thrombolysis treatment, percutaneous transluminal angioplasties (PTA), percutaneous transluminal coronary angioplasties (PTCA) and bypass, and for treatment of arteriosclerosis and diseases of the urogenital system, such as, for example, prostate hypertrophy, erectile dysfunction and incontinence.

The following investigations were carried out to determine the cardiovascular actions: the influence on guanylate cyclase-dependent cGMP formation with and without an NO donor was tested in investigations in vitro on cells of vascular origin. The anti-aggregatory properties were demonstrated on human platelets stimulated with collagen. The vessel-relaxing action was determined on rabbit aortic rings precontracted with phenylephrine. The antihypertensive action was investigated on anaesthetized rats.

Stimulation of Soluble Guanylate Cyclase in Primary Endothelial Cells

Primary endothelial cells were isolated from pig aortas by treatment with collagenase solution. The cells were then cultured in a culture medium until confluence was reached. For the investigations, the cells were subjected to passaging, sown in cell culture plates and subcultured until confluence was reached. To stimulate the endothelial guanylate cyclase, the culture medium was suctioned off and the cells were washed once with Ringer's solution and incubated in stimulation buffer with or without NO donor (sodium nitroprusside, SNP, 1 $\mu$M). Thereafter, the test substances (final concentration 1 $\mu$M) were pipetted onto the cells. At the end of the 10-minute incubation period, the buffer solution was suctioned off and the cells were lysed at −20° C. for 16 hours. The intracellular cGMP was then determined radioimmunologically.

TABLE A

| Example No. | % increase in cGMP |
|---|---|
| III-71 | 315 |
| III-73 | >1000 |
| III-74 | 114 |
| III-75 | >1000 |
| III-76 | 397 |
| III-77 | >1000 |
| III-78 | 223 |
| III-79 | 124 |
| III-80 | >1000 |
| III-81 | 110 |
| III-82 | 455 |
| III-87 | 268 |
| III-91 | 479 |
| III-92 | 319 |
| III-93 | 271 |

Vessel-relaxing Action in Vitro

Rings 1.5 mm wide of an aorta isolated from a rabbit are introduced individually, under pretension, in 5 ml organ baths with Krebs-Henseleit solution warmed to 37° C. and gassed with carbogen. The contraction force is amplified and digitalized and recorded in parallel on a line recorder. To generate a contraction, phenylephrine is added cumulatively to the bath in an increasing concentration.

After several control cycles, the substance to be investigated is investigated in each further pass in each case in an increasing dosage, and a comparison is made with the level of the contraction achieved in the last preliminary pass. The concentration necessary to reduce the level of the control value by 50% ($IC_{50}$) is calculated from this. The standard application volume is 5 µl.

TABLE B

| Example No. | Aorta $IC_{50}$ |
|---|---|
| III-71 | 5 µM |
| III-73 | 9.4 µM |
| III-75 | 2.2 µM |
| III-76 | 7.4 µM |
| III-77 | 8.3 µM |
| III-78 | 10 µM |
| III-79 | 13 µM |
| III-80 | 3.6 µM |
| III-81 | 12 µM |
| III-82 | 15 µM |
| III-87 | 19 µM |
| III-88 | 7.1 µM |
| III-90 | 4.1 µM |
| III-95 | 2.4 µM |

Blood Pressure Measurements on Anaesthetized Rats

Male Wistar rats with a body weight of 300–350 g are anaesthetized with thiopental (100 mg/kg i.p.). After tracheotomy, a catheter is inserted into the femoral artery for blood pressure measurement. The substances to be tested are administered orally by means of a stomach tube in various doses as a suspension in tylose solution.

Inhibition of Platelet aggregation in Vitro

To determine the platelet aggregation-inhibiting action, blood from healthy subjects of both sexes was used. One part of 3.8% strength aqueous sodium citrate solution was admixed to 9 parts of blood as an anticoagulant. Platelet-richer citrate plasma (PRP) is obtained from this blood by means of centrifugation.

For the investigations, 445 µl of PRP and 5 µl of the active compound solution were preincubated in a water-bath at 37° C. The platelet aggregation was then determined in an aggregometer at 37° C. using the turbidometric method. For this, 50 µl of collagen, an aggregation-inducing agent, were added to the preincubated sample and the change in optical density was recorded. For the quantitative evaluation, the maximum aggregation response was determined and the percentage inhibition compared with the control was calculated therefrom.

TABLE D

| Example No. | $IC_{50}$ (µg/ml) |
|---|---|
| III-71 | 50 |
| III-72 | 1 |

The compounds of embodiment III which are described in the present invention are also active compounds for combating diseases in the central nervous system which are characterized by impairments of the NO/cGMP system. In particular, they are suitable for eliminating cognitive deficits, for improving learning and memory performance and for treatment of Alzheimer's disease. They are also suitable for treatment of diseases of the central nervous system such as states of anxiety, stress and depression, sexual dysfunctions of central nervous origin and sleep disturbances, and for regulating pathological disturbances in the intake of food and addictive substances.

These active compounds are furthermore also suitable for regulation of cerebral circulation and are therefore effective agents for combating migraine.

They are also suitable for prophylaxis and combating the consequences of cerebral infarction events (apoplexia cerebri), such as apoplexy, cerebral ischaemias and craniocerebral trauma. The compounds according to the invention can also be employed for combating states of pain.

The present invention includes pharmaceutical formulations which comprise, in addition to non-toxic, inert pharmaceutically suitable carriers, one or more compounds according to the invention, or which consist of one or more active compounds according to the invention, and processes for the preparation of these formulations.

If appropriate, the active compound or compounds can also be present in microencapsulated form in one or more of the abovementioned carriers.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also comprise further pharmaceutical active compounds in addition to the compounds according to the invention.

In general, it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, to achieve the desired results. An individual dose preferably comprises the active compound or compounds according to the invention in amounts of about 1 to about 80, in particular 3 to 30 mg/kg of body weight.

IV

According to embodiment IV, the present invention relates to 1-benzyl-3-(substituted heteroaryl)-fused pyrazole derivatives of the general formula (IV-I)

(IV-I)

[Structure: pyrazole ring with R69, R70, R71 substituents and CH2—A4 on N]

in which

A⁴ represents phenyl, which is optionally substituted up to 3 times in an identical or different manner by halogen, hydroxyl, cyano, carboxyl, nitro, trifluoromethyl, trifluoromethoxy, azido, straight-chain or branched alkyl, alkoxy or alkoxycarbonyl having in each case up to 6 carbon atoms, R⁶⁹ represents a radical of the formula

[Structures: pyrrole-R72, furan-O-R72, furan-O-R72 with CH3, thiophene-S-R72, or phenyl-R72]

wherein

R⁷² denotes a radical of the formula —CH(OH)—CH₃ or straight-chain or branched alkyl having 2 to 6 carbon atoms, which is substituted once to twice by hydroxyl or straight-chain or branched alkoxy having up to 4 carbon atoms, or denotes formyl, straight-chain or branched acyl having up to 6 carbon atoms, nitro or straight-chain or branched alkyl having up to 6 carbon atoms, which is substituted by amino, azido or by a radical of the formula —OR⁷³, wherein R⁷³ denotes straight-chain or branched acyl having up to 5 carbon atoms or a group of the formula —SiR⁷⁴R⁷⁵R⁷⁶,

[Structures: epoxide with —H₂C and R78, or —CH₂—OR79]

wherein

R⁷⁴, R⁷⁵ and R⁷⁶ are identical or different and denote aryl having 6 to 10 carbon atoms or straight-chain or branched alkyl having up to 6 carbon atoms, R⁷⁸ denotes hydrogen or straight-chain or branched alkyl having up to 3 carbon atoms and R⁷⁹ denotes hydrogen or straight-chain or branched alkyl having up to 4 carbon atoms, or R⁷² denotes a group of the formula

[Structures: C(R81)=N—OR80, or dioxolane with (CH2)a4]

-continued

[Structures: CH(O—(CH2)b4—CH3)(O—(CH2)b4'—CH3), or —S(O)c4NR82R83]

wherein

R⁸⁰ denotes hydrogen or straight-chain or branched alkyl having up to 4 carbon atoms, R⁸¹ denotes hydrogen or straight-chain or branched alkyl having up to 4 carbon atoms and a4 denotes the number 1, 2 or 3, b4 and b4' are identical or different and denote the number 0, 1, 2 or 3, c4 denotes the number 1 or 2 and R⁸² and R⁸³ are identical or different and denote hydrogen or straight-chain or branched alkyl having up to 10 carbon atoms, which is optionally substituted by cycloalkyl having 3 to 8 carbon atoms or by aryl having 6 to 10 carbon atoms, which in its turn can be substituted by halogen, or denote aryl having 6 to 10 carbon atoms, which is optionally substituted by halogen, or denote cycloalkyl having 3 to 7 carbon atoms, or R⁸² and R⁸³, together with the nitrogen atom, form a 5- to 7-membered saturated heterocyclic ring, which can optionally contain a further oxygen atom or a radical —NR⁸⁴, wherein R⁸⁴ denotes hydrogen, straight-chain or branched alkyl having up to 4 carbon atoms or a radical of the formula

[Structure: —CH₂-benzodioxole]

or denotes benzyl or phenyl, wherein the ring systems are optionally substituted by halogen, or R⁷² denotes a group of the formula —CH₂—OR⁸⁵, wherein R⁸⁵ denotes hydrogen or straight-chain or branched alkyl having up to 3 carbon atoms, R⁷⁰ and R⁷¹ together form a radical of the formula

[Structures: pyrrole-R86, furan-R86, thiophene-R86, or phenyl-R86]

wherein

R⁸⁶ denotes hydrogen, halogen, hydroxyl, nitro, amino, trifluoromethyl or straight-chain or branched alkyl or alkoxy having in each case up to 4 carbon atoms, or a group of the formula —S(O)$_{c4'}$NR⁸²'R⁸³', wherein c4', R⁸²' and R⁸³' have the abovementioned meaning of c4, R⁸² and R⁸³ and are identical to or different from these, and their isomeric forms and salts, with the proviso that R⁷², in the case of the phenyl ring and in the position directly adjacent to the heteroatom, may represent the group of the formula —CH$_2$—OR$^{85'}$ only if A$^4$ either represents phenyl, which is substituted by cyano, nitro, trifluoromethyl, azido, carboxyl or straight-chain or branched alkoxycarbonyl having up to 6 carbon atoms, or is substituted at least twice by the radicals listed above, or R$^{86}$ represents nitro, amino, trifluoromethyl or represents the group of the formula —S(O)$_{c4}$NR$^{82'}$R$^{83'}$.

The compounds of the general formula (IV-I) according to the invention can also be present in the form of their salts. Salts with organic or inorganic bases or acids may be mentioned in general here.

Physiologically acceptable salts are preferred in the context of embodiment IV of the present invention. Physiologically acceptable salts can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention if they have a free carboxyl group. Particularly preferred salts are, for example, sodium, potassium, magnesium or calcium salts, and ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

Preferred compounds of the general formula (IV-I) according to the invention are those in which A$^4$ represents phenyl, which is optionally substituted up to 3 times in an identical or different manner by fluorine, chlorine, bromine, hydroxyl, cyano, carboxyl, nitro, trifluoromethyl, trifluoromethoxy, azido, straight-chain or branched alkyl, alkoxy or alkoxycarbonyl having in each case up to 5 carbon atoms, R$^{69}$ represents a radical of the formula

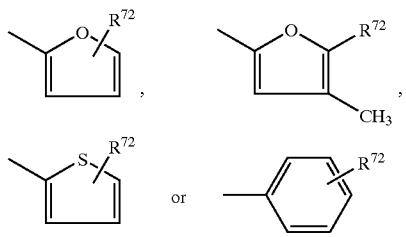

wherein

R$^{72}$ denotes a radical of the formula —CH(OH)—CH$_3$ or straight-chain or branched alkyl having 2 to 4 carbon atoms, which is substituted once to twice by hydroxyl or straight-chain or branched alkoxy having up to 3 carbon atoms, or denotes formyl, straight-chain or branched acyl having up to 4 carbon atoms, nitro or straight-chain or branched alkyl having up to 4 carbon atoms, which is substituted by amino, azido or by a radical of the formula —OR$^{73}$, wherein R$^{73}$ denotes straight-chain or branched acyl having up to 4 carbon atoms or a group of the formula

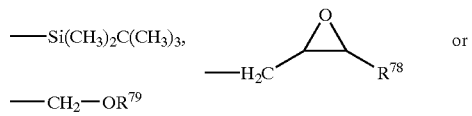

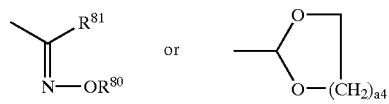

wherein

R$^{78}$ denotes hydrogen or straight-chain or branched alkyl having up to 3 carbon atoms and R$^{79}$ denotes hydrogen or straight-chain or branched alkyl having up to 3 carbon atoms, or k$^{72}$ denotes a group of the formula

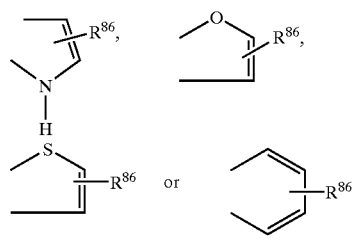

wherein

R$^{80}$ denotes hydrogen or straight-chain or branched alkyl having up to 3 carbon atoms, R$^{81}$ denotes hydrogen or straight-chain or branched alkyl having up to 3 carbon atoms and a4 denotes the number 1 or 2, or R$^{72}$ denotes a group of the formula —CH$_2$—OR$^{85}$, wherein R$^{85}$ denotes hydrogen or straight-chain or branched alkyl having up to 3 carbon atoms, R$^{70}$ and R$^{71}$ together form a radical of the formula wherein R$^{86}$ denotes hydrogen, fluorine, chlorine, bromine, hydroxyl, nitro, amino, trifluoromethyl or straight-chain or branched alkyl or alkoxy having in each case up to 3 carbon atoms, and their isomeric forms and salts, with the proviso that R$^{72}$, in the case of the phenyl ring and in the position directly adjacent to the heteroatom, may represent the group of the formula —CH$_2$—OR$^{85}$ only if A$^4$ either represents phenyl, which is substituted by cyano, nitro, trifluoromethyl, azido, carboxyl or straight-chain or branched alkoxycarbonyl having up to 6 carbon atoms or is substituted at least twice by the radicals listed above, or R$^{86}$ represents nitro, amino or trifluoromethyl.

Particularly preferred compounds of the general formula (IV-I) according to the invention are those in which A$^4$ represents phenyl, which is optionally substituted up to 3 times in an identical or different manner by fluorine, chlorine, bromine, trifluoromethyl, trifluoromethoxy, cyano, nitro, carboxyl, azido, straight-chain or branched alkyl, alkoxy or alkoxycarbonyl having in each case up to 3 carbon atoms, $R^{69}$ represents a radical of the formula

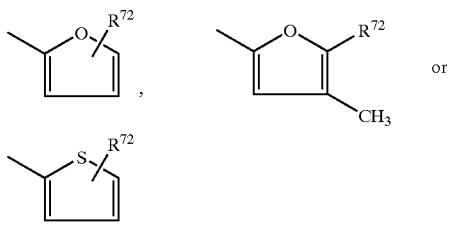

wherein
$R^{72}$ denotes a radical of the formula —CH(OH)—CH$_3$ or straight-chain or branched alkyl having 2 to 4 carbon atoms, which is substituted once to twice by hydroxyl, methyl or methoxy, or denotes formyl, straight-chain or branched acyl having up to 3 carbon atoms, nitro or straight-chain or branched alkyl having up to 3 carbon atoms, which is substituted by amino, azido or by a radical of the formula —OR$^{73}$, wherein $R^{73}$ denotes straight-chain or branched acyl having up to 3 carbon atoms or a group of the formula

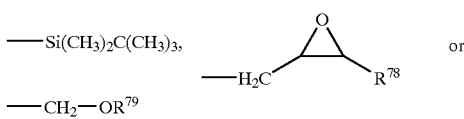

wherein
$R^{78}$ denotes hydrogen or methyl and
$R^{79}$ denotes hydrogen or straight-chain or branched alkyl having up to 3 carbon atoms, or
$R^{72}$ denotes a group of the formula

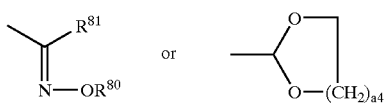

wherein
$R^{80}$ denotes hydrogen or straight-chain or branched alkyl having up to 3 carbon atoms,
$R^{81}$ denotes hydrogen or methyl and
a4 denotes the number 1 or 2, or
$R^{72}$ denotes the group of the formula —CH$_2$—OR$^{85}$, wherein
$R^{85}$ denotes hydrogen or methyl,
$R^{70}$ and $R^{71}$ together form a radical of the formula

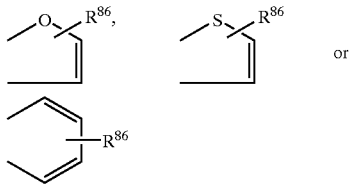

wherein
$R^{86}$ denotes hydrogen, fluorine, chlorine, bromine, nitro, trifluoromethyl, amino, hydroxyl or straight-chain or branched alkyl or alkoxy having in each case up to 3 carbon atoms,
and their isomeric forms and salts.

Especially preferred compounds of the general formula (IV-I) according to the invention are those in which $A^4$ represents phenyl, which is optionally substituted up to twice in an identical or different manner by fluorine, chlorine, methyl, methoxy, cyano, nitro, trifluoromethyl or trifluoromethoxy and $R^{70}$ and $R^{71}$ together, including the double bond, form a phenyl ring, which is optionally substituted by nitro, fluorine, amino or methoxy, with the proviso that $R^{72}$, in the case of the phenyl ring and in the position directly adjacent to the heteroatom, may represent the group of the formula —CH$_2$OR$^{85}$ only if $A^4$ either represents phenyl, which is substituted by cyano, nitro, trifluoromethyl, azido, carboxyl or straight-chain or branched alkoxycarbonyl having up to 6 carbon atoms, or is substituted at least twice by the radicals listed above, or $R^{86}$ represents nitro, amino or trifluoromethyl.

The invention furthermore relates to processes for the preparation of the compounds of the general formula (IV-I) according to the invention, characterized in that

[A4] compounds of the general formula (IV-II)

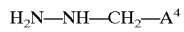

in which
$A^4$ has the abovementioned meaning,
are converted by reaction with compounds of the general formula (IV-III)

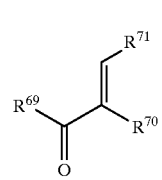

in which
$R^{69}$, $R^{70}$ and $R^{71}$ have the abovementioned meaning, into the compounds of the general formula (IV—IV)

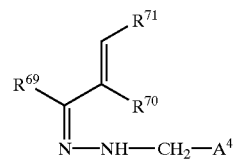

in which
$A^4$, $R^{69}$, $R^{70}$ and $R^{71}$ have the abovementioned meaning, in inert solvents, if appropriate in the presence of an acid, and the products are finally oxidized and cyclized with lead tetraacetate/BF$_3$×ether, or

[B4] compounds of the general formula (IV-V)

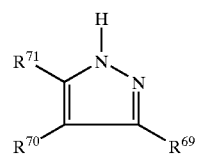

in which $R^{69}$, $R^{70}$ and $R^{71}$ have the abovementioned meaning, are reacted with compounds of the general formula (IV-VI)

  (IV-VI)

in which $A^4$ has the abovementioned meaning and $D^4$ represents triflate or halogen, preferably bromine, in inert solvents, if appropriate in the presence of a base, or

[C4] compounds of the general formula (IV-VII)

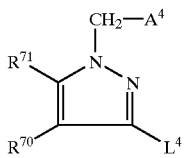  (IV-VII)

in which $A^4$, $R^{70}$ and $R^{71}$ have the abovementioned meaning and $L^4$ represents a radical of the formula $-SnR^{87}R^{88}R^{89}$, $ZnR^{90}$, iodine or triflate wherein $R^{87}$, $R^{88}$ and $R^{89}$ are identical or different and denote straight-chain or branched alkyl having up to 4 carbon atoms and $R^{90}$ denotes halogen, are reacted with compounds of the general formula (IV-VIII)

  (IV-VIII)

in which $R^{69}$ has the abovementioned meaning and in the case where $L^4=SnR^{87}R^{88}R^{89}$ or ZnR90, $T^4$ represents triflate or represents halogen, preferably bromine, and in the case where $L^4$=iodine or triflate, $T^4$ represents a radical of the formula $SnR^{87'}R^{88'}R^{89'}$, $ZnR^{90'}$ or $BR^{91}R^{92}$ wherein $R^{87'}$, $R^{88'}$, $R^{89'}$ and $R^{90'}$ have the abovementioned meaning of $R^{87}$, $R^{88}$, $R^{89}$ and $R^{90}$ and are identical to or different from these and $R^{91}$ and $R^{92}$ are identical or different and denote hydroxyl, aryloxy having 6 to 10 carbon atoms or straight-chain or branched alkyl or alkoxy having in each case up to 5 carbon atoms, or together form a 5- or 6-membered carbocyclic ring in a palladium-catalysed reaction in inert solvents, or

[D4] in the case where $R^{72}$ represents an alkyl having 2 to 6 carbon atoms, which is substituted twice by hydroxyl, compounds of the general formula (IV-Ia)

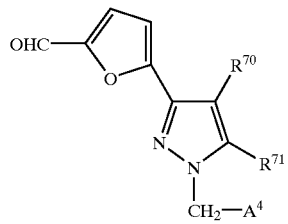  (IV-Ia)

in which $A^4$, $R^{70}$ and $R^{71}$ have the abovementioned meaning, are first converted by a Wittig reaction in the system $(C_6H_5)_3P^{\oplus}-CH_2^{\ominus}$ into the compounds of the general formula (IV-IX)

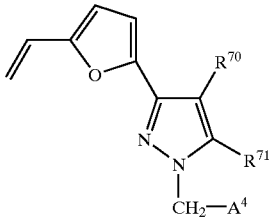  (IV-IX)

in which $R^{70}$, $R^{71}$ and $A^4$ have the abovementioned meaning, and finally the hydroxyl functions are introduced with osmium tetroxide, and, if appropriate, the substituents listed under $R^{69}$, $R^{70}$, $R^{71}$ and/or $A^4$ are varied or introduced by customary methods, preferably by reduction, oxidation, splitting off of protective groups and/or nucleophilic substitution.

The processes according to the invention can be illustrated by way of example by the following equations:

[A4]

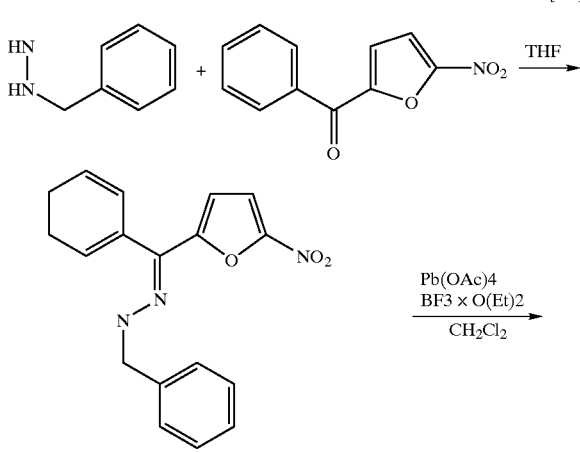

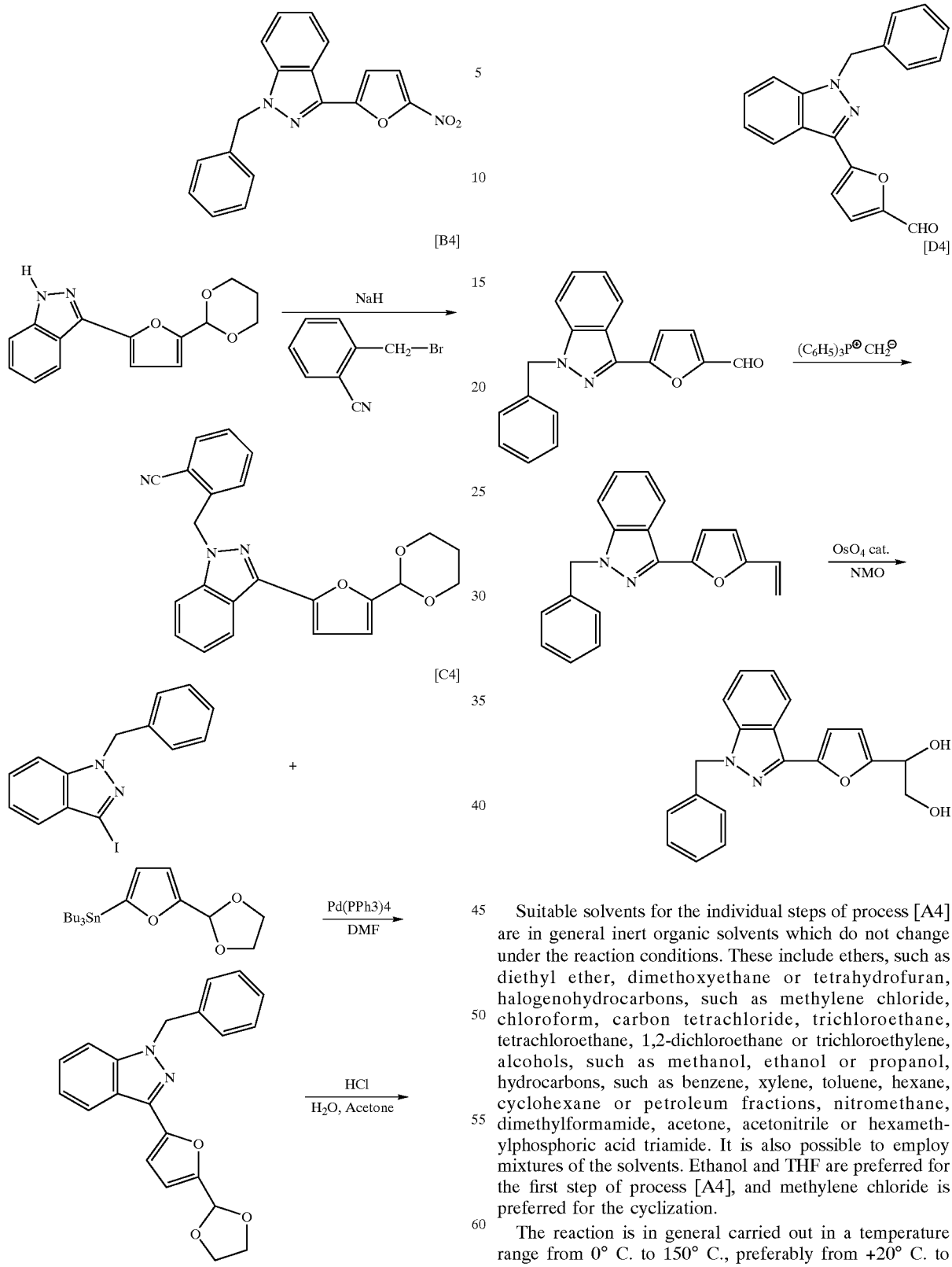

Suitable solvents for the individual steps of process [A4] are in general inert organic solvents which do not change under the reaction conditions. These include ethers, such as diethyl ether, dimethoxyethane or tetrahydrofuran, halogenohydrocarbons, such as methylene chloride, chloroform, carbon tetrachloride, trichloroethane, tetrachloroethane, 1,2-dichloroethane or trichloroethylene, alcohols, such as methanol, ethanol or propanol, hydrocarbons, such as benzene, xylene, toluene, hexane, cyclohexane or petroleum fractions, nitromethane, dimethylformamide, acetone, acetonitrile or hexamethylphosphoric acid triamide. It is also possible to employ mixtures of the solvents. Ethanol and THF are preferred for the first step of process [A4], and methylene chloride is preferred for the cyclization.

The reaction is in general carried out in a temperature range from 0° C. to 150° C., preferably from +20° C. to +110° C.

The reaction can be carried out under normal, increased or reduced pressure (for example 0.5 to 5 bar). It is in general carried out under normal pressure.

Suitable acids are in general carboxylic acids, such as, for example, acetic acid, toluenesulphonic acid, sulphuric acid or hydrogen chloride. Acetic acid is preferred.

Suitable solvents here for the individual steps of process [B4] are inert organic solvents which do not change under the reaction conditions. These include ethers, such as diethyl ether or tetrahydrofuran, hydrocarbons, such as benzene, xylene, toluene, hexane, cyclohexane or petroleum fractions, nitromethane, dimethylformamide, acetone, acetonitrile or hexamethylphosphoric acid triamide. It is also possible to employ mixtures of the solvents. Tetrahydrofuran, toluene or dimethylformamide are particularly preferred.

Bases which can be employed for the process according to the invention are in general inorganic or organic bases. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or alkali metal or alkaline earth metal alcoholates, such as sodium or potassium methanolate, sodium or potassium ethanolate or potassium tert-butylate, or organic amines (trialkyl-($C_1$–$C_6$) amines), such as triethylamine, or heterocyclic compounds, such as 1,4-diazabicyclo[2.2.2]octane (DABCO), 1,8-diazabicyclo-[5.4.0]undec-7-ene (DBU), pyridine, diaminopyridine, methylpiperidine or morpholine.

It is also possible to employ as the bases alkali metals, such as sodium, and hydrides thereof, such as sodium hydride. Sodium carbonate and potassium carbonate, triethylamine and sodium hydride are preferred.

The base is employed in an amount of 1 mol to 5 mol, preferably 1 mol to 3 mol, per mole of the compound of the general formula (IV-II).

The reaction is in general carried out in a temperature range from 0° C. to 150° C., preferably from +20° C. to +110° C.

The reaction can be carried out under normal, increased or reduced pressure (for example 0.5 to 5 bar). It is in general carried out under normal pressure.

Suitable solvents here for processes [C4] and [D4] are inert organic solvents which do not change under the reaction conditions. These include ethers, such as diethyl ether or tetrahydrofuran, DME or dioxane, halogenohydrocarbons, such as methylene chloride, chloroform, carbon tetrachloride, trichloroethane, tetrachloroethane, 1,2-dichloroethane or trichloroethylene, hydrocarbons, such as benzene, xylene, toluene, hexane, cyclohexane or petroleum fractions, nitromethane, dimethylformamide, acetone, acetonitrile or hexamethylphosphoric acid triamide. It is also possible to employ mixtures of the solvents. Tetrahydrofuran, dimethylformamide, toluene, dioxane or dimethoxyethane are particularly preferred.

The reaction is in general carried out in a temperature range from 0° C. to 150° C., preferably from +20° C. to +110° C.

The reaction can be carried out under normal, increased or reduced pressure (for example 0.5 to 5 bar). It is in general carried out under normal pressure.

Suitable palladium compounds in the context of the present invention are in general $PdCl_2((C_6H_5)_3)_2$, palladium bis-dibenzylideneacetone (Pd(dba)$_2$), [1,1'-bis-(diphenylphosphino)ferrocene]-palladium(II) chloride (Pd (dppf)Cl$_2$) or Pd(P($C_6H_5$)$_3$)$_4$.

Pd(P($C_6H_5$)$_3$)$_4$ is preferred.

The compounds of the general formulae (IV-II), (IV-III), (IV-VI) and (IV-VIII) are known per se or can be prepared by customary methods.

The compounds of the general formula (IV-IV) are known in some cases or can be prepared as described above.

The compounds of the general formula (IV-V) are known in some cases and can be prepared by a process in which compounds of the general formula (IV-IX)

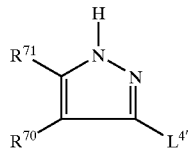

(IV-IX)

in which $R^{70}$ and $R^{71}$ have the abovementioned meaning and $L^4$ has the abovementioned meaning of $L^4$ and is identical to or different from this, are reacted with compounds of the general formula (IV-VIII) analogously to the abovementioned process [C4].

The compounds of the general formula (IV-VII) are known in some cases or, in the case of the stannyls, are new and can then be prepared, for example, by a process in which the compounds of the general formula (IV-VIIa)

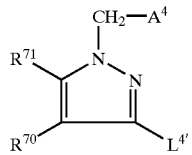

(IV-VIIa)

in which $R^{70}$, $R^{71}$ and A have the abovementioned meaning, and $L^{4''}$ represents triflate or halogen, preferably iodine, are reacted with compounds of the general formula (IV-X)

$$(SnR^{87}R^{88}R^{89})_2 \qquad (IV-X)$$

in which $R^{87}$, $R^{88}$ and $R^{89}$ have the abovementioned meaning, under palladium catalysis as described above.

The compounds of the general formulae (IV-VIIa), (IV-IX) and (IV-X) are known or can be prepared by customary methods.

The compounds of the general formula (IV-IX) are new and can be prepared as described above.

The reductions are in general carried out with reducing agents, preferably with those which are suitable for reduction of carbonyl to hydroxy compounds. A particularly suitable reduction here is reduction with metal hydrides or complex metal hydrides in inert solvents, if appropriate in the presence of a trialkylborane. The reduction is preferably carried out with complex metal hydrides, such as, for example, lithium boranate, sodium boranate, potassium boranate, zinc boranate, lithium trialkylhydridoboranate, diisobutylaluminium hydride or lithium aluminium hydride. The reduction is especially preferably carried out with diisobutylaluminium hydride and sodium borohydride.

The reducing agent is in general employed in an amount of 1 mol to 6 mol, preferably 1 mol to 4 mol, per mole of the compounds to be reduced.

The reduction in general proceeds in a temperature range from −78° C. to +50° C., preferably from −78° C. to 0° C., in the case of DIBAH, 0° C., room temperature in the case of NaBH$_4$, particularly preferably at −78° C., in each case depending on the choice of reducing agent and solvents.

The reduction in general proceeds under normal pressure, but it is also possible to carry it out under increased or reduced pressure.

In the case of the radicals —S(O)$_{c4}$R$^{81}$R$^{82}$ and —S(O)$_{c4}$R$^{81'}$R$^{82'}$, the corresponding unsubstituted compounds of the general formula (IV-I) are first reacted with thionyl chloride. The reaction with the amines in one of the above-mentioned ethers, preferably dioxane, is carried out in a further step. In the case where c4=2, oxidation by customary methods is subsequently carried out. The reactions are carried out in a temperature range from 0° C. to 70° C. under normal pressure.

The protective group is in general split off in one of the abovementioned alcohols and/or tetrahydrofuran or acetone, preferably methanol/tetrahydrofuran, in the presence of hydrochloric acid or trifluoroacetic acid or toluenesulphonic acid in a temperature range from 0° C. to 70° C., preferably at room temperature under normal pressure.

The compounds of the general formula (IV-Ic) are new and can be prepared as described under processes [A4] to [C4].

The invention moreover relates to the combination of the compounds of the general formulae (IV-I) and (IV-Ia) according to the invention with organic nitrates and NO donors.

Organic nitrates and NO donors in the context of the invention are in general substances which display their therapeutic action via the liberation of NO or NO species. Sodium nitroprusside, nitroglycerol, isosorbide dinitrate, isosorbide mononitrate, molsidomine and SIN-1 are preferred.

The invention also relates to the combination with compounds which inhibit the breakdown of cyclic guanosine monophosphate (cGMP). These are, in particular, inhibitors of phosphodiesterases 1, 2 and 5; nomenclature according to Beavo and Reifsnyder (1990) TIPS 11 pages 150–155. The action of the compounds according to the invention is potentiated and the desired pharmacological effect increased by these inhibitors.

The compounds of the general formula (IV-I) and (IV-Ia) according to the invention show an unforeseeable, valuable pharmacological action spectrum.

The compounds of the general formulae (IV-I) and (IV-Ia) according to the invention lead to a vessel relaxation/inhibition of platelet aggregation and to a lowering of blood pressure, as well as to an increase in coronary blood flow. These actions are mediated via direct stimulation of soluble guanylate cyclase and an intracellular increase in cGMP. Furthermore, the compounds according to the invention intensify the action of substances which increase the cGMP level, such as, for example, EDRF (endothelium derived relaxing factor), NO donors, protoporphyrin IX, arachidonic acid or phenylhydrazine derivatives.

They can therefore be employed in medicaments for treatment of cardiovascular diseases, such as, for example, for treatment of high blood pressure and cardiac insufficiency, stable and unstable angina pectoris and peripheral and cardiac vascular diseases and of arrhythmias, for treatment of thromboembolic diseases and ischaemias, such as myocardial infarction, cerebral stroke, transitory and ischaemic attacks and peripheral circulatory disturbances, for preventing restenoses, such as after thrombolysis treatment, percutaneous transluminal angioplasties (PTA), percutaneous transluminal coronary angioplasties (PTCA) and bypass, and for treatment of arteriosclerosis and diseases of the urogenital system, such as, for example, prostate hypertrophy, erectile dysfunction and incontinence.

The following investigations were carried out to determine the cardiovascular actions: the influence on guanylate cyclase-dependent cGMP formation with and without an NO donor was tested in investigations in vitro on cells of vascular origin. The anti-aggregatory properties were demonstrated on human platelets stimulated with collagen. The vessel-relaxing action was determined on rabbit aortic rings precontracted with phenylephrine. The antihypertensive action was investigated on anaesthetized rats.

Stimulation of Soluble Guanylate Cyclase in Primary Endothelial Cells

Primary endothelial cells were isolated from pig aortas by treatment with collagenase solution. The cells were then cultured in a culture medium until confluence was reached. For the investigations, the cells were subjected to passaging, sown in cell culture plates and subcultured until confluence was reached. To stimulate the endothelial guanylate cyclase, the culture medium was suctioned off and the cells were washed once with Ringer's solution and incubated in stimulation buffer with or without an NO donor (sodium nitroprusside, SNP, 1 μM). Thereafter, the test substances (final concentration 1 μM) were pipetted onto the cells. At the end of the 10-minute incubation period, the buffered solution was suctioned off and the cells were lysed at 20° C. for 16 hours. The intracellular cGMP was then determined radioimmunologically.

TABLE A

| Example No. | % increase in cGMP |
| --- | --- |
| IV-136 | >1000 |
| IV-138 | 324 |
| IV-139 | 723 |
| IV-140 | 619 |
| IV-143 | >1000 |
| IV-163 | 341 |
| IV-148 | 978 |
| IV-164 | 289 |
| IV-165 | 256 |
| IV-171 | 926 |
| IV-175 | 473 |
| IV-179 | 921 |

Vessel-Relaxing Action in Vitro

Rings 1.5 mm wide of an aorta isolated from a rabbit are introduced individually, under pretension, in 5 ml organ baths with Krebs-Henseleit solution warmed to 37° C. and gassed with carbogen. The contraction force is amplified and digitalized and recorded in parallel on a line recorder. To generate a contraction, phenylephrine is added cumulatively to the bath in an increasing concentration.

After several control cycles, the substance to be investigated is investigated in each further pass in each case in an increasing dosage, and a comparison is made with the level of the contraction achieved in the last preliminary pass. The concentration necessary to reduce the level of the control value by 50% (IC$_{50}$) is calculated from this.

TABLE B

| Example No. | AORTA IC$_{50}$(μm) |
| --- | --- |
| IV-136 | 7.2 |

TABLE B-continued

| Example No. | AORTA IC$_{50}$($\mu$m) |
|---|---|
| IV-139 | 12 |
| IV-140 | 12–17 |
| IV-153 | 9.1 |
| IV-148 | 6.7 |
| IV-164 | 12 |
| IV-165 | 29 |
| IV-166 | 18 |
| IV-171 | 8.7 |
| IV-175 | 11 |
| IV-179 | 11 |

Blood Pressure Measurements on Anaesthetized Rats

Male Wistar Rats with a bodyweight of 300–350 g are anaesthetized with thiopental (100 mg/kg i.p.). After tracheotomy, a catheter is inserted into the femoral artery for blood pressure measurement. The substances to be tested are administered orally by means of a stomach tube in various doses as a suspension in tylose solution.

The present invention includes pharmaceutical formulations which comprise, in addition to non-toxic, inert pharmaceutically suitable carriers, one or more compounds according to the invention, or which consist of one or more active compounds according to the invention, and processes for the preparation of these formulations.

Inhibition of Platelet Aggregation in Vitro

To determine the platelet aggregation-inhibiting action, blood from healthy subjects of both sexes was used. One part of 3.8% strength aqueous sodium citrate solution was admixed to 9 parts of blood as an anticoagulant. Platelet-richer citrate plasma (PRP) is obtained from this blood by means of centrifugation.

For these investigations, 445 $\mu$l of PRP and 5 $\mu$l of the active compound solution were preincubated in a water-bath at 37° C. The platelet aggregation was then determined in an aggregometer at 37° C. using the turbidometric method. For this, 50 $\mu$l of collagen, an aggregation-inducing agent, were added to the preincubated sample and the change in optical density was recorded. For the quantitative evaluation, the maximum aggregation response was determined and the percentage inhibition compared with the control was calculated therefrom.

TABLE C

| Example No. | IC$_{50}$ ($\mu$g/ml) |
|---|---|
| IV-136 | 30 |

The compounds described in the present invention in embodiment IV are also active compounds for combating diseases in the central nervous system which are characterized by impairments of the NO/cGMP system. In particular, they are suitable for eliminating cognitive deficits, for improving learning and memory performance and for treatment of Alzheimer's disease. They are also suitable for treatment of diseases of the central nervous system such as states of anxiety, stress and depression, and pathological disturbances of central nervous origin in the intake of food and addictive substances.

These active compounds are furthermore also suitable for regulation of cerebral circulation and are therefore effective agents for combating migraine.

They are also suitable for prophylaxis and combating the consequences of cerebral infarction events (apoplexia cerebri), such as apoplexy, cerebral ischaemias and cranio-cerebral trauma. The compounds according to the invention can also be employed for combating states of pain.

The present invention includes pharmaceutical formulations which comprise, in addition to non-toxic, inert pharmaceutically suitable carriers, one or more compounds according to the invention, or which consist of one or more active compounds according to the invention, and processes for the preparation of these formulations.

If appropriate, the active compound or compounds can also be present in microencapsulated form in one or more of the abovementioned carriers.

The therapeutically active compounds should preferably be present in the abovementioned pharmaceutical formulations in a concentration of about 0.1 to 99.5, preferably about 0.5 to 95% by weight of the total mixture.

The abovementioned pharmaceutical formulations can also comprise further pharmaceutical active compounds in addition to the compounds according to the invention.

In general, it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, to achieve the desired results. An individual dose preferably comprises the active compound or compounds according to the invention in amounts of about 1 to about 80, in particular 3 to 30 mg/kg of body weight.

Starting Compounds

EMBODIMENT OF THE INVENTION

Example I/1 A 5-(1,3-Dioxan-2-yl)-2-tributylstannyl-furan

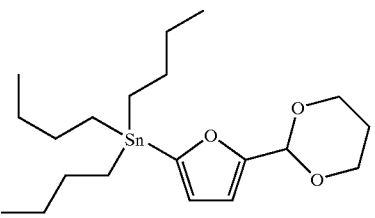

200 ml of sec-butyllithium (1.3M solution in cyclohexane, 260 mmol) were added dropwise to a solution of 34.4 g of 2-(2-furyl)-1,3-dioxane (224 mmol, obtainable from furfural and propane-1,3-diol) in 320 ml of THF at −70° C. in the course of 20 minutes. The solution was warmed at −20° C. for 30 minutes and then cooled again to −78° C. A solution of 60.8 ml of tributylstannyl chloride in 160 ml of THF was then added dropwise in the course of 30 minutes, after which the mixture was allowed to warm to room temperature. After 2.5 hours, water was added and the mixture was extracted with ethyl acetate. The organic phase was dried with magnesium sulphate and concentrated and the residue was distilled (boiling point$_{0.8}$180° C). 93 g were obtained.

Example I/2 A 3-(5-(1,3-Dioxan-2-yl)furan-2-yl)indazole

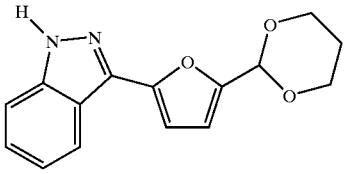

10 g (41 mmol) of 3-iodoindazole (U. Wrzeciono et al., Pharmazie 1979, 34, 20) are dissolved in 125 ml of DMF under argon, 0.7 g of Pd(PPh3)4 is added and the mixture is stirred for 15 minutes. 19.4 g (43.9 mmol) of 2-(5-tributylstannyl-2-furanyl)-1,3-dioxane are added and the mixture is stirred at 100° C. for 2 hours. The solvent is evaporated off in vacuo and the residue is chromatographed over silica gel using toluene and toluene/ethyl acetate mixtures as the eluent. 10 g (90.3% of theory) of 3-(2-(5-(1,3-dioxolan-2-yl)furyl)indazole are obtained.

Rf (SiO$_2$, toluene/ethyl acetate =4:1): 0.1

MS (ESI/POS): 271 (82, M+H), 213 (100), 157 (10)

EMBODIMENT II OF THE INVENTION

Example II/3 A 2-(1,3-Dioxan-2-yl)-6-trimethylstannylpyridine

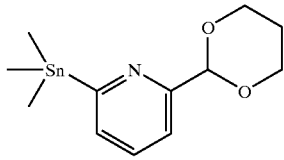

2 g (8.19 mmol) of 2-(1,3-dioxan-2-yl)-6-bromopyridine (R$_f$ (SiO$_2$, ethyl acetate): 0.67), obtainable from 6-bromo-2-pyridinecarboxaldehyde (Inorg. Chem. 1971, 10, 2474) and 1,3-propanediol, are initially introduced into 50 ml of ether, and 3.6 ml of a 2.5N solution of n-BuLi in hexane are added at −80° C. The mixture is stirred at −80° C. for 30 minutes and 1.8 g of trimethyltin chloride in 5 ml of ether are added. The mixture is first stirred at −80° C. and then allowed to come to −30° C. It is introduced into water and extracted with ethyl acetate, the organic phase is dried with sodium sulphate and the solvent is evaporated in vacuo. The product (1.1 g) can be employed for the next stage without further purification.

R$_f$ (SiO$_2$, ethyl acetate): 0.2

MS (CI): 330 (80, M+H), 166 (100).

Example II/4 A 3-(6-(1,3-Dioxan-2-yl)-2-pyridyl)indazole

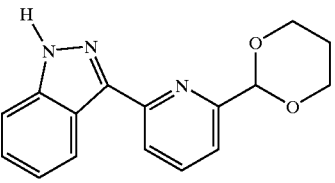

60 mg of Pd(PPh$_3$)$_4$ are added to 0.82 g (3.35 mmol) of 3-iodoindazole in 10 ml of DMF at room temperature under argon, and the mixture is stirred for 15 minutes. 1.1 g (3.35 mmol) of 2-(1,3-dioxan-2-yl)-6-trimethylstannylpyridine are added and the mixture is stirred at 100° C. for 4 hours. It is then evaporated in vacuo and the residue is chromatographed over silica gel. 300 mg (32% of theory) of an oil are obtained.

MS (CI/NH$_3$): 283 (100, M+H).

Example II/5 A

3-Iodoindazole

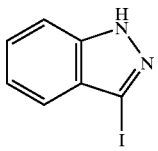

58.1 g of iodine (229 mmol) were introduced in portions into a suspension of 25.6 g of indazole (217 mmol) in 625 ml of methanol and 625 ml of 2N sodium hydroxide solution in the course of 1 hour. The mixture was stirred at room temperature for 3 days and 75 ml of concentrated hydrochloric acid were then added, while cooling with ice, the mixture was rendered acid with 2N hydrochloric acid and 20% strength sodium thiosulphate pentahydrate solution was added until the iodine colour disappeared. The precipitate which had separated out was filtered off with suction, washed neutral with water and dried in a vacuum drying cabinet at 50° C. For purification, the solid was taken up in methanol. After undissolved constituents had been filtered off, the filtrate was concentrated to dryness on a rotary evaporator, the product being obtained as an almost white solid.

Yield: 52.6 g (quantitative)

R$_f$ value: 0.63 (silica gel; cyclohexane/ethyl acetate 1:1)

Melting point: 137° C.

Example II/6 A

1-Benzyl-3-iodoindazole

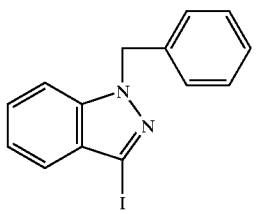

1.49 g of 95% pure sodium hydride (59.0 mmol) were added in portions to a solution of 12.0 g (49.2 mmol) of 3-iodoindazole in 100 ml of anhydrous tetrahydrofuran under argon. After the mixture had been stirred at room temperature for 45 minutes, 7.02 ml (59.0 mmol) of benzyl bromide were added dropwise. The mixture was stirred overnight at room temperature, and diethyl ether and water were then added. The organic phase was washed with saturated sodium chloride solution, dried over magnesium sulphate and concentrated to dryness on a rotary evaporator. The excess benzyl bromide was separated off by bulb tube distillation. The distillation residue gave a product in the form of an oil which gradually crystallized.

Yield: 15.4 g (94% of theory)

$R_f$ value: 0.78 (silica gel; cyclohexane/ethyl acetate 1:1)

Melting point: 54° C.

Example II/7 A

1-Benzyl-3-trimethylstannylindazole

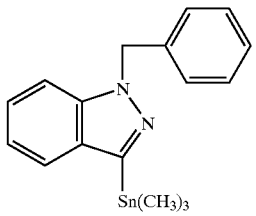

800 g of 1-benzyl-3-iodoindazole (24.0 mmol), 23.7 g of hexamethylditin (72.0 mmol) and 2.00 g of Pd(PPh$_3$)$_4$ (7.2 mol %) in 240 ml of anhydrous 1,4-dioxane were heated under reflux overnight in an argon atmosphere. The mixture was cooled to room temperature, 72 ml of 1M potassium fluoride solution and 200 ml of ethyl acetate were added and the mixture was stirred for 30 minutes. After the precipitate had been filtered off over Celite, the organic phase of the filtrate was washed with saturated sodium chloride solution, dried over magnesium sulphate and freed from the solvent on a rotary evaporator. The residue was stirred in n-pentane and the precipitate was filtered off with suction and dried at 50° C. under a high vacuum, whereupon the product was obtained in the form of a white solid.

Yield: 6.05 g (68%; purity: 88% according to GC)

$R_f$ value: 0.47 (silica gel; cyclohexane/ethyl acetate 10:1)

Melting point: 122° C.

MS-EI: 372 (Sn, M$^+$, 23), 357 (Sn, 56), 207 (100), 165 (Sn, 61), 91 (68).

Abbreviations:

| | |
|---|---|
| Ph = | phenyl |
| Et = | ethyl |
| Me = | methyl |
| EE = | ethyl acetate |
| H = | hexane |
| PE = | petroleum ether |
| MeOH = | methanol |
| E = | ether |
| DMF = | dimethylformamide |
| Ac = | acetyl |
| KOH = | potassium hydroxide |
| NMP = | N-methylpyrrolidone |

EMBODIMENT OF THE INVENTION

Example III/8 A

1-Benzyl-3-iodoindazole

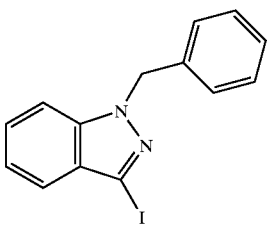

A solution of 2.99 g of iodoindazole (12.25 mmol) in 10 ml of THF was added dropwise to a suspension of 515 mg of NaH (60% in oil, 12.88 mmol) in 20 ml of THF. After 15 minutes, 1.55 ml of benzyl bromide were added. After 6 hours at room temperature and 3 hours at 40° C. water was added to the reaction mixture and the mixture was extracted with ether. The organic phases were dried with sodium sulphate and concentrated. After chromatography (SiO$_2$; petroleum ether:ethyl acetate 9:1), 3.351 g of a viscous oil which solidifies in vacuo were obtained.

Melting point: 51.5–52.50° C.

$R_f$=0.38 (hexane/ethyl acetate 3:1)

Example III/9 A

1-Benzyl-3-cyanoindazole

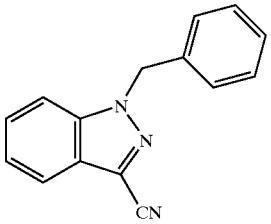

420 mg of NaH (60% in oil, 10.3 mmol) were added in portions to 1.0 g of 3-cyanoindazole (7.0 mmol) and 1.7 ml of benzyl bromide (14.0 mmol) in 6 ml of THF, and the mixture was stirred at room temperature for 15 hours. The reaction was quenched with 2 drops of water, the mixture was concentrated and the residue was chromatographed (SiO$_2$; petroleum ether:ethyl acetate 3:1). 1.3 g of a solid were obtained.

Melting point: 91° C.

Example III/10 A

1-Benzyl-3-trimethylstannyl-indazole:

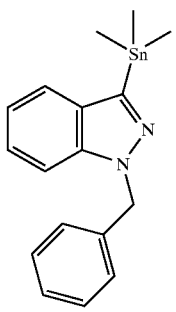

1.67 g of 1-benzyl-3-iodoindazole (5.00 mmol), 4.95 g of hexamethylditin (15.0 mmol) and 530 mg of Pd(PPh$_3$)$_4$ (10 mol%) were heated under reflux in 50 ml of anhydrous 1,4-dioxane overnight. The mixture was cooled to room temperature, 15 ml of 1M potassium fluoride solution and 50 ml of ethyl acetate were added and this mixture was stirred for 30 minutes. After the precipitate had been filtered off, the organic phase of the filtrate was washed with water, dried over magnesium sulphate and freed from the solvent on a rotary evaporator. Drying of the residue at 50° C. under a high vacuum gave the product in the form of a white solid, which could be employed in the subsequent Pd-catalysed couplings without further purification.

Yield: 78%

R$_f$: 0.32 (silica gel; cyclohexane/ethyl acetate 16:1)

MS-EI: 372 (Sn, M$^+$, 23), 357 (Sn, 56), 207 (100), 165 (Sn, 61), 91 (68).

EMBODIMENT IV OF THE INVENTION

Example IV/11 A 5-(1,3-Dioxan-2-yl)-2-tributylstannyl-furan

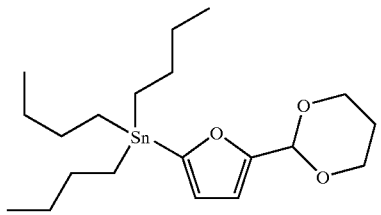

200 ml of sec-butyllithium (1.3M solution in cyclohexane, 260 mmol) were added dropwise to a solution of 34.4 g of 2-(2-furyl)-1,3-dioxane (224 mmol, obtainable from furfural and propane-1,3-diol) in 320 ml of THF at −70° C. in the course of 20 minutes. The solution was warmed at −20° C. for 30 minutes and then cooled again to −78° C. A solution of 60.8 ml of tributylstannyl chloride in 160 ml of THF was then added dropwise in the course of 30 minutes, after which the mixture was allowed to warm to room temperature. After 2.5 hours, water was added and the mixture was extracted with ethyl acetate. The organic phase was dried with magnesium sulphate and concentrated and the residue was distilled (boiling point$_{0.8}$ 1 80° C.). 93 g were obtained.

Example IV/12 A 3-(5-(1,3-Dioxolan-2-yl)furan-2-yl)indazole

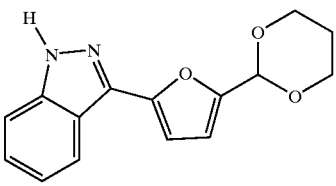

10 g (41 mmol) of 3-iodoindazole (U. Wrzeciono et al., Pharmazie 1978, 34, 20) are dissolved in 125 ml of DMF under argon, 0.7 g of Pd(PPh$_3$)$_4$ is added and the mixture is stirred for 15 minutes. 19.4 g (43.9 mmol) of 2-(5-tributylstannyl-2-furanyl)-1,3-dioxolane are added and the mixture is stirred at 100° C. for 2 hours. The solvent is evaporated off in vacuo and the residue is chromatographed over silica gel using toluene and toluene/ethyl acetate mixtures as the eluent. 10 g (90.3% of theory) of 3-(2-(5-(1,3-dioxolan-2-yl)furyl)indazole are obtained.

R$_f$ (SiO$_2$, toluene/ethyl acetate=4:1): 0.1.

Preparation Examples

EMBODIMENT I OF THE INVENTION

Example I/1

3-(5-(1,3-Dioxan-2-yl)furan-2-yl)-1-(4-picolyl) indazole

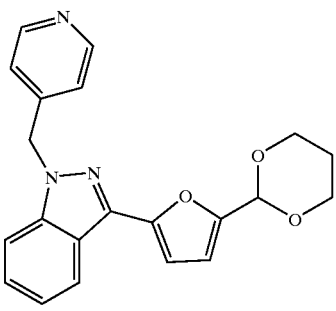

A solution of 2 g (7.41 mmol) of 3-(5-(1,3-dioxan-2-yl) furan-2-yl)indazole in 10 ml of DMF is added to a suspension of 355 mg of NaH (60 per cent in paraffin) in 10 ml of DMF under argon, and the mixture is stirred at room temperature for 1 hour. 1.46 g of 4-picolyl chloride hydrochloride are then added, followed by 355 mg of NaH (60 per cent in paraffin). The mixture is stirred at room temperature for 1 hour and then at 100° C. for 1 hour, introduced into water and extracted with ethyl acetate, the organic phase is dried with sodium sulphate and evaporated in vacuo and the residue is chromatographed over silica gel using toluene/ ethyl acetate mixtures as the eluent. 1 g (37% of theory) of an oil is obtained.

R$_f$ (SiO$_2$, ethyl acetate): 0.25

Example I/2

3-(5-Formyl-2-furyl)-1-(4-picolyl)indazole

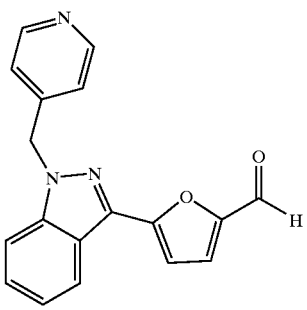

1 g (2.77 mmol) of 3-(5-(1,3-dioxan-2-yl)furan-2-yl) -1-(4-picolyl)indazole is dissolved in 10 ml of acetone, and 20 ml of 50 per cent strength acetic acid are added. The mixture is boiled for 1 hour, introduced into water and extracted with ethyl acetate and the organic phase is dried with sodium sulphate and evaporated in vacuo to give 0.8 g (95.3% of theory) of an oil.

$R_f$ (SiO$_2$, ethyl acetate): 0.25

Example I/13

3-(2-(5-Hydroxymethylfuryl))-1-(4-picolyl)indazole

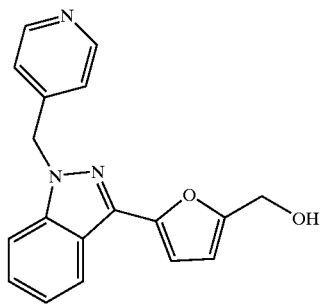

0.4 g (1.3 mmol) of 3-(5-formyl-2-furanyl)-1-(4-picolyl) indazole is suspended in 20 ml of propanol, and 0.4 g of NaBH$_4$ is slowly added at 0° C. After the mixture has been stirred at room temperature for 1 hour, the clear solution is introduced into water and extracted with ethyl acetate, the organic phase is dried with sodium sulphate and evaporated in vacuo and the residue is chromatographed over silica gel using toluene/ethyl acetate mixtures as the eluent. 200 mg (50% of theory) of crystals are obtained.

Melting point 183° C.

Rf (SiO$_2$, ethyl acetate): 0.14

The compounds listed in Tables I/1, I/2 and I/3 are prepared analogously to the instructions of Examples I/1, I/2 and I/3:

TABLE I/1

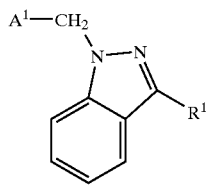

| Ex. No. | A$^1$ | R$^1$ | R$_f$*/mp ° C. | Yield (% of theory) |
|---|---|---|---|---|
| I/4 | 3-pyridyl-CH | 5-(hydroxymethyl)-2-furyl | 0.1 (E)/oil | 10 |
| I/5 | 2-furyl | 5-(hydroxymethyl)-2-furyl | 0.52 (T4E1)/ 120° C. | 70 |

TABLE I/1-continued
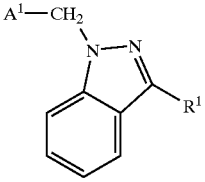
| Ex. No. | A¹ | R¹ | R_f*/mp ° C. | Yield (% of theory) |
|---|---|---|---|---|
| I/6 | 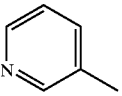 | 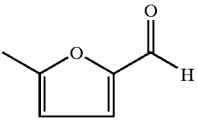 | 0.2 (E)/oil | 2 |
| I/7 | 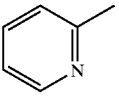 | 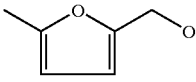 | 0.06 (T1E1)/ 103° C. | 53 |
| I/8 | 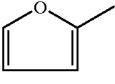 | 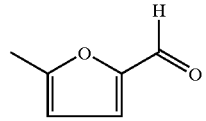 | 0.46 (T4E1)/ 119° C. | 71 |
| I/9 | 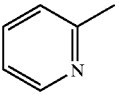 | 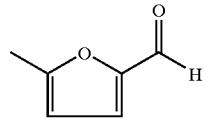 | 0.25 (T1E1)/ 105° C. | 37 |
| I/10 | 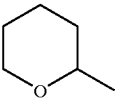 | 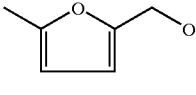 | 0.35 (T1E1)/ oil | 80 |
| I/11 | 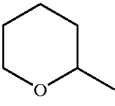 | 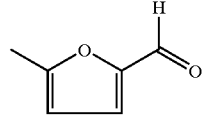 | 0.38 (T4E1)/ 112° C. | 69 |
| I/12 | 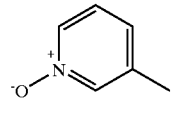 | 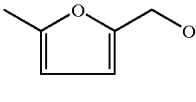 | 0.14 (E4MeOH1)/ oil | 50 |
| I/13 | 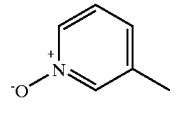 | 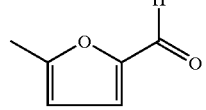 | 157° C. | 75 |
| I/14 | 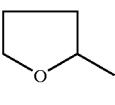 | 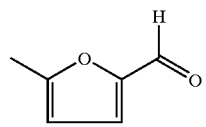 | 0.46 (T1E1)/ oil | 50 |
| I/15 |  | 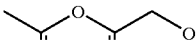 | 0.27 (T1E1)/ oil | 88.6 |

TABLE I/3

| Ex. No. | Structure | Yield/% of theory m.p. °C. | $R_f$ |
|---|---|---|---|
| I/26 | | 52% 152° C. | 0.31 (H:E 1:1) |
| I/27 | | 82% 147° C. | 0.25 (Cy:E 2:1) |
| I/28 | | 74% | 0.41 (H:E 1:1) |
| I/29 | | 85% 162° C. | 02.9 (H:E 1:1) |

TABLE I/3-continued
| Ex. No. | | Yield/% of theory m.p. °C. | $R_f$ |
|---|---|---|---|
| I/30 | 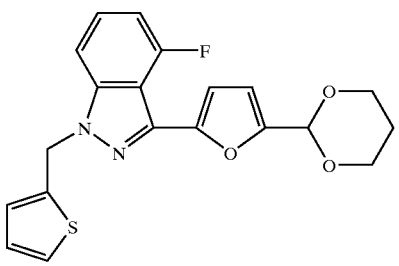 | 83% 125° C. | 0.028 (H:E 3:1) |
| I/31 | 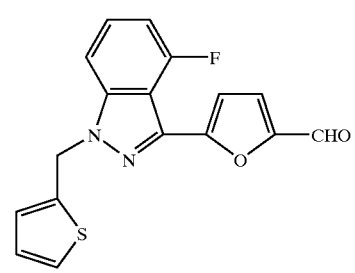 | 87% 132° C. | 0.52 (H:E 1:1) |
| I/32 | 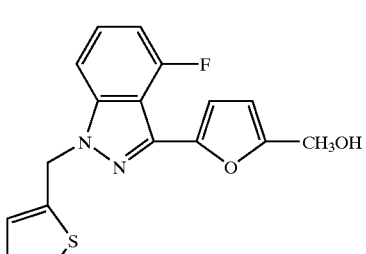 | 42% 200° C. | 0.41 (H:E 1:1) |
| I/33 | 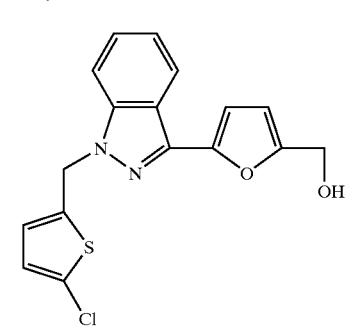 | | |
E = ethyl acetate
H = hexane
Cy = cyclohexane

EMBODIMENT II OF THE INVENTION

Example II/34

1-Benzyl-3-(6-(1,3-dioxan-2-yl)-2-pyridyl)indazole

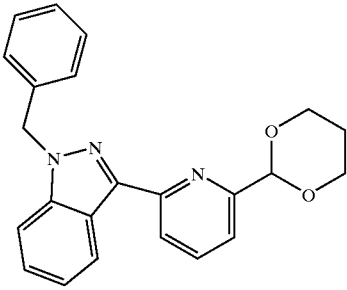

580 mg of NaH (60 per cent strength in paraffin) are slowly added to 3.7 g (13.1 mmol) of 3-(6-(1,3-dioxan-2-yl)-2-pyridyl)indazole in THF under argon. After the mixture has been stirred for 30 minutes, 1.71 ml of benzyl bromide are added and the mixture is stirred at room temperature for 1 hour. It is then introduced into water and extracted with ethyl acetate, the organic phase is dried with magnesium sulphate and evaporated in vacuo and the residue is chromatographed over silica gel and eluted with ethyl acetate/toluene mixtures. 1.52 g (31% of theory) of an oil are obtained.

$R_f$ (SiO$_2$, ethyl acetate): 0.3

MS 372 (100, M+1)

Example II/35

1-Benzyl-3-(6-formyl-2-pyridyl)indazole

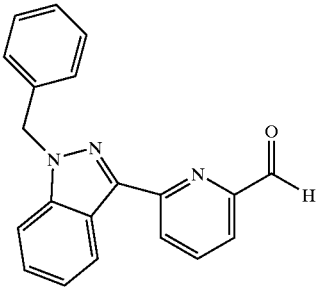

1.52 g (4.1 mmol) of 1-benzyl-3-(6-(1,3-dioxan-2-yl)-2-pyridyl)indazole are dissolved in 10 ml of acetone, and 20 ml of 50 per cent strength acetic acid are added. The mixture is stirred at 50° C. for 3 hours, introduced into water and extracted with ethyl acetate, the organic phase is dried with sodium sulphate and evaporated in vacuo and the residue is chromatographed over silica gel using toluene/ethyl acetate mixtures to give 180 mg (14% of theory) of an oil.

$R_f$ (SiO$_2$, toluene/ethyl acetate): 0.7

MS (CI/NH$_3$): 314 (100, M+H).

Example II/36

1-Benzyl-3-(6-hydroxymethyl-2-pyridyl)indazole

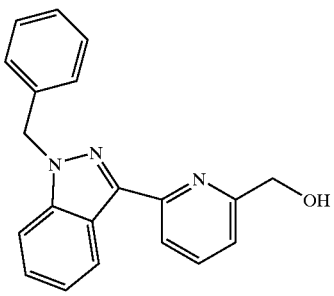

180 mg (0.57 mmol) of 1-benzyl-3-(6-formyl-2-pyridyl) indazole are suspended in 20 ml of propanol, and 180 mg of NaBH$_4$ are slowly added. After the mixture has been stirred at room temperature for 30 minutes, the clear solution is introduced into water and extracted with ethyl acetate, the organic phase is dried with sodium sulphate and evaporated in vacuo and the residue is chromatographed over silica gel using toluene/ethyl acetate mixtures as the eluent.

120 mg (66% of theory) of crystals are obtained.

Melting point 75° C.

$R_f$ (SiO$_2$, ethyl acetate): 0.15

MS (CI, NH$_3$): 316 (100, M+H).

Example II/37

1-Benzyl-3-(2-pyrimidyl)indazole

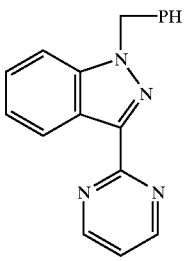

200 mg of 1-benzyl-3-trimethylstannylindazole (crude product, 70% according to GC), 35 mg of 2-chloropyrimidine (0.30 mmol) and 29 mg (0.025 mmol) of Pd(PPh$_3$)$_4$ in 2.5 ml of toluene were heated under reflux overnight in an argon atmosphere. The mixture was cooled to room temperature, saturated ammonium chloride solution was added and the mixture was extracted with ethyl acetate. The organic phase was dried over magnesium sulphate and freed from the solvent on a rotary evaporator. Purification was carried out by chromatography over aluminium oxide using cyclohexane/ethyl acetate as the eluent (gradient from 10:1 to 1:1).

Yield: 80 mg (93%)

$R_f$ value: 0.67 (aluminium oxide; cyclohexane/ethyl acetate 10:1)

Melting point: 154° C.

MS-EI: 286 (M$^+$, 100), 285 (64), 209 (40), 91 (71)

Example II/38

1-Benzyl-3-(4,5-dimethyl-2-pyrimidyl)indazole

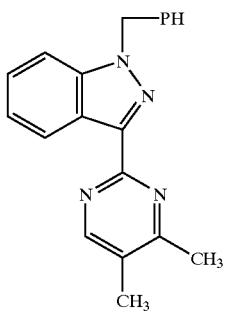

640 mg of 1-benzyl-3-trimethylstannylindazole (1.72 mmol), 212 mg of 2-chloro-4,5-dimethylpyrimidine* (1.49 mmol) and 72 mg (0.10 mmol) of $Pd(PPh_3)_2Cl_2$ (5.8 mol %) in 20 ml of toluene were heated under reflux overnight in an argon atmosphere. The mixture was cooled to room temperature, saturated ammonium chloride solution was added and the mixture was extracted with ethyl acetate. The organic phase was dried over magnesium sulphate and freed from the solvent on a rotary evaporator. Purification was carried out by chromatography over silica gel using cyclohexane/ethyl acetate as the eluent (gradient from 10:1 to 1:1).

*Sugasawa et al., Yakugaku Zasshi, 71, 1951, 1345, 1348, Chem. Abstr., 1952, 8034.

Yield: 239 mg (51% of theory)
$R_f$ value: 0.33 (silica gel; cyclohexane/ethyl acetate 1:1)
Melting point: 190° C.

The examples listed in Tables II/1, II/2 and II/3 were prepared analogously to the instructions of Examples II/34–38:

TABLE II/1

| Ex. No. | Structure | $R_f$-value (silica gel; Cy:EE 1:1) or melting point [° C.] | Yield % of theory |
|---|---|---|---|
| II/39 | 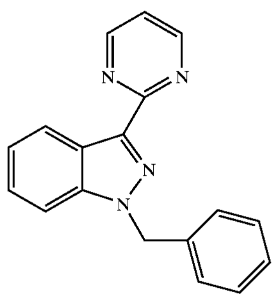 | 154 | 93 |
| II/40 | 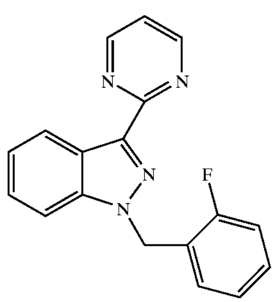 | 0.27 | 46 |
| II/41 | 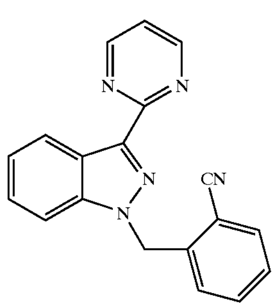 | 0.16 | 78 |

TABLE II/1-continued

| Ex. No. | Structure | R$_f$-value (silica gel; Cy:EE 1:1) or melting point [° C.] | Yield % of theory |
|---|---|---|---|
| II/42 | 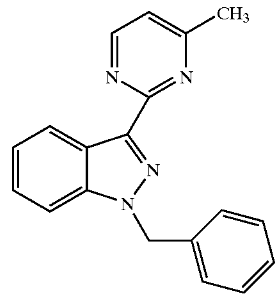 | 0.20 | 19 |
| II/43 | 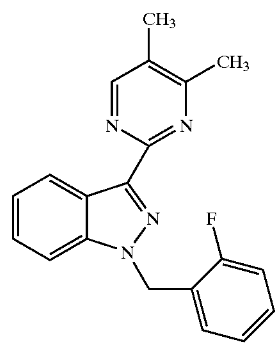 | 0.26 | 24 |
| II/44 | 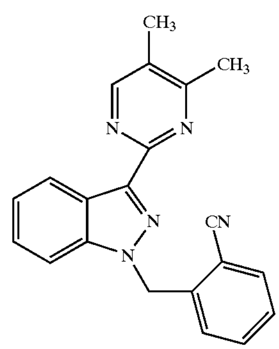 | 0.16 | 43 |
| II/45 | 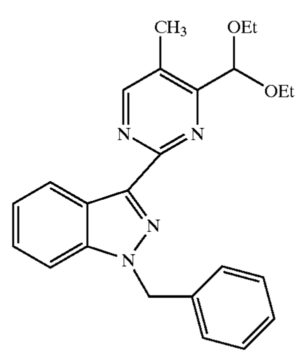 | 0.35 | 30 |

TABLE II/1-continued

| Ex. No. | Structure | R_f-value (silica gel; Cy:EE 1:1) or melting point [° C.] | Yield % of theory |
|---|---|---|---|
| II/46 | (4,5,6-trimethylpyrimidin-2-yl on 1-benzyl-indazol-3-yl) | 0.26 | 18 |
| II/47 | (5-chloro-4,6-dimethylpyrimidin-2-yl on 1-benzyl-indazol-3-yl) | 0.65 | 41 |
| II/48 | (5-chloro-4-methylamino-pyrimidin-2-yl on 1-benzyl-indazol-3-yl) | 0.17 | 11 |
| II/49 | (5-cyano-4-amino-pyrimidin-2-yl on 1-benzyl-indazol-3-yl) | 0.28 | 34 |

TABLE II/1-continued

| Ex. No. | Structure | $R_f$-value (silica gel; Cy:EE 1:1) or melting point [° C.] | Yield % of theory |
|---|---|---|---|
| II/50 | 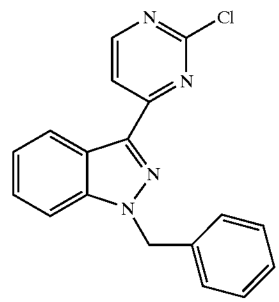 | 0.76 | 64 |
| II/51 | 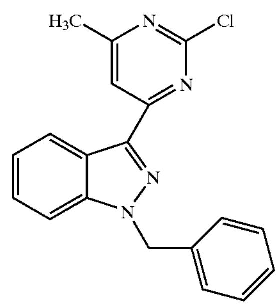 | 0.72 | 19 |
| II/52 | 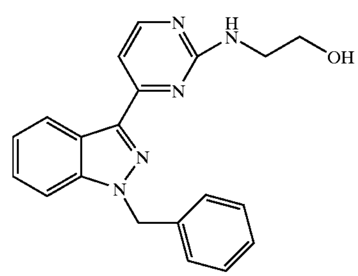 | 0.95 | 47 |
| II/53 | 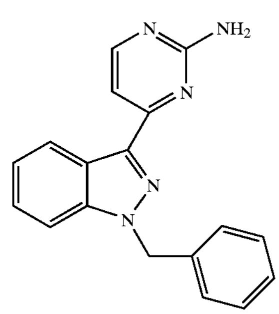 | 0.03 (Cy:EE 4:1) | 53 |
| II/54 | 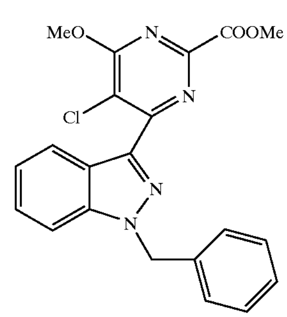 | 0.87<br>210° C. | 45 |

TABLE II/1-continued

| Ex. No. | Structure | R_f-value (silica gel; Cy:EE 1:1) or melting point [° C.] | Yield % of theory |
|---|---|---|---|
| II/55 | 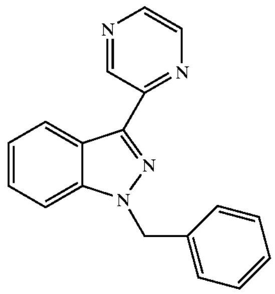 | 0.67 118° C. | 86 |
| II/56 | 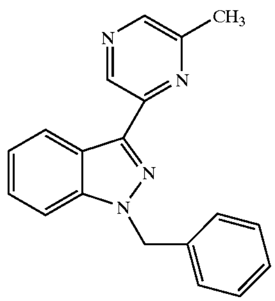 | 0.61 122° C. | 19 |
| II/57 | 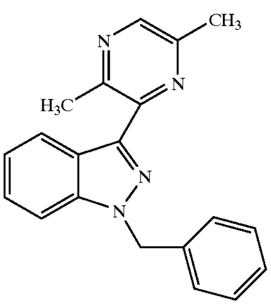 | 0.61 105° C. | 51 |
| II/58 | 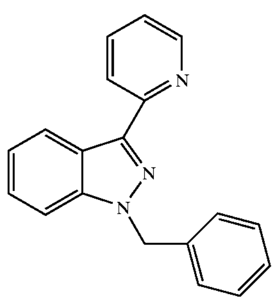 | 0.50 | 23 |
| II/59 | 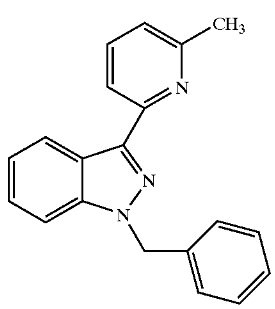 | 0.80 | 26 |

TABLE II/1-continued

| Ex. No. | Structure | R$_f$-value (silica gel; Cy:EE 1:1) or melting point [° C.] | Yield % of theory |
|---|---|---|---|
| II/60 | (3-(4,6-dimethyl-3-cyanopyridin-2-yl)-1-benzyl-1H-indazole) | 0.73<br>129° C. | 68 |
| II/61 | (3-(4-chloro-6-methylpyridin-2-yl)-1-benzyl-1H-indazole) | 0.84<br>102° C. | 42 |
| II/62 | (3-(6-(hydroxymethyl)pyridin-2-yl)-1-(2-fluorobenzyl)-1H-indazole) | 99° C. | |

TABLE II/2

| Ex. No. | Structure | R$_f$ value (silica gel; Cy:EE 1:1) | Melting point [° C.] | Yield [% of theory] |
|---|---|---|---|---|
| II/63 | (3-(4-amino-5-fluoropyrimidin-2-yl)-1-(2-fluorobenzyl)-1H-indazole) | 0.23 | 250 | 34 |

EMBODIMENT III OF THE INVENTION

Example III/69

1-Benzyl-3-(1-methyl-imidazol-2-yl)-indazole

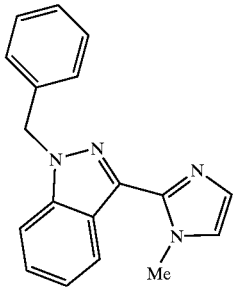

2.50 g of 1-benzyl-3-iodoindazole (7.48 mmol), 3.33 g of 1-methyl-2-tributyl-stannylimidazole (8.98 mmol) (K. Gaare, K. Undheim et al, *Acta Chem. Scand.* 1993, 47, 57) and 432 mg of tetrakis-triphenylphosphinepalladium (0.37 mmol) in 10 ml of DMF were heated at 80° C. for 2 days under argon. After cooling, water was added to the mixture and the mixture was extracted with ethyl acetate. The organic phases were dried with sodium sulphate and concentrated. After chromatography ($SiO_2$; $CH_2Cl_2$:MeOH 100:1), 2.40 g of an oil were obtained.

MS: (CI, $NH_3$): 289 (M+H$^+$, 100).

Example III/70

Ethyl 2-(1-benzyl-indazol-3-yl)-oxazole-5-carboxylate

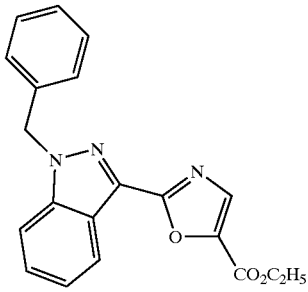

A solution of ethyl diazopyruvate (250 mg, 1.76 mmol) (T. Ohsumi & H. Neunhofer, *Tetrahedron* 1992, 48, 5227) in 4 ml of benzene was added dropwise to a refluxing solution of 600 mg of 1-benzyl-3-cyanoindazole (2.57 mmol) and 0.8 mg of copper(II) acetylacetonate (3 mmol) in 1 ml of benzene in the course of 4 hours. Thereafter, the reaction mixture was heated under reflux for a further 15 minutes, cooled and evaporated in vacuo. The residue was chromatographed ($SiO_2$; cyclohexane:ethyl acetate 3:1). 67 mg of a yellow oil were obtained.

$R_f$=0.11 (hexane/ethyl acetate 3:1).

Example III/71

1-Benzyl-3-(5-hydroxymethyl-oxazol-2-yl)-indazole

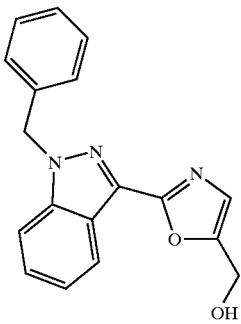

18 mg of lithium aluminium hydride (0.47 mmol) were added to a solution of 67 mg of ethyl 2-(1-benzyl-indazol-3-yl)-oxazole-5-carboxylate in 2 ml of ether at 0° C. After 3 hours at 0° C., the reaction mixture was stirred at room temperature for a further 24 hours, water was then added and the mixture was extracted 3 times with ether. The organic phases were dried with sodium sulphate and concentrated. After chromatography ($SiO_2$; cyclohexane:ethyl acetate 2:1 to 3:2), 12 mg of a white solid were obtained.

$R_f$=0.12 (hexane/ethyl acetate 1:1).

Example III/72

Ethyl 2-(1-benzyl-indazol-3-yl)-thiazole-4-carboxylate

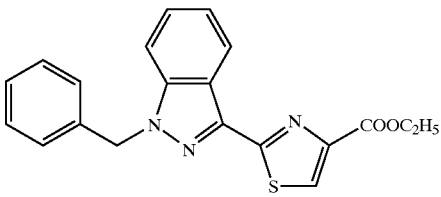

148 mg of 1-benzyl-3-trimethylstannyl-indazole (0.399 mmol), 86 mg of ethyl 2-bromothiazole-4-carboxylate (0.364 mmol) (Erlenmeyer et al. Helv. Chim. Acta 1942 (25) 1073) and 42 mg of Pd(PPh$_3$)$_4$ were stirred in 2 ml of DMF under argon at 80° C. for 2 days. After cooling, water was added to the mixture and the mixture was extracted with ethyl acetate. The organic phases were dried with sodium sulphate and concentrated. After chromatography ($SiO_2$; petroleum ether:ethyl acetate 3:1), 75 mg of a white solid (52%) were obtained.

$R_f$: 0.31 (hexane:ethyl acetate 3:1).

Melting point: 95–96° C.

The compounds listed in Table III/1 were prepared analogously to the instructions given above:

TABLE III/1

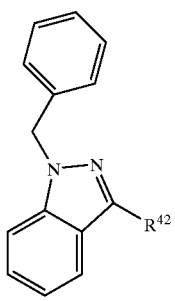

| Ex. No. | R42 | Rf*/Mobile phase | Yield (% of theory) |
|---|---|---|---|
| III/73 | 2-methyl-4-methyl oxazole | 0.14 (H:E 3:1) Melting point 77° C. | 26 |
| III/74 | 2-methyl thiazole | 0.25 (H:E 3:1) Melting point 77° C. | 37 |

H: hexane
E: ethyl acetate

The compounds listed in Table III/2 were prepared either analogously to the instructions given above or obtained via the corresponding indazole derivatives

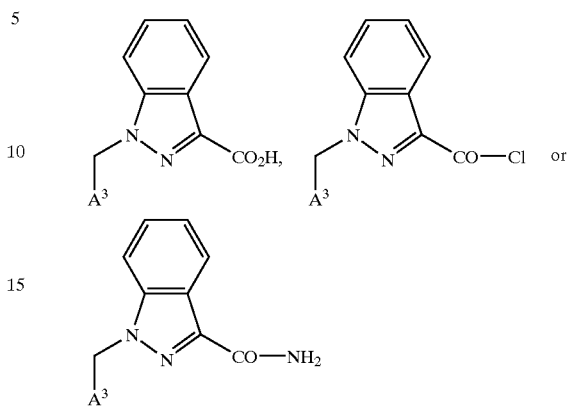

(identified in what follows by indazole-$CO_2H$, indazole-CO—Cl or indazole-CO—$NH_2$) by the process variants described under [A3]-[G3].

TABLE III/2

| Ex. No. | Structure | Preparation method | Yield/ melting point° C. | Rf |
|---|---|---|---|---|
| III/75 | (indazole-oxazole-CH2OH with Ph, CH3) | * [D3] | 65% from OAc/ 128° C. | 0.17 ($CH_2Cl_2$ MeOH 100:5) |
| III/76 | (indazole-oxadiazole-CH2OH with 2-F-benzyl) | * [G3] | 86% from OAc/ 138° C. | 0.12 ($CH_2Cl_2$ MeOH 100:5) |
| III/77 | (indazole-oxazole-CH2OAc with Ph, CH3) | * [D3] | 24%/ | 0.15 (H:EE 3:1) |

TABLE III/2-continued

| Ex. No. | Structure | Preparation method | Yield/ melting point° C. | $R_f$ |
|---|---|---|---|---|
| III/78 | 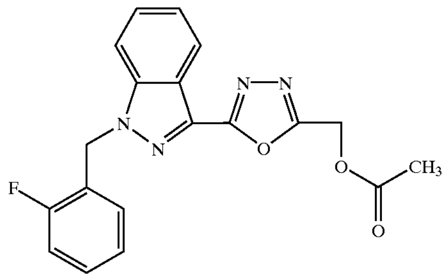 | * [G3] | 92%/ 107° C. | 0.16 (H:EE 3:1) |
| III/79 | 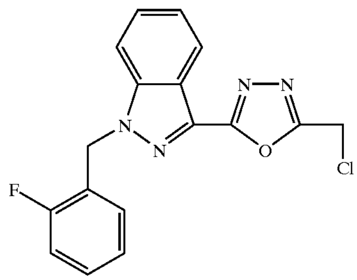 | * [G3] | 52%/ 111° C. | 0.77 (CH$_2$Cl$_2$ MeOH 100:5) |
| III/80 | 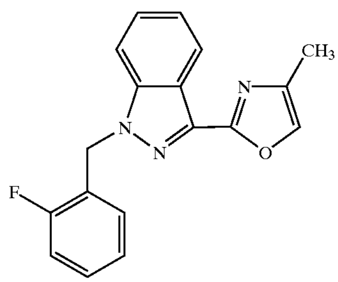 | [B3] | 24%/ 106° C. | 0.22 (H:EE 3:1) |
| III/81 | 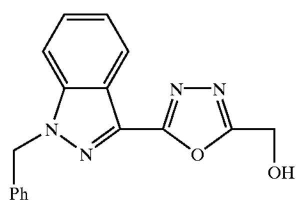 | * [G3] | 50%/ 153° C. | 0.22 (DCM:MeOH 100:5) |
| III/82 | 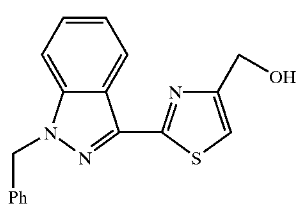 | [B3] | 41%/ 150° C. | 0.11 (H:EE 3:1) |
| III/83 | 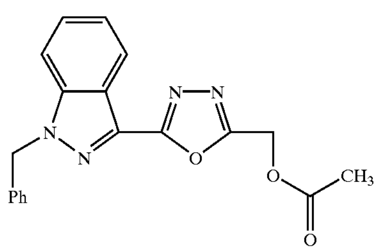 | * [G3] | 35%/ 135° C. | 0.69 (DCM MeOH 100:5) |

TABLE III/2-continued

| Ex. No. | Structure | Preparation method | Yield/ melting point° C. | $R_f$ |
|---|---|---|---|---|
| III/84 | 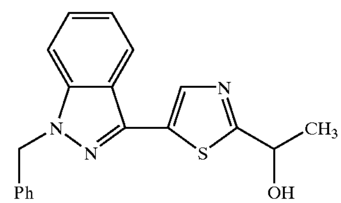 | [A3] ]B3] + removal of protective groups | 40%/ 94° C. | 0.24 DCM:M 100:5) |
| III/85 | 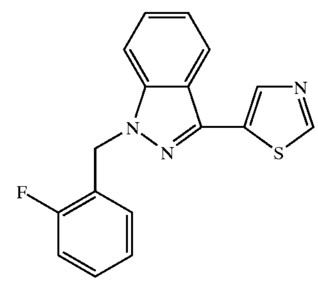 | [A3] | 20%/ 87° C. | 0.43 (DCM:M 100:5) |
| III/86 | 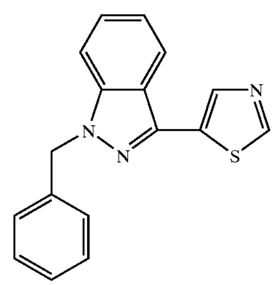 | [A3] | 9%/ 76° C. | 0.44 (DCM:M 100:2) |
| III/87 | 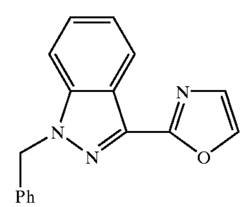 | * [E3] | 22%/ 80° C. | 0.70 (DCM:M 100:5) |
| III/88 | 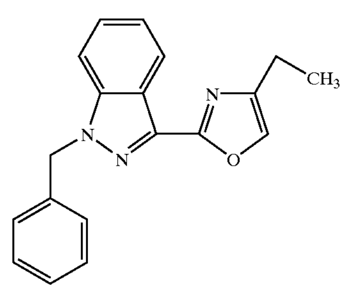 | * [F4] | 5.5%/ 60° C. | 0.63 (H:EE 1:1) (Alox) |

TABLE III/2-continued

| Ex. No. | Structure | Preparation method | Yield/ melting point° C. | $R_f$ |
|---|---|---|---|---|
| III/89 | 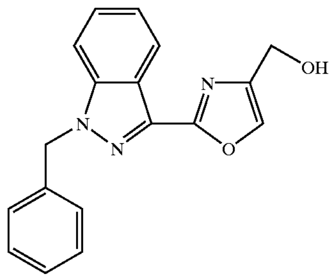 | * [F3]+ reduction | 36%/ 122° C. | 0.24 (CH$_2$Cl$_2$ CH$_3$OH 100:1) |
| III/90 | 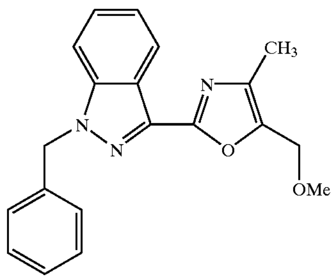 | * [D3] | 40% | 0.08 (H:EE 3:1) |
| III/91 | 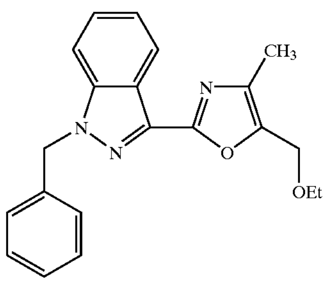 | * [D3] | 44% | 0.43 (H:EE 1:1) |
| III/92 | 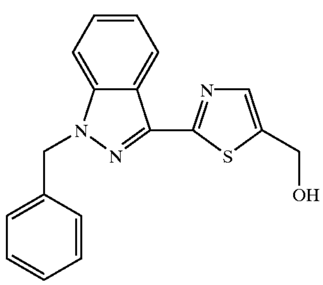 | [B3] + removal of protective groups | ~100% 121° C. | 0.09 (CH$_2$Cl$_2$ CH$_3$OH 100:1) |
| III/93 | 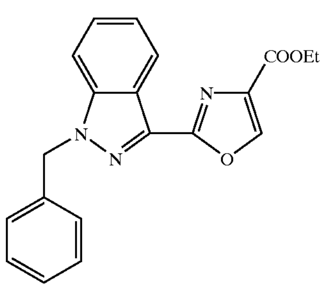 | * [F3] | 19% | 0.29 (CH$_2$Cl: CH$_3$OH 100:1) |

TABLE III/2-continued

| Ex. No. | Structure | Preparation method | Yield/ melting point° C. | $R_f$ |
|---|---|---|---|---|
| III/94 | 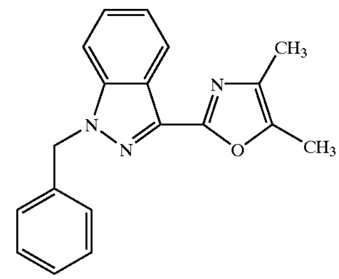 | * [F3] | 14%/ 109° C. | 0.87 (CH$_2$Cl$_2$ CH$_3$OH 100:1) (Alox) |
| III/95 | 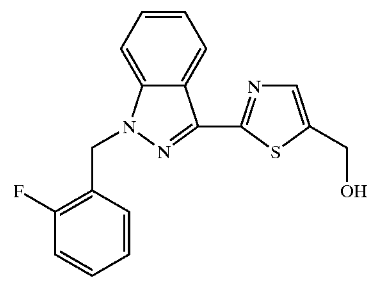 | [B3]+ removal of protective groups | 57% 139° C. | 0.10 (CH$_2$C$_2$ CH$_3$OH 100:1) |
| III/96 | 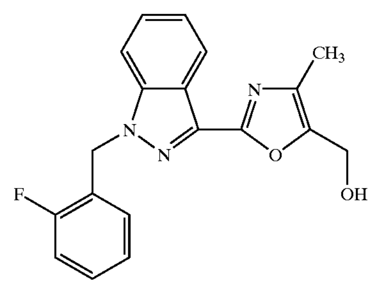 | * [D3] | 59% 144° C. | 0.21 (H:EE 1:1) |
| III/97 | 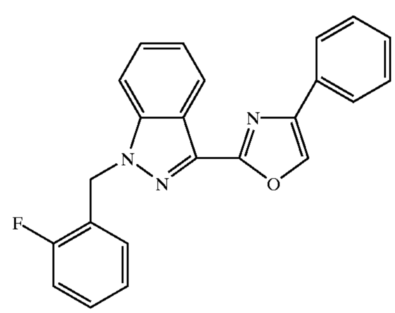 | * [F3] | 11% | 0.43 (PE:EE 1:1) Alox |
| III/98 | 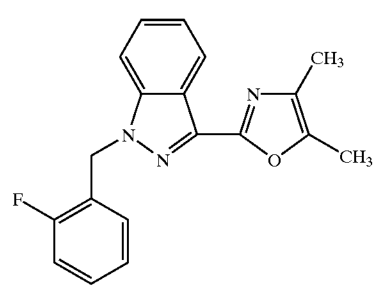 | * [F3] | 13% 145° C. | 0.67 (H:EE 3:1) |

TABLE III/2-continued

| Ex. No. | Structure | Preparation method | Yield/ melting point° C. | $R_f$ |
|---|---|---|---|---|
| III/99 | 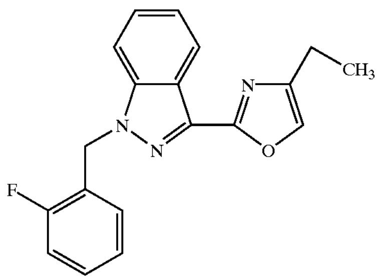 | *<br>[F] | 16%<br>73° C. | 0.47<br>(H:EE 3:1)<br>Alox |

\* = build up from indazole—COCl or indazole-COOH or indazole—C(=O)NH$_2$

[ ] = see process equation

TABLE III/3

| Ex. No. | Structure | Preparation method | Yield/ melting point ° C. | $R_f$ |
|---|---|---|---|---|
| III/100 | 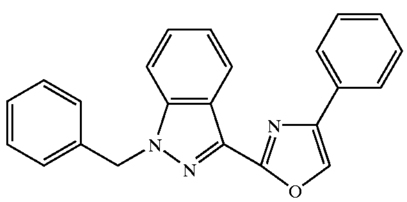 | F3 | 11% | 0.47<br>(PE/E 1:1)<br>Al$_2$O$_3$ |
| III/101 | 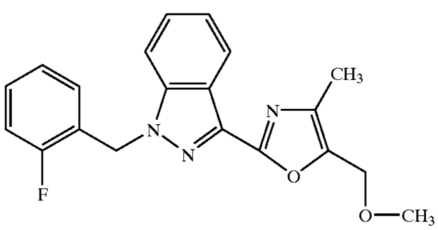 | D3 | 20%<br>87° C. | 0.18<br>(100 1) |
| III/102 | 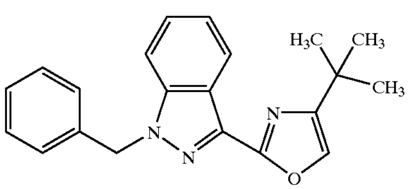 | F3 | 20%<br>— | 0.26<br>(PE/E 5:1)<br>Al$_2$O$_3$ |
| III/103 | 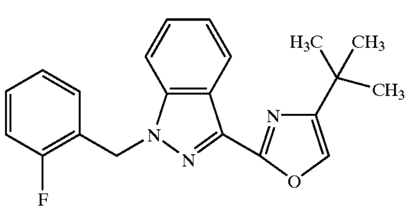 | F3 | 8.5%<br>75° C. | 0.27<br>(Hex/EE 1:1) |

TABLE III/3-continued

| Ex. No. | Structure | Preparation method | Yield/ melting point ° C. | $R_f$ |
|---|---|---|---|---|
| III/ 104 | 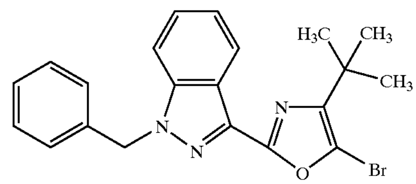 | F3 by-product | 9.5 — | 0.368 (PE/E 5:1) Al₂O₃ |
| III/ 105 | 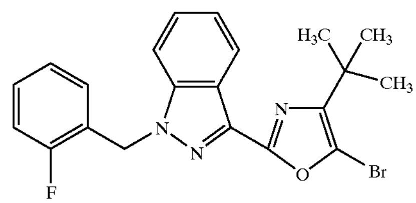 | F3 by-product | 12% — | 0.381 (PE/E 5:1) Al₂O₃ |
| III/ 106 | 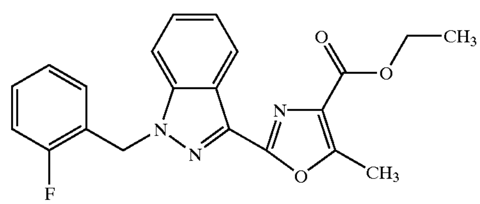 | H3 | 75% 188° C. | 0.21 (Hex/EE 3:1) Al₂O₃ |
| III/ 107 | 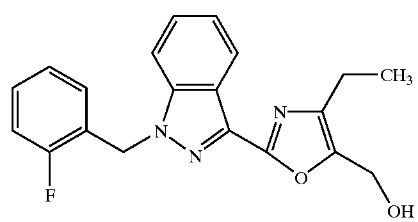 | D3 | 52% 138° C. | 0.09 (Cyclo/ EE 2:1) Al₂O₃ |
| III/ 108 | 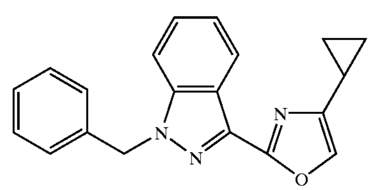 | F3 | 11% 71° C. | 0.486 (PE/E 1:1) Al₂O₃ |
| III/ 109 | 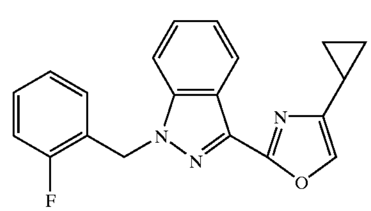 | F3 | 10% | 0.625 (PE/E 1:1) Al₂O₃ |
| III/ 110 | 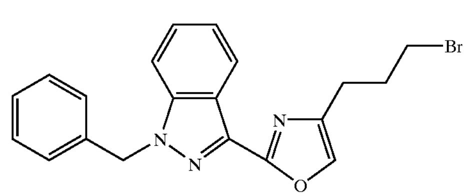 | F3 by-product | 12% 72° C. | 0.399 (PE/E 1:1) Al₂O₃ |

TABLE III/3-continued

| Ex. No. | Structure | Preparation method | Yield/ melting point ° C. | R_f |
|---|---|---|---|---|
| III/111 | 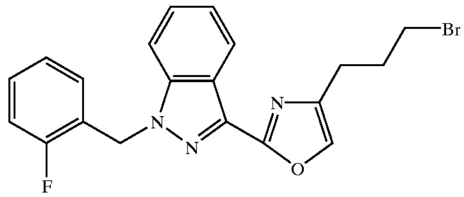 | F3 by-product | 8.5% — | 0.581 (PE/E 1:1) Al$_2$O$_3$ |
| III/112 | 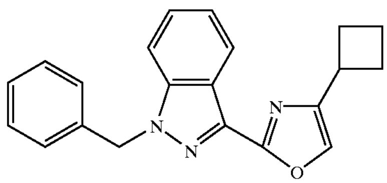 | F3 | 15% 86° C. | 0.41⁻ (PE/E 1:1) Al$_2$O$_3$ |
| III/113 | 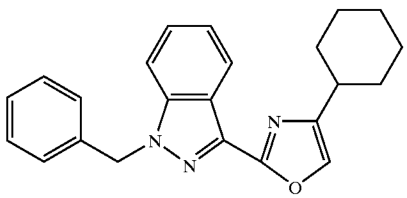 | F3 | 7% 88° C. | 0.622 (PEE/ 1:1) Al$_2$O$_3$ |
| III/114 | 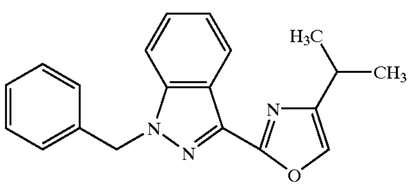 | F3 | 14% 54° C. | 0.667 (PE/E 1:1) Al$_2$O$_3$ |
| III/115 | 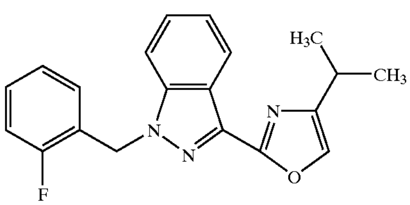 | F3 | 13% 68° C. | 0.667 (PE/E 1:1) Al$_2$O$_3$ |
| III/116 | 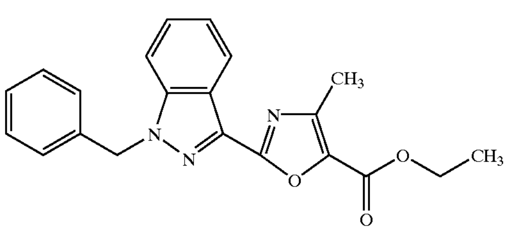 | F3 with (Cl, OEt structure shown) | 27% 121° C. | 0.453 (E/PE 1:1) Al$_2$O$_3$ |
| III/117 | 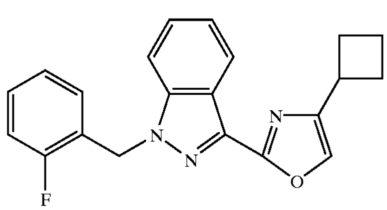 | F3 | 4% — | 0.331 (E/PE 1:3) Al$_2$O$_3$ |

TABLE III/3-continued

| Ex. No. | Structure | Preparation method | Yield/ melting point ° C. | R_f |
|---|---|---|---|---|
| III/118 | 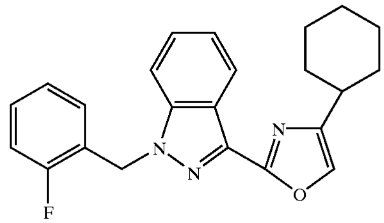 | F3 | 7% — | 0.674 (PE/E 1:1) Al$_2$O$_3$ |
| III/119 | 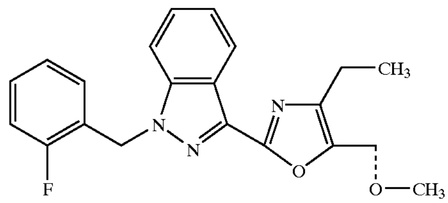 | D3 + alkytation | 53% 101° C. | 0.5 (Cyclo EE 2:1) Al$_2$O$_3$ |
| III/120 | 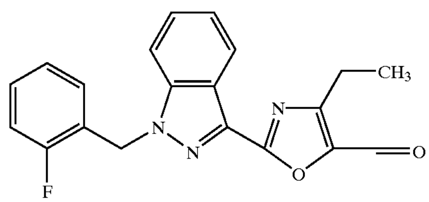 | D3 + oxidation | 35% 121° C. | 0.446 (Cyclo/ EE 2:1) Al$_2$O$_3$ |
| III/121 | 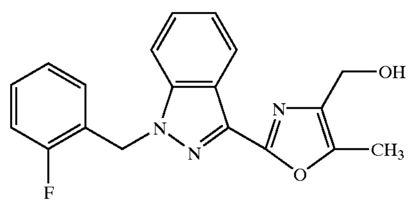 | H3 + reduction | 63% 142° C. | 0.037 (Hex/EE 3:1) |
| III/122 | 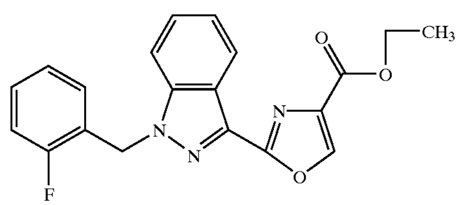 | F3 | 10% — | 0.55 (Cycl EE 2 1 |
| III/123 | 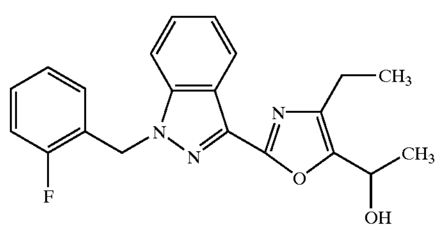 | D3 + oxidation + addition | 80% 81° C. | 0.086 (Hex/EE 3:1) |
| III/124 | 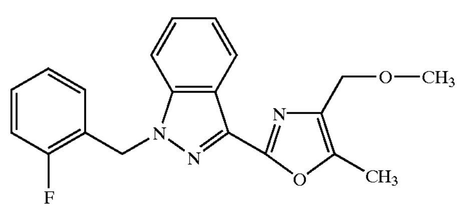 | H3 + reduction + alkylation | 97% 91° C. | 0.515 (Hex/EE 1:1) |

TABLE III/3-continued

| Ex. No. | Structure | Preparation method | Yield/ melting point ° C. | $R_f$ |
|---|---|---|---|---|
| III/ 125 | 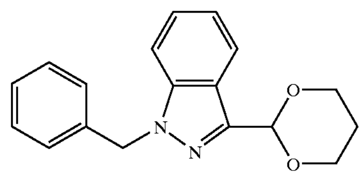 | I3 | 86% 111° C. | 0.162 (Hex/EE 3:1) |
| III/ 126 | 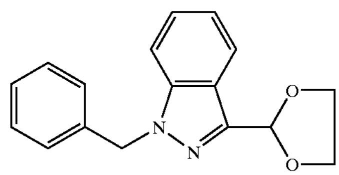 | I3 | 92% 83° C. | 0.179 Hex/EE 3:1) |
| III/ 127 | 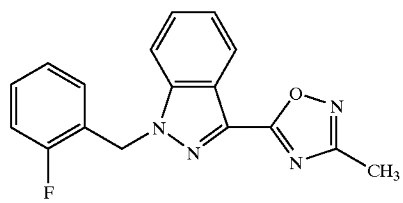 | J3 | 38% 173° C. | 0.30 (H:EE 3:1) |
| III/ 128 | 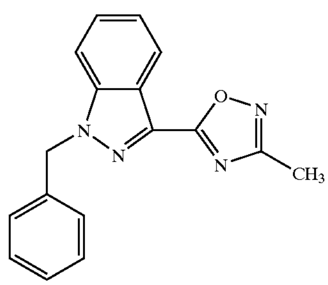 | J3 | 21% 155° C. | 0.29 (H/EE 3:1) |
| III/ 129 | 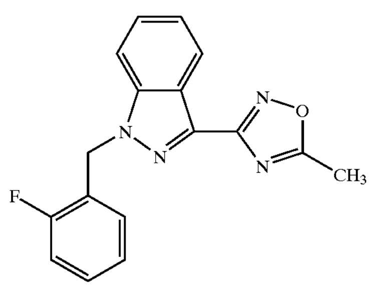 | J3 | | |
| III/ 130 | 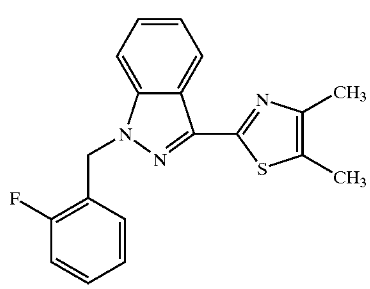 | B3 | 38% 131° C. | 0.46 (Cy:EE 10:1) |

TABLE III/3-continued

| Ex. No. | Structure | Preparation method | Yield/ melting point °C. | $R_f$ |
|---|---|---|---|---|
| III/131 | 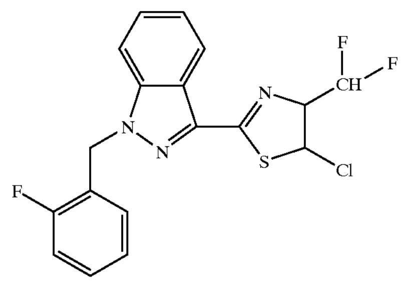 | B3 | 86% 123° C. | 0.43 (Cy:EE 10:1) |
| III/132 | 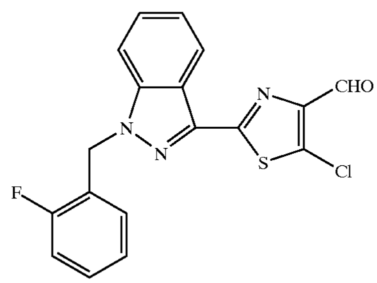 | B3 | 78% 166° C. | 0.41 (Cy:EE 10:1) |
| III/133 | 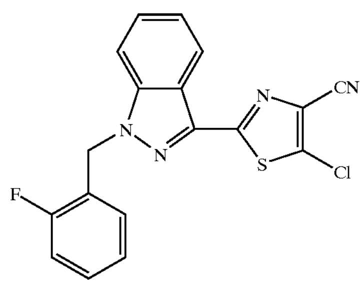 | B3 | 73% 162° C. | 0.43 (Cy:EE 10:1) |

Examples of the Process According to the Invention for the Preparation of the oxazolyl Compounds of the General Formula III-XXIX and Compounds in Which $R^{42}$ Represents a Radical of the Formula III-XXVIII In the following descriptions of experiments, the retention factors $R_f$ are measured on silica gel TLC, unless stated otherwise. H=hexane, EE=ethyl acetate.

Process Example 1

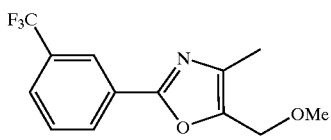

A mixture of 10 g of 3-(m-trifluoromethylbenzoylamido)-1,1-dichlorobut-1-ene, 5.1 g of sodium methylate and 35 ml of dimethylacetamide is stirred at 25° C. overnight, 50 ml of water are then added and the mixture is extracted several times with methylene chloride. The methylene chloride phase is separated off, dried with sodium sulphate and filtered and the solvent is removed in a vacuum rotary evaporator. Distillation of the resulting crude product gives 7.3 g of 4-methyl-5-methoxymethyl-2-(m-trifluorophenyl)-oxazole (boiling range 96–100° C./0.2 mbar).

Preparation of the 1,1-dichloro-3-(m-trifluoromethylbenzoylamido)-but-1-ene employed 1st Stage

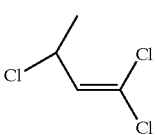

A mixture of 615 g of 1,1,1,3-tetrachlorobutane, obtained by addition, initiated by free radicals, of carbon tetrachloride onto propene, 13.3 g of tetrabutylammonium bromide and a solution of 138.2 g of sodium hydroxide in 390 ml of water is mixed thoroughly by stirring at room temperature for 24 hours. 2 l of water are then added, the phases are separated and the organic phase is dried with sodium sulphate. A mixture of 1,1,3-trichloro-but-1-ene and 1,1,1-trichloro-but-2-ene is obtained by distillation of the crude product (492 g of boiling range 45–50° C./20 mbar).

2nd Stage

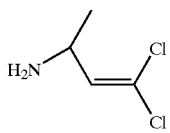

210 g of a mixture of 1,1,3-trichloro-but-1-ene and 1,1,1-trichloro-but-2-ene and 52 ml of anhydrous hydrocyanic acid are metered simultaneously into a solution, heated at 40° C., of 38 g of H$_2$O in 568 g of concentrated sulphuric acid in the course of 1 hour, while stirring. A further 78 ml of hydrocyanic acid are then added in the course of 2 hours. After a further reaction time of 2 hours, the excess hydrocyanic acid is distilled off. The reaction mixture is rendered alkaline with 20% strength sodium hydroxide solution and the crude product (195 g) is separated off by extraction with methylene chloride.

This crude product is mixed with 950 ml of half-concentrated hydrochloric acid, while stirring, the mixture being heated at the boiling point under reflux cooling. After 24 hours, the mixture is cooled and a small amount of by-product is removed by extraction with methylene chloride. The aqueous phase is concentrated to dryness in a rotary evaporator. Half-concentrated sodium hydroxide solution is then added and the mixture is stirred, the pH being adjusted to 9. The amine which separates out is isolated and distilled. 156 g of 3-amino-1,1-dichloro-but-1-ene are obtained, boiling point 45–50° C./ 18 mbar.

3rd Stage

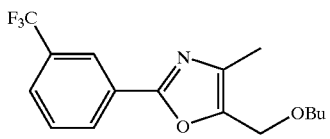

A solution of 26.9 g of m-trifluoromethylbenzoyl chloride in 25 ml of methylene chloride is added dropwise to a mixture of 21.0 g of 3-amino-1,1-dichloro-but-1-ene, 35 ml of methylene chloride and a solution of 15.9 g of sodium carbonate in 45 ml of water in the course of 30 minutes, while cooling with ice and stirring vigorously. After a reaction time of a further hour, the phases are separated. Concentration of the organic phase gives 39.0 g of 2,2-dichloro-3-(m-trifluoromethylbenzoylamido)-but-1-ene.

Process Example 2

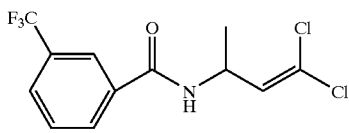

A mixture of 1,1-dichloro4-(m-trifluoromethylbenzoylamido)-but-1-ene, 4.2 g of sodium butylate and 35 ml of dimethylacetamide is heated at 100° C. for 7 hours, while stirring. After the reaction, the mixture is worked up analogously to Example 1. Vacuum distillation of the resulting crude product gives 6.4 g of 5-butoxymethyl-4-methyl-2-(m-trifluorophenyl)-oxazole (boiling range 106–110° C./0.2 mbar).

Process Example 3

A solution of 1.8 g of 3-acetamido-1,1-dichlorobut-1-ene and 1,0 g of sodium methylate in 20 ml of methanol is heated at the boiling point under reflux for 24 hours. Thereafter, the methanol is distilled off, the residue is taken up in 5 ml of water and 30 ml of methylene chloride and the organic phase is separated off and distilled in vacuo. 0.9 g of 2,4-dimethyl-5-methoxymethyl-oxazole is obtained, boiling point 54° C./20 mbar.

Process Example 4

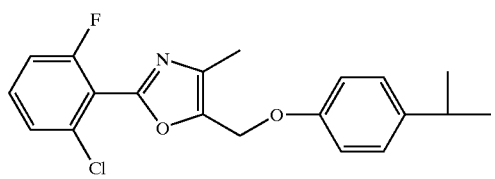

A mixture of 7 g of 3-(2-chloro-6-fluorobenzoylamido)-1,1-dichloro-but-1-ene, 11.7 g of sodium 4-tert-butylphenolate and 100 ml of N-methylpyrrolidone is heated at 100° C. for 8 hours, while stirring. The solvent is then separated off by vacuum distillation, the residue is taken up in water and methylene chloride and the organic phase is separated off, dried with sodium sulphate and freed from the solvent in a vacuum rotary evaporator. The crude product is purified by chromatography. 5.1 g of 2-(2-chloro-6-fluorophenyl)-4-methyl-5-(4-tert-butylphenoxymethyl)-oxazole are obtained.

Process Example 5

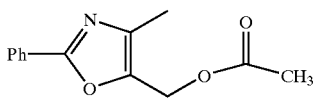

A mixture of 5 g of 3-benzoylamido-1,1-dichloro-but-1-ene, 36 g of sodium acetate and 500 ml of N-methylpyrrolidone is heated at 150° C. for 36 hours, while stirring. The crude product is then isolated in a manner analogous to that described in Example 4. Vacuum distillation gives 35 g of 5-acetoxymethyl-4-methyl-2-phenyl-oxazole (boiling range 88–91° C./0.1 mbar).

Process Example 6

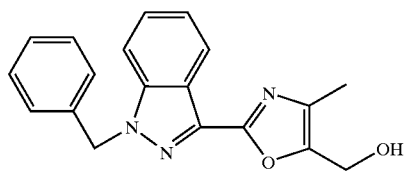

80 µl of NaOH, 1M, were added to 15 mg of 3-(1-benzylindazole-3-carboxamido)-1,1-dichlorobut-1-ene (40 µmol) in 20 µl of N-methylpyrrolidone under argon and the mixture was heated at 55° C. for 1 hour. It was cooled and 0.8 ml of water and 8 ml of ethyl acetate were added. The organic phase was concentrated and the residue was purified by preparative TLC (SiO$_2$). 9.9 mg (77%) of 2-(1-benzylindazol-3-yl)-5-hydroxymethyl-4-methyl-oxazole were obtained (melting point 127–129° C.).

MS (DCl/NH$_3$): 320 (100, MH$^+$). R$_f$: 0.17 (H:EE 1:1).

Process Example 7

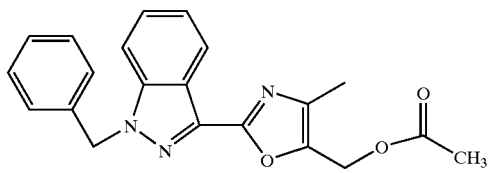

(For this example, the amide intermediate stage was prepared in situ from the formula 3a and an acid chloride.)

500 mg of 1-benzylindazole-3-carboxyl chloride (1.847 mmol), 260 mg of 3-amino-1,1-dichloro-but-1-ene (1.847 mmol) and 318 mg of sodium acetate (3.88 mmol) were stirred in 4 ml of N-methylpyrrolidone at 150° C. under argon for 5 days. The crude mixture was cooled, water was added and the mixture was extracted several times with ethyl acetate. The organic phases were dried (over $Na_2SO_4$) and concentrated and the residue was chromatographed ($SiO_2$, petroleum ether/ethyl acetate 3:1). Two products were isolated: 1,1-dichloro-3-(1-benzylindazole-3-carboxamido)-but-1-ene (410 mg, 59%) $R_f$: 0.26 (H:EE 3:1) and 5-acetoxymethyl-2-(1-benzylindazol-3-yl)-4-methyloxazole (160 mg, 24%).

MS (DCl/$NH_3$): 362 (100, $MH^+$). $R_f$: 0.17 (H:EE 3:1).

Process Example 8

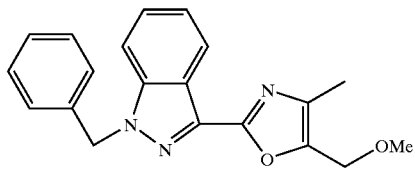

100 mg of 3-(1-benzylindazole-3-carboxamido)-1,1-dichloro-but-1-ene (0.267 mmol) and 29 mg of sodium methylate were stirred in 0.5 ml of N-methylpyrrolidone at 100° C. under argon overnight. The crude mixture was cooled and purified directly by column chromatography ($SiO_2$, cyclohexane:ethyl acetate 3:1). 35.9 mg (40%) of 2-(1-benzylindazol-3-yl)-5-methoxymethyl-4-methyloxazole were isolated as a yellowish oil.

MS (DCl/$NH_3$): 334 (100, $MH^+$). $R_f$: 0.67 ($CH_2Cl_2$:MeOH 100:5).

Process Example 9

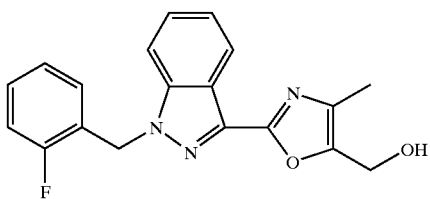

730 mg of 1,1-dichloro-3-[1(2-fluorobenzyl)indazole-3-carboxamido]-but-1-ene (1.86 mmol) and 3.75 ml of NaOH, 1N (3.75 mmol) were stirred in 7.4 ml of N-methylpyrrolidone at 50° C. under argon overnight. After cooling, the mixture was poured onto ice-water and the product which had precipitated out was filtered off and dried. Finally, it was purified by column chromatography ($SiO_2$, cyclohexane:ethyl acetate 2:1). 375 mg (60%) of 2-[1-(2-fluorobenzyl)indazol-3-yl]-5-hydroxymethyl- 4-methyl-oxazole were obtained as white crystals.

Melting point 144° C.

MS (ESI-POSITIVE): 338 (100, $MH^+$). $R_f$: 0.20 (H:EE 1:1).

The 1,1-dichloro-3-[1-(2-fluorobenzyl)indazole-3-carboxamido]-but-1-ene employed was prepared as follows: 120 µl of pyridine were added to 400 mg of 1-(2-fluorobenzyl)-indazole-3-carboxyl chloride (1.385 mmol) and 200 mg of 3-amino-1,1-dichloro-but-1-ene in 1.5 ml of THF and the mixture was stirred at room temperature for 3 hours. Ethyl acetate and water were then added. The organic phase was dried over sodium sulphate and concentrated. The crude product 1,1-dichloro-3-[1-(2-fluorobenzyl)indazole-3-carboxamido]-but-1-ene is pure enough, according to TLC, to be further reacted directly.

$R_f$: 0.32 (H:EE 3:1).

Process Example 10

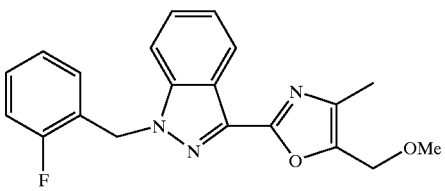

136 mg of 1,1-dichloro-3-[1(2-fluorobenzyl)indazole-3-carboxamido]-but-1-ene (0.267 mmol) and 47 mg of sodium methylate were stirred in 0.6 ml of N-methylpyrrolidone at 100° C. under argon overnight. The crude mixture was cooled and purified directly by column chromatography ($SiO_2$). 24 mg (20%) of 2-[1-(2-fluorobenzyl)-indazol-3-yl]-5-methoxymethyl-4-methyl-oxazole were isolated as yellowish crystals.

Melting point 86–88° C. MS (ESI-POSITIVE): 374 (65, $M+Na^+$), 352 (100, $MH^+$). $R_f$: 0.18 ($CH_2Cl_2$:MeOH 100:1).

Process Example 11

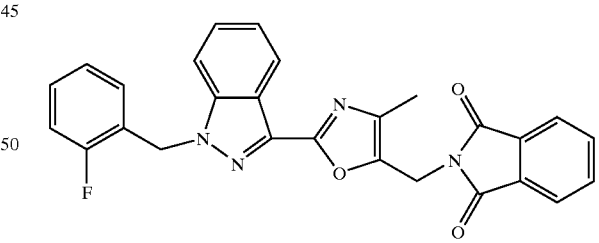

136 mg of 1,1-dichloro-3-[1-(2-fluorobenzyl)indazole-3-carboxamido]-but-1-ene (0.267 mmol) and 164 mg of potassium phthalimide were stirred in 0.6 ml of N-methylpyrrolidone at 150° C. under argon overnight. The N-methylpyrrolidone was then stripped off under a high vacuum at 60° C. and the residue was chromatographed ($SiO_2$, cyclohexane/ethyl acetate 2:1) to give 48.5 mg (36%) of 2-[1-(2-fluorobenzyl)-indazole-3-yl]-4-methyl-5-(N-phthalimidomethyl)-oxazole. Yellowish crystals.

Melting point 175–177° C. MS (ESI-POSITIVE): 467 (100, $MH^+$). $R_f$: 0.64 ($CH_2Cl_2$:MeOH 100:1).

Process Example 12

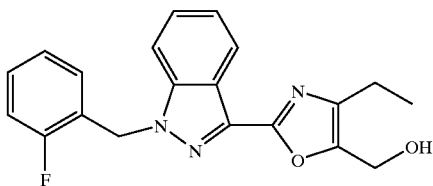

1.05 g of 1,1-dichloro-3-[1-(2-fluorobenzyl)indazole-3-carboxamido]-pent-1-ene (2.58 mmol) and 5.20 ml of NaOH, 1N (5.20 mmol) were stirred in 15 ml of N-methylpyrrolidone at 50° C. under argon for 2 days. After cooling, the mixture was poured onto ice-water and extracted several times with ethyl acetate. The organic phase was dried (sodium sulphate) and concentrated (N-methylpyrrolidone stripped off under a high vacuum). The residue was purified by column chromatography (aluminium oxide, cyclohexane/ethyl acetate 2:1). 470 mg (52%) of 5-ethyl-2-[1-(2-fluorobenzyl)-indazol-3-yl]-5-hydroxymethyl-oxazole were obtained as white crystals.

Melting point 137–139° C. MS (ESI-POSITIVE): 352 (100, MH$^+$). R$_f$: 0.08 (aluminium oxide, cyclohexane:EE 2:1).

PREPARATION EXAMPLES FOR EMBODIMENT IV OF THE INVENTION

Example IV/134

1-(2-Cyanobenzyl)-3-(5-(1,3-dioxolan-2-yl)furan-2-yl)-indazole

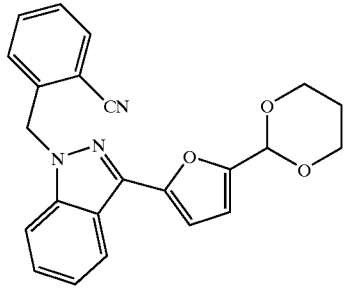

A solution of 2 g (7.41 mmol) of 3-(5-(1,3-dioxolan-2-yl)-furan-2-yl)indazole in 10 ml of DMF is added to a suspension of 355 mg of NaH (60 per cent in paraffin) in 10 ml of DMF under argon and the mixture is stirred at room temperature for 1 hour. 1.5 g of 2-cyanobenzyl bromide are then added. The mixture is stirred at 100° C. for 30 minutes, introduced into water and extracted with ethyl acetate, the organic phase is dried with sodium sulphate and evaporated in vacuo and the residue is chromatographed over silica gel using toluene/ethyl acetate mixtures as the eluent. 2.1 g (73.5% of theory) of an oil are obtained.

R$_f$ (SiO$_2$, toluene/ethyl acetate 1:1): 0.63

Example IV/135

1-(2-Cyanobenzyl)-3-(5-formyl-2-furanyl)-indazole

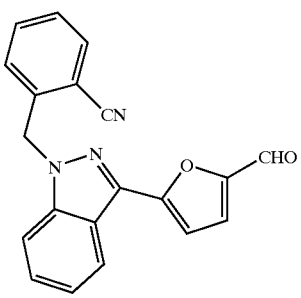

2.1 g (5.5 mmol) of 1-(2-cyanobenzyl)-3-(5-(1,3-dioxolan-2-yl)furan-2-yl)-indazole are dissolved in 20 ml of acetone, and 40 ml of 50% strength acetic acid are added. The mixture is boiled for 1 hour, introduced into water and extracted with ethyl acetate and the organic phase is washed with NaHCO$_3$ solution, dried with sodium sulphate and evaporated in vacuo to give 1.61 g (89% of theory) of a solid.

Melting point: 137° C.

R$_f$ (SiO$_2$, toluene/ethyl acetate 4:1): 0.4

Example IV/136

1-(2-Cyanobenzyl)-3-(5-hydroxymethylfuran-2-yl)-indazole

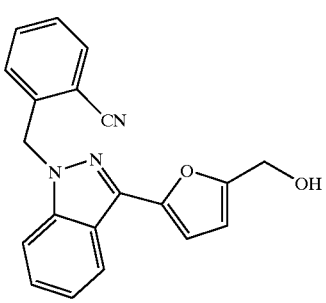

0.8 g (2.44 mmol) of 1-(2-cyanobenzyl)-3-(5-formyl-2-furanyl)-indazole is suspended in 50 ml of propanol, and 0.8 g of NaBH$_4$ is slowly added at 0° C. After the mixture has been stirred at room temperature for 1 hour, the clear solution is introduced into water and extracted with ethyl acetate, the organic phase is dried with sodium sulphate and evaporated in vacuo and the residue is chromatographed over silica gel using toluene/ethyl acetate mixtures as the eluent. 600 mg (75% of theory) of crystals are obtained.

Melting point 147° C.

R$_f$ (SiO$_2$, toluene/ethyl acetate 1:1): 0.52

Example IV/137

1-Benzyl-3-[5-(1,3-dioxolan-2-yl)-furan-2-yl]-indazole

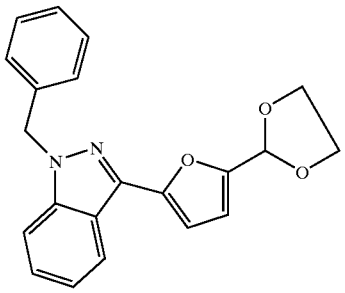

661 mg of 5-(1,3-dioxolan-2-yl)-2-tributylstannyl-furan (1.54 mmol) (M. Yamamoto, H. Izukawa, M. Saiki, K. Yamada, J. Chem. Soc. Chem. Comm. 1988, 560), 431.5 mg of 1-benzyl-3-iodoindazole (1.29 mmol) and 90 mg of tetrakistriphenylphosphine-palladium (0.078 mmol) in 2.5 ml of DMF were heated at 80° C. under argon for 10 hours. After cooling, water was added to the mixture and the mixture was extracted with ethyl acetate. The organic phases were dried with sodium sulphate and concentrated. Chromatography ($SiO_2$; petroleum ether. ethyl acetate 9:1) gave 381.3 mg of a viscous oil.

$R_f$: 0.16 (hexane/ethyl acetate 3:1)

Example IV/138

1Benzyl-3-(5-formylfuran-2-yl)-indazole

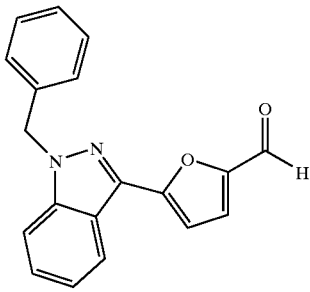

336 mg of 1-benzyl-3-[5-(1,3-dioxolan-2-yl)-furan-2-yl]-indazole (0.97 mmol) were heated under reflux with a pair of crystals of p-toluenesulphonic acid in 5 ml of acetone and 0.3 ml of water for 20 hours. Thereafter, 40 ml of ether were added to the reaction mixture. The organic phase was washed with a little sodium chloride solution, dried over sodium sulphate and concentrated. The residue crystallized slowly. The crystals were washed with a little ether and dried in vacuo: 210.4 mg.

$R_f$: 0.24 (hexane/ethyl acetate 3:1)

Melting point: 97–99° C.

Example IV/139

1-[5-(1-Benzylindazol-3-yl)-furan-2-yl]-ethanol

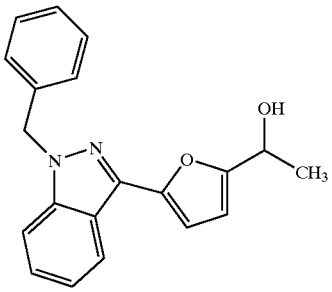

300 l of an MeLi solution (1.6 M in ether; 0.480 mmol) were added dropwise to a solution, cooled to −78° C., of 1-benzyl-3-(5-formylfuran-2-yl)-indazole (134.1 mg; 0.44 mmol) in 3 ml THF. After 10 minutes, aqueous $NH_4Cl$ was added to the mixture and the mixture was extracted with ether. The organic phase was washed with a sodium chloride solution, dried over sodium sulphate and concentrated. Chromatography ($SiO_2$; petroleum ether: ethyl acetate 2:1) gave 133 mg of a viscous oil.

$R_f$: 0.11 (hexane/ethyl acetate 3:1)

MS (Cl, $NH_3$): 319 ($M+H^+$, 100).

Example IV/140

3-(5-Acetylfuran-2-yl)-1-benzyl-indazole

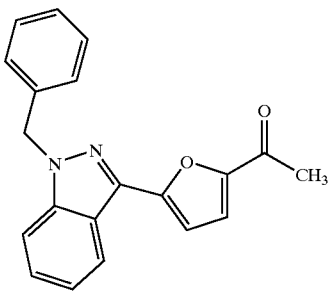

A mixture of 1-[5-(1-benzylindazol-3-yl)-furan-2-yl]-ethanol (51.2 mg; 0.160 mmol) and 250 mg of $MnO_2$ (2.9 mmol) in 2 ml of $CHCl_3$ was heated under reflux. After 12 hours, a further 250 mg of $MnO_2$ were added. After a further 12 hours, the mixture was filtered through Celite, the filtrate was concentrated and the residue was chromatographed ($SiO_2$; petroleum ether:ethyl acetate 3:1). 29.8 mg of a pale yellow solid were obtained.

$R_f$: 0.21 (hexane/ethyl acetate 3:1)

Melting point: 99–100° C.

Example IV/141

3-(5-Azidomethylfuran-2-yl)-1-benzyl-indazole

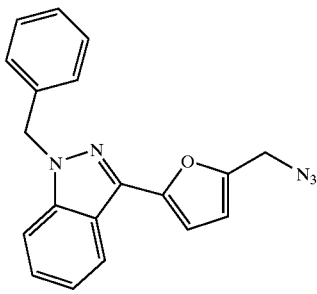

195.1 mg of 1-benzyl-3-(5-hydroxymethylfuran-2-yl)-indazole (0.64 mmol) (Kuo S.-C., Yu Lee F., Teng C.-M. EP 0 667 345 A1), 252 mg of triphenylphosphine (0.96 mmol) and 60.3 mg of sodium azide (0.93 mmol) were dissolved in 2.5 ml of DMF. 308.4 mg of carbon tetrabromide were added and the resulting mixture was stirred at room temperature for 20 hours. After addition of 5 ml of water, it was extracted with ethyl acetate. The organic phase was washed with a sodium chloride solution, dried over sodium sulphate and concentrated. Chromatography (SiO$_2$; cyclohexane:ethyl acetate 2:1) gave 206.7 mg of a viscous oil, which slowly solidifies.

$R_f$: 0.63 (hexane/ethyl acetate 1:1)

Melting point 51–52° C.

Example IV/142

3-(5-Aminomethylfuran-2-yl)-1-benzyl-indazole

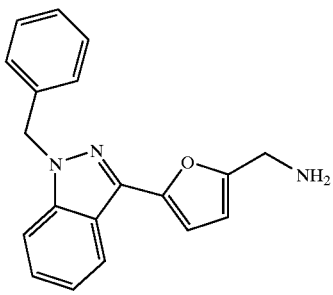

121.5 mg of 3-(5-azidomethylfuran-2-yl)-1-benzyl-indazole (0,369 mmol) and 102 mg of triphenylphosphine (0.389 mmol) were stirred in 1 ml of THF for 3.5 hours. 10 µl of water were then added. After 24 hours, ether and aqueous HCl, 0.3M, were added to the reaction mixture. The solid which had been filtered off and the aqueous phase were combined, rendered alkaline with NaOH, 2M, and extracted with ether. The organic phase was washed with a little water and then with a sodium chloride solution, dried over sodium sulphate and concentrated. 79.9 mg of a yellow oil were obtained.

Example IV/143

1-Benzyl-3-(5-nitrofuran-2-yl)-indazole

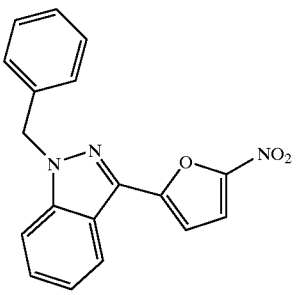

800 mg of 5-nitrofuran-2-yl phenyl ketone benzylhydrazones (mixture of E+Z, 2.49 mmol) were dissolved in 35 ml of methylene chloride. 1.99 g of lead tetraacetate (4.49 mmol) and 15.6 ml of BF$_3$ etherate (50% in ether, 62 mmol) were added and the mixture was heated under reflux for 1 hour. After cooling, the reaction mixture was poured onto ice and the organic phase was separated off, washed with 0.2M NaOH and then water, dried over sodium sulphate and concentrated. Chromatography gave 140 mg of yellow crystals.

$R_f$: 0.20 (petroleum ether/ethyl acetate 10:1)

Melting point: 148–151° C. (decomposition)

The compounds summarized in Tables IV/1, IV/2, IV/3, IV/4 and IV/5 were prepared analogously to the instructions of the examples given above.

TABLE IV/1

| Ex. No. | Structure | R$_f$*/ melting point (° C.) | Yield (% of theory) |
|---|---|---|---|
| IV/144 | 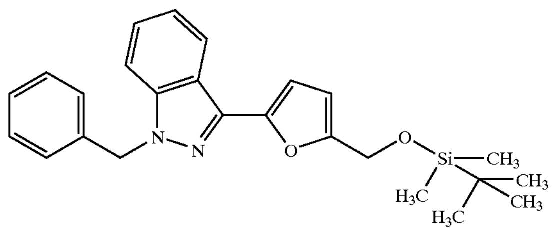 | 0.28(P10E1)/ oil | 91 |
| IV/145 | 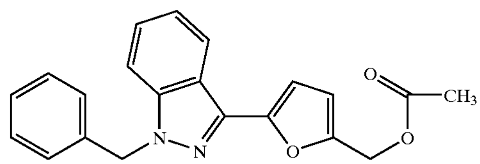 | 0.28(H3E1)/ 77 | 98 |
| IV/146 | 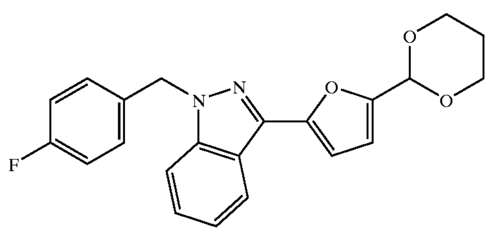 | 0.64(T1E1)/oil | 87 |
| IV/147 | 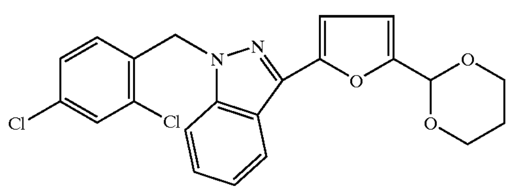 | 0.49(T4E1)/oil | 82 |
| IV/148 | 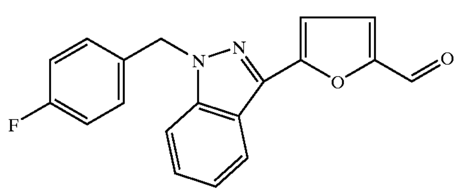 | 0.68(T1E1)/oil | 58 |
| IV/149 | 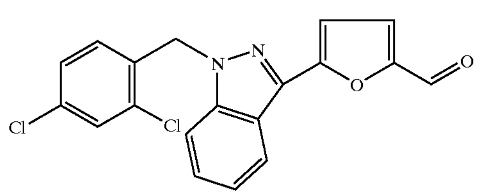 | 0.76(T1E1)/ 146 | 54 |
| IV/150 | 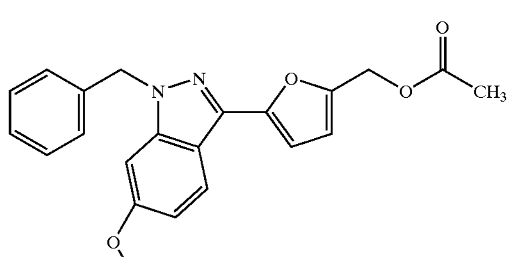 | 0.63(T1E1)/ 110 | 13 |

TABLE IV/2

[Structure: 1-(CH2-A4)-indazol-3-yl connected to furan-CH2OH]

| Ex. No. | A⁴ | Yield (% of theory) | Melting point °C |
|---|---|---|---|
| IV/168 | 2-OCH₃, 4-NO₂-phenyl | 42 | 126° C. |
| IV/169 | 3,5-bis(CF₃)-phenyl | 53 | |
| IV/170 | 3-NO₂-phenyl | 17 | |
| IV/171 | 2-F, 6-Cl-phenyl | 10 | |
| IV/172 | 2,6-Cl₂-phenyl | 19 | |
| IV/173 | 3-CF₃-phenyl | 8 | |
| IV/174 | 4-NO₂-phenyl | 11 | |

[Structure: 1-A4-indazol-3-yl connected to furan-CH2OH]

| Ex. No. | A⁴ | Yield (% of theory) | Melting point °C |
|---|---|---|---|
| IV/175 | 2-CN-phenyl | 7 | 117 |
| IV/176 | 2-OCH₃, 4-NO₂-phenyl | 8 | 84 |
| IV/177 | 3,5-bis(CF₃)-phenyl | 56 | 106 |
| IV/178 | 3-NO₂-phenyl | 22 | |

TABLE IV/3

TABLE IV/4

| Ex. No. | Structure | Yield (% of theory) | Melting point °C./$R_f$ |
|---|---|---|---|
| IV/179 | 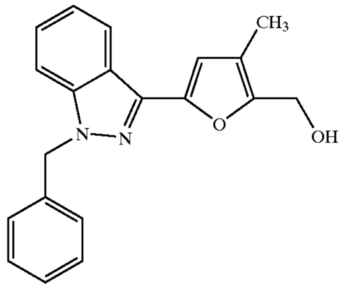 | 52 | 146 |
| IV/180 | 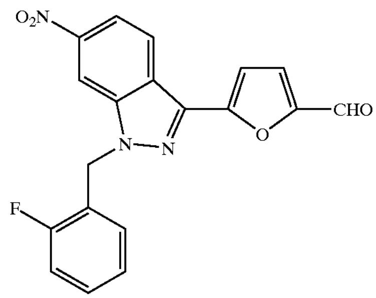 | 88 | 154<br>$R_f$ = 0.15<br>(H:EE 3:1) |
| IV/181 | 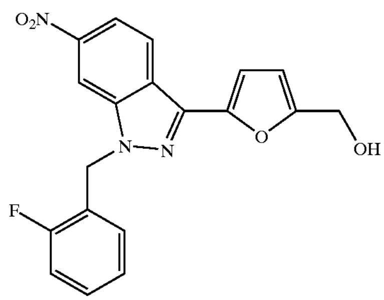 | 85 | 155<br>$R_f$ = 0.39<br>(H:EE 1:1) |

TABLE IV/5
| Ex. No. | Structure | Yield/ melting point | $R_f$ |
|---|---|---|---|
| IV/182 | 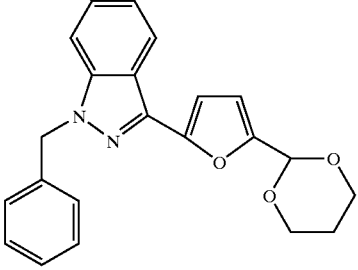 | 88% 183° C. | 0.24 (Cy:EE 2:1) |
| IV/183 | 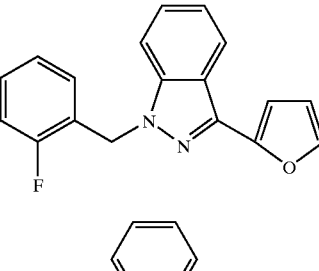 | 83% 109° C. | 0.25 (H:EE 3:1) |
| IV/184 | 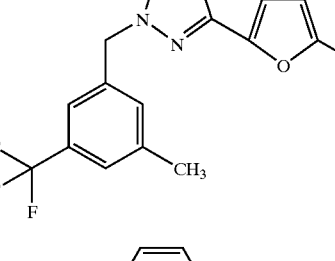 | 67% 155° C. | 0.20 (H:EE 3:1) |
| IV/185 | 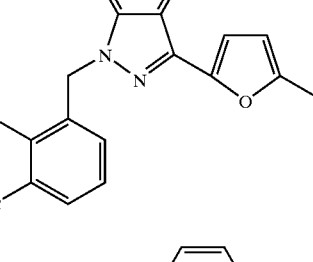 | 86% 93° C. | 0.38 (H:EE 1:1) |
| IV/186 | 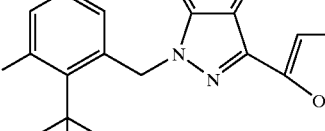 | 52% 90° C. | 0.40 (H:EE 3:1) |

What is claimed is:

1. A Heterocyclylmethyl-substituted pyrazole derivative of the formula (I-I)

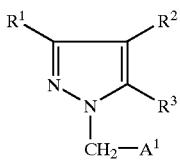

(I-I)

in which
R$^1$ represents a 5-membered aromatic heterocyclic ring having one heteroatom from the series consisting of S, N and/or O, or represents phenyl, which are optionally substituted up to 3 times in an identical or different manner by formyl, carboxyl, mercaptyl, hydroxyl, straight-chain or branched acyl, alkylthio, alkoxy or alkoxycarbonyl having in each case up to 6 carbon atoms, nitro, cyano, halogen, phenyl or straight-chain or branched alkyl having up to 6 carbon atoms, which in its turn can be substituted by hydroxyl, amino, carboxyl, straight-chain or branched acyl, alkoxy, alkoxycarbonyl or acylamino having in each case up to 5 carbon atoms or by a radical of the formula —OR$^4$, wherein
R$^4$ denotes straight-chain or branched acyl having up to 5 carbon atoms or a group of the formula —SiR$^5$R$^6$R$^7$, wherein
R$^5$, R$^6$ and R$^7$ are identical or different and denote aryl having 6 to 10 carbon atoms or alkyl having up to 6 carbon atoms,
and/or are substituted by a radical of the formula

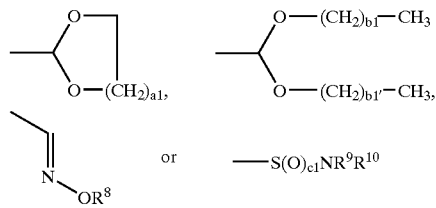

wherein
b1 and b1' are identical or different and denote the number 0, 1, 2 or 3,
a1 denotes the number 1, 2 or 3,
R$^8$ denotes hydrogen or straight-chain or branched alkyl having up to 4 carbon atoms,
c1 denotes the number 1 or 2 and
R$^9$ and R$^{10}$ are identical or different and denote hydrogen or straight-chain or branched alkyl having up to 10 carbon atoms, which is optionally substituted by cycloalkyl having 3 to 8 carbon atoms or by aryl having 6 to 10 carbon atoms, which in its turn can be substituted by halogen, or
denote aryl having 6 to 10 carbon atoms, which is optionally substituted by halogen, or
denote cycloalkyl having 3 to 7 carbon atoms, or
R$^9$ and R$^{10}$, together with the nitrogen atom, form a 5- to 7-membered saturated heterocyclic ring, which can optionally contain a further oxygen atom or a radical —NR$^{11}$,
wherein
R$^{11}$ denotes hydrogen, straight-chain or branched alkyl having up to 4 carbon atoms or a radical of the formula

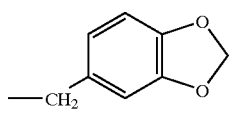

or denotes benzyl or phenyl, wherein the ring systems are optionally substituted by halogen,
R$^2$ and R$^3$, including the double bond, form a 5-membered aromatic heterocyclic ring having one heteroatom from the series consisting of S, N and/or O, or a phenyl ring, which are optionally substituted up to 3 times in an identical or different manner by formyl, carboxyl, hydroxyl, amino, straight-chain or branched acyl, alkoxy or alkoxycarbonyl having in each case up to 6 carbon atoms, nitro, cyano, azido, halogen, phenyl or straight-chain or branched alkyl having up to 6 carbon atoms, wherein the alkyl in its turn can be substituted by hydroxyl, amino, carboxyl, straight-chain or branched acyl, alkoxy or alkoxycarbonyl having in each case up to 5 carbon atoms,
and/or are optionally substituted by a radical of the formula —S(O)$_{c1'}$NR$^{9'}$R$^{10'}$, wherein c$_{1'}$, R$^{9'}$ and R$^{10'}$ have the above-mentioned meaning of c$_1$, R$^9$ and R$^{10}$ and are identical to or different from these,
A$^1$ represents a 5- to 6-membered aromatic or saturated heterocyclic ring having up to 3 heteroatoms from the series consisting of S, N and/or O, which is optionally substituted up to 3 times in an identical or different manner by mercaptyl, hydroxyl, formyl, carboxyl, straight-chain or branched acyl, alkylthio, alkyloxyacyl, alkoxy or alkoxycarbonyl having in each case up to 6 carbon atoms, nitro, cyano, trifluoromethyl, azido, halogen, phenyl or straight-chain or branched alkyl having up to 6 carbon atoms, which in its turn can be substituted by hydroxyl, carboxyl, straight-chain or branched acyl, alkoxy or alkoxycarbonyl having in each case up to 5 carbon atoms,
and/or is substituted by a group of the formula —(CO)$_{d1}$—NR$^{12}$R$^{13}$, wherein
d1 denotes the number 0 or 1,
R$^{12}$ and R$^{13}$ are identical or different and denote hydrogen, phenyl, benzyl or straight-chain or branched alkyl or acyl having in each case up to 5 carbon atoms,
or an isomer, salt or N-oxide thereof.

2. A compound according to claim 1 of the formula (I-I) in which
R$^1$ represents furyl, pyrrolyl, thienyl or phenyl, which are optionally substituted up to twice in an identical or different manner by formyl, carboxyl, hydroxyl, straight-chain or branched acyl, alkoxy or alkoxycarbonyl having in each case up to 5 carbon atoms, nitro, cyano, azido, fluorine, chlorine, bromine, phenyl or straight-chain or branched alkyl having up to 5 carbon atoms, which in its turn can be substituted by hydroxyl, amino, carboxyl, straight-chain or branched acyl, alkoxy, alkoxycarbonyl or acylamino having in each case up to 4 carbon atoms or by a radical of the formula —OR$^4$, wherein
R$^4$ denotes straight-chain or branched acyl having up to 4 carbon atoms, and/or are substituted by a radical of the formula

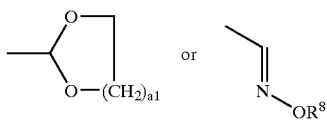

wherein
a1 denotes the number 1, 2 or 3,
R⁸ denotes hydrogen or straight-chain or branched alkyl having up to 3 carbon atoms,
R² and R³, including the double bond, form a furyl, thienyl or phenyl ring, which are optionally substituted up to 3 times in an identical or different manner by formyl, carboxyl, hydroxyl, amino, straight-chain or branched acyl, alkoxy or alkoxycarbonyl having in each case up to 5 carbon atoms, nitro, cyano, azido, fluorine, chlorine, bromine, phenyl or straight-chain or branched alkyl having up to 5 carbon atoms, which in its turn can be substituted by hydroxyl, amino, carboxyl, straight-chain or branched acyl, alkoxy or alkoxycarbonyl having in each case up to 4 carbon atoms,
A¹ represents tetrahydropyranyl, thienyl, furyl, tetrahydrofuranyl, pyrazinyl, morpholinyl, pyrimidyl, pyridazinyl or pyridyl, which are optionally substituted up to twice in an identical or different manner by hydroxyl, formyl, carboxyl, straight-chain or branched acyl, alkylthio, alkyloxyacyl, alkoxy or alkoxycarbonyl having in each case up to 4 carbon atoms, fluorine, chlorine, bromine, nitro, cyano, trifluoromethyl or straight-chain or branched alkyl having up to 4 carbon atoms, which in its turn can be substituted by hydroxyl, carboxyl, straight-chain or branched acyl, alkoxy or alkoxycarbonyl having in each case up to 4 carbon atoms,
and/or are substituted by a group of the formula —(CO)$_{d1}$—NR¹²R¹³, wherein
d1 denotes the number 0 or 1,
R¹² and R¹³ are identical or different and denote hydrogen, phenyl, benzyl or straight-chain or branched alkyl or acyl having in each case up to 4 carbon atoms,
or an isomer, salt or N-oxide thereof.

3. A compound according to claim 1 of the formula (I-I), in which
R¹ represents furyl, pyrrolyl, thienyl or phenyl, which are optionally substituted up to twice in an identical or different manner by formyl, straight-chain or branched acyl, alkoxy or alkoxycarbonyl having in each case up to 4 carbon atoms or straight-chain or branched alkyl having up to 4 carbon atoms, which in its turn can be substituted by hydroxyl, carboxyl, amino, straight-chain or branched acyl, alkoxy, alkoxycarbonyl or acylamino having in each case up to 3 carbon atoms,
and/or are substituted by a radical of the formula

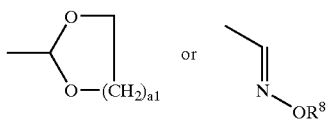

wherein
a1 denotes the number 1 or 2,
R⁸ denotes hydrogen or methyl,

R² and R³, including the double bond, form a furyl, thienyl or phenyl ring, which are optionally substituted up to twice in an identical or different manner by formyl, carboxyl, hydroxyl, amino, straight-chain or branched acyl, alkoxy or alkoxycarbonyl having in each case up to 4 carbon atoms, nitro, cyano, fluorine, chlorine, phenyl or straight-chain or branched alkyl having up to 3 carbon atoms, which in its turn can be substituted by hydroxyl, amino, carboxyl, straight-chain or branched acyl, alkoxy or alkoxycarbonyl having in each case up to 3 carbon atoms,
A¹ represents tetrahydropyranyl, tetrahydrofuranyl, thienyl, pyrimidyl, pyrazinyl, pyridazinyl, furyl or pyridyl, which are optionally substituted up to twice in an identical or different manner by formyl, carboxyl, straight-chain or branched acyl, alkylthio, alkyloxyacyl, alkoxy or alkoxycarbonyl having in each case up to 3 carbon atoms, fluorine, chlorine, bromine, nitro, cyano, trifluoromethyl, or straight-chain or branched alkyl having up to 3 carbon atoms, which in its turn can be substituted by hydroxyl, carboxyl, straight-chain or branched acyl, alkoxy or alkoxycarbonyl having in each case up to 3 carbon atoms,
and/or are substituted by a group of the formula —(CO)$_{d1}$—NR¹²R¹³$_1$, wherein
d1 denotes the number 0 or 1,
R¹² and R¹³ are identical or different and denote hydrogen or straight-chain or branched alkyl or acyl having in each case up to 3 carbon atoms,
or an isomer salt or N-oxide thereof.

4. A compound according to claim 1 of the formula (I-I), in which
R¹ represents furyl, which is optionally substituted by formyl or by the radical of the formula —CH₂—OH or

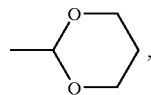

R² and R³, including the double bond, form a phenyl ring which is substituted by phenyl, fluorine or nitro,
A1 represents furyl, pyridyl, pyrimidyl, pyridazinyl, thienyl, tetrahydrofuranyl or tetrahydropyranyl, which are optionally substituted by chlorine, bromine, methoxy, methoxycarbonyl or carboxyl,
or an isomer, salt or N-oxide thereof.

5. A pharmaceutical composition comprising at least one compound of the formula (I) according to claim 1.

6. A pharmaceutical composition comprising at least one compound of the formula (I-I) according to claim 1 and at least one organic nitrate or an NO donor.

7. A process for preparing a compound of the formula (I-I) according to claim 1, comprising:
[A1] reacting compounds of the formula (I-II)

(I-II)

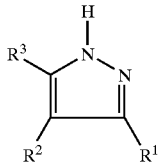

in which
R¹, R² and R³ are defined as in claim 1, with compounds of the formula (I-III)

   (I-III)

in which
A$^1$ is defined as in claim 1, and
D$^1$ represents triflate or halogen, in an inert solvent and, optionally in the presence of a base, or

[B1] reacting compounds of the formula (I-IV)

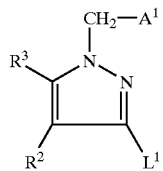   (I-IV)

in which
A$^1$, R$^2$ and R$^3$ are defined as in claim 1 and
L$^1$ represents a radical of the formula —SnR$^{14}$R$^{15}$R$^{16}$, ZnR$^{17}$, iodine or triflate wherein
  R$^{14}$, R$^{15}$ and R$^{16}$ independently denote straight-chain or branched alkyl having up to 4 carbon atoms and
  R$^{17}$ denotes hydrogen
with compounds of the formula (I-V)

   (I-V)

in which
R$^1$ is defined as in claim 1 and
in the case where L$^1$=SnR$^{14}$R$^{15}$R$^{18}$ or ZnR$^{17}$
T$^1$ represents triflate or halogen, and
in the case where L$^1$=iodine or triflate,
T$^1$ represents a radical of the formula SnR$^{14'}$R$^{15'}$R$^{16'}$, ZnR$^{17'}$ or BR$^{18'}$R$^{19'}$, wherein
  R$^{14'}$, R$^{15'}$R$^{16'}$ independently denote straight-chain or branched alkyl having up to 4 carbon atoms and
  R$^{17'}$ denotes hydrogen and
  R$^{18}$ and R$^{19}$ independently denote hydroxyl aryloxy having 6 to 10 carbon atoms or straight-chain or branched alkyl or alkoxy having in each case up to 5 carbon atoms, or together form a 5- or 6- membered carbocyclic ring,
in a palladium-catalysed reaction in an inert solvent.

8. The process according to claim 7, which is for the preparation of a compound of formula (I-I) which contains a radical —S(O)$_{c1}$NR$^9$R$^{10}$ or —S(O)$_{c1}$NR$^{9'}$R$^{10'}$, said process further comprising reacting an unsubstituted compound of formula (I-I) with thionyl chloride to produce an intermediate product, and thereafter reacting said intermediate product with HNR$^9$R$^{10}$ or HNR$^{9'}$R$^{10'}$.

9. The process according to claim 7, which further comprises introducing or varying R$^1$, R$^2$, R$^3$ and/or A$^1$ by reduction, oxidation, splitting off of protective groups and/or nucleophilic substitution.

10. The process according to claim 7 wherein in [A1], D$^1$ represents bromine or wherein in [B1], T$^1$ represents bromine.

11. Method for the treatment of cardiovascular diseases, said method comprising administering to a patient in need thereof an effective amount therefor of at least one compound of the formula (I-I) according to claim 1.

12. Method for treating the consequences of a cerebral infarction event said method comprising administering to a patient in need thereof an effective amount therefor of at least one compound of the formula (I-I) according to claim 1.

13. The method according to claim 12, wherein the cerebral infarction event is an apoplexia cerebri selected from the group consisting of apoplexy, cerebral ischaemias and crania-cerebral trauma.

* * * * *